US009597313B2

(12) United States Patent
Phillips et al.

(10) Patent No.: US 9,597,313 B2
(45) Date of Patent: Mar. 21, 2017

(54) COMPOSITION AND METHODS FOR THE ENTEROSORPTION AND MANAGEMENT OF TOXINS

(76) Inventors: Timothy D. Phillips, College Station, TX (US); Robert Hunt Carpenter, Bastrop, TX (US)

( * ) Notice: Subject to any disclaimer, the term of this patent is extended or adjusted under 35 U.S.C. 154(b) by 485 days.

(21) Appl. No.: 11/821,982

(22) Filed: Jun. 26, 2007

(65) Prior Publication Data

US 2008/0008763 A1    Jan. 10, 2008

Related U.S. Application Data

(60) Provisional application No. 60/816,824, filed on Jun. 27, 2006.

(51) Int. Cl.
*A61K 31/366* (2006.01)
*A61K 33/06* (2006.01)
*A61K 35/02* (2015.01)

(52) U.S. Cl.
CPC ............ *A61K 31/366* (2013.01); *A61K 33/06* (2013.01); *A61K 35/02* (2013.01)

(58) Field of Classification Search
None
See application file for complete search history.

(56) References Cited

U.S. PATENT DOCUMENTS

| 4,942,042 A | 7/1990 | Bhargava et al. |
|---|---|---|
| 5,165,946 A | 11/1992 | Taylor et al. |
| 5,178,832 A | 1/1993 | Phillips et al. |
| 5,192,547 A * | 3/1993 | Taylor ............................ 424/438 |
| 2008/0026079 A1 | 1/2008 | Carpenter et al. |

FOREIGN PATENT DOCUMENTS

| CN | 1326745 A | 12/2001 |
|---|---|---|
| EP | 1747775 | 1/2007 |
| RU | 2329815 | 7/2008 |
| UA | 30790 | 11/2008 |
| WO | 2007/011825 A2 | 1/2007 |
| WO | 2008/013631 | 1/2008 |
| WO | 2009/087091 | 7/2009 |
| WO | 2010/012720 | 2/2010 |

OTHER PUBLICATIONS

United States Patent and Trademark Office, Non-Final Office Action, U.S. Appl. No. 11/821,983, May 19, 2010.
Amendment Under 37 C.F.R. § 1.111 as filed with the United States Patent and Trademark Office on Oct. 19, 2010, U.S. Appl. No. 11/821,983.
Declaration Under 37 C.F.R. § 1.131 as filed with the United States Patent and Trademark Office on Oct. 19, 2010, U.S. Appl. No. 11/821,983.
United States Patent and Trademark Office, Final Office Action, U.S. Appl. No. 11/821,983, Jan. 5, 2011.
International Search Report and Written Opinion; Patentability; European Patent Office; Sep. 12, 2008.
Afriyie-Gyawu, Evans, Safety and efficacy of NovaSil Clay as a Dietary Supplement to Prevent Aflatoxicosis—Dissertation, Dec. 4, 2004, pp. 1-178.
URL: http://trouwusa.newmind.co/uk/dbimgs/ PRODINFORNovaSilPlus.pdf> [retrieved on Aug. 24, 2008].
Abdel-Wahhab, M, et al., "Potential Protective Effect of HSCAS and bentonite against Dietary Aflatoxicosis in Rat: with Special Reference to Chromosomal Aberrations", Natural Toxins, New York, NY, vol. 6 No. 5, Jan. 1, 1998, pp. 211-218.
Chinese Patent Office; Office Action; Chinese Patent Application No. 200780023950.4, Mar. 16, 2011.
Chinese Patent Office; Office Action; Chinese Patent Application No. 200780031609.3, Apr. 20, 2011.
Chinese Patent Office; Response to Office Action and Amended Claims (in Chinese); Chinese Patent Application No. 200780031609.3, 7 pages, Sep. 7, 2012.
Chinese Patent Office; Amended Claims (in English); Chinese Patent Application No. 200780031609.3, 3 pages, Sep. 7, 2012.
Indian Patent Office; Office Action; Indian Patent Application No. 00188/MUMNP/2009, 2 pages, Oct. 23, 2012.
Chinese Patent Office; Response to First Office Action (in Chinese); Chinese Patent Application No. 200780023950.4, 6 pages, Sep. 29, 2011.
Chinese Patent Office; Response to First Office Action (in Chinese); Chinese Patent Application No. 200780031609.3, 24 pages, Nov. 7, 2011.
Bin Zaid M.R, et al; Attapulgite in the Treatment of Acute Diarrhoea: A Double-Blind Placebo-Controlled Study; J Diarrhoeal Dis Res, 13(1), 44-46, Mar. 1995.
Szajewska H., et al; Smectite in the Treatment of Acute Infectious Diarrhoea in Children; Alimentary Pharmacology & Therapeutics, 23, 217-227, 2006.
Japanese Patent Office; Office Action; Japanese Patent Application No. 2009-518220, 4 pages, Sep. 25, 2012.
Japanese Patent Office; Office Action (English translation); Japanese Patent Application No. 2009-518220, 7 pages, Sep. 25, 2012.
Korean Patent Office; Office Action (Notice of Preliminary Rejection); Korean Patent Application No. 10-2009-7001704, 3 pages, Sep. 30, 2013.

(Continued)

*Primary Examiner* — Abigail Fisher
*Assistant Examiner* — Frank Choi
(74) *Attorney, Agent, or Firm* — Craig Conrad

(57) ABSTRACT

A composition and method for use as a preventive therapy to mitigate the effects of environmental toxins, and particularly aflatoxins in a subject. The subject may be at risk for hepatocellular carcinoma and aflatoxicosis. The composition comprising: an effective amount of an isolated low sodium, calcium aluminosilicate clay in a powder form, wherein the isolated low sodium, calcium aluminosilicate clay contains acceptable levels of dioxins and priority toxic heavy metal contamination, and is capable of preferentially binding aflatoxins in the gastrointestinal tract.

23 Claims, 10 Drawing Sheets

(56) References Cited

OTHER PUBLICATIONS

Korean Patent Office; Office Action (Notice of Preliminary Rejection)—English translation; Korean Patent Application No. 10-2009-7001704, 2 pages, Sep. 30, 2013.
European Patent Office; Response to Office Action; European Patent Application No. 07835883.5, 10 pages, May 17, 2012.
Chinese Patent Office; Office Action; Chinese Patent Application No. 200780031609.3, 11 pages, Apr. 25, 2012.
Japanese Patent Office; Amendment and Note of Refutation; Japanese Patent Application No. 2009-518220, 12 pages, Mar. 25, 2013.
Chen etal; Observation of Effects of Smectite Powder in Treatment of Leukemia Patents With Chemotherapy-Induced Oral Mucositis, Nanfang Journal of Nursing, Online article accessed on Jan. 17, 2013, Retrieved from the internet: URL: http//en.cnki/com/cn/Article_en/CJFDTOTAL-NFHL200401023.htm, 1 page, (2004), Abstract only.
Dodd, et al: Radiation-Induced Mucositis: A Randomized Clinical Trial of Micronized Sucralfate Versus Salt and Soda Mouthwashes, Cancer Invest., vol. 21, No. 1, pp. 21-33 (2003) abstract only.
Russian Patent Office; International Search Report; PCT Application No. PCT/US2012/061206; Jan. 24, 2013.
Russian Patent Office; International Search Report; PCT Application No. PCT/US2012/061385; Feb. 28, 2013.
Keefe, et al: Updated Clinical Practice Guidelines for the Prevention and Treatment of Mucositis; Cancer, vol. 109, No. 5, pp. 820-831 (2007).
Lin, et al: Effect of Montmorillonite Powder Mixed With Iodine Glycerin on Chemotherapy-Induced Oral Mucositis, Journal of Nursing, Online article accessed on Jan. 17, 2013, Retrieved from the internet: URL: http//en.cnki/comicn/Article_en/CJFDTOTAL-NFHL201006026.htm, 1 page, (2010), Abstract only.
Liu, S.; Curative Effect of Metronidazole Gargle and Smectite Powder on Oral Mucositis in Patients With Chronic Obstructive Pulmonary Disease; Modern Clinical Nursing; Online article accessed on Jan. 17, 2013, Retrieved from the internet: URL: http//en.cnki/com/cn/Article_en/CJFDTOTAL-XDLH200701015.htm, 1 page, (2007), Abstract only.
Yang, et al: Clinical Prevention and Control of Radioactive Oral Mucosa Injury by Montmorillonite Powder and Self Gargle Mouthwash, Journal of Clinical and Experimental Medicine, Online article accessed on Jan. 17, 2013, Retrieved from the internet: URL: http//en.cnki/com/cn/Article_en/CJFDTOTAL-SYLC200902022.htm, 1 page, (2009), Abstract only.
Ye; Clinical Analysis of 71 Cases With Oral Mucositis Induced by Tumor Radiochemotherapy With Montmorillonite Powder; Journal of Beihua University (Natural Science); Online article accessed on Jan. 18, 2013, Retrieved from the internet: URL: http//en.cnki/com/cn/Article_en/CJFDTOTAL-ZLYY200903012.htm, 1 page, (2009), Abstract only.
Chinese Patent Office; Third Office Action; Chinese Patent Application No. 200780031609.3; 11 pages; Feb. 20, 2013.
Chinese Patent Office; Response; Chinese Patent Application No. 200780023950.4; 9 pages; Mar. 14, 2013.
Taiwan Patent Office; Response; Taiwanese Patent Application No. 96123387; 32 pages; Mar. 1, 2013.
Japanese Patent Office; Response; Japanese Patent Application No. 2009-518,219; Jan. 24, 2013.
Allcock, H.R.; Introduction to Materials Chemistry; John Wiley & Sons, Inc.; 2008.
Chinese Patent Office; Office Action; Chinese Patent Application No. 200780023950.4; 11 pages; Dec. 4, 2012.
European Patent Office; Office Action; European Patent Application No. 07835883.5, 5 pages, Jan. 19, 2012.
Australian Patent Office; Office Action; Australian Patent Application No. 2007277428, 2 pages, Jan. 24, 2012.
Korean Patent Office; Argument and Amendment; Korean Patent Application No. 10-2009-7001704; Nov. 7, 2013.
Canadian Patent Office; Response to Office Action; Canadian Patent Application No. 2,656,239; Oct. 30, 2013.
Canadian Patent Office; Response to Office Action; Canadian Patent Application No. 2,659,072; Nov. 8, 2013.
Chinese Patent Office; Office Action (in Chinese); Chinese Patent Application No. 200780031609.3; Nov. 5, 2013.
Chinese Patent Office; Office Action (in English); Chinese Patent Application No. 200780031609.3; Nov. 5, 2013.
Indian Patent Office; Response to Office Action; Indian Patent Application No. 00188/MUMNP/2009; Apr. 23, 2013.
Canada Patent Office; Office Action; Canadian Patent Application No. 2,656,239; Apr. 30, 2013.
Australia Patent Office; Response to Office Action; Australian Patent Application No. 2007277428; Jun. 17, 2013.
Chinese Patent Office; Response to Office Action; Chinese Patent Application No. 200780031609.3; Jun. 20, 2013.
Russian Patent Office; International Search Report and Written Opinion; PCT Application No. PCT/US2012/061197; Mar. 14, 2013.
Canada Patent Office; Office Action; Canadian Patent Application No. 2,659,072; May 9, 2013.

\* cited by examiner

Figure 1
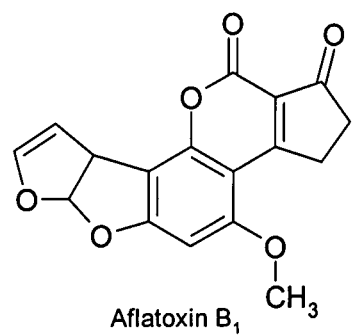
Aflatoxin B$_1$
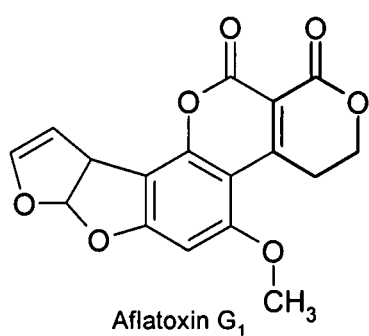
Aflatoxin G$_1$
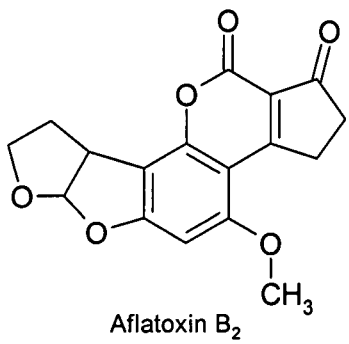
Aflatoxin B$_2$
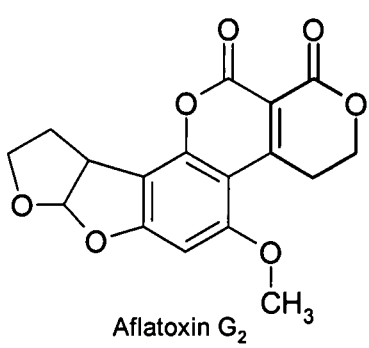
Aflatoxin G$_2$

Figure 2

| ANIMALS FED HSCAS | MYCOTOXIN IN FEED | HSCAS IN FEED (% and duration of exposure) | TOXICITY FROM HSCAS | MAJOR EFFECTS OF HSCAS CLAY REPORTED IN THE STUDY | REFERENCES |
|---|---|---|---|---|---|
| Chickens | Aflatoxins | (0.5; 28 d) | None | Growth inhibition diminished; gross hepatic changes prevented | Phillips et al. |
| Chickens | Aflatoxins | 0.5; 28 d | None | Growth inhibition diminished; decreased mortality | Kubena et al. |
| Chickens | Aflatoxins | 0.1/0.5 (24 h) | None | Reduced bioavailability of Aflatoxin to the liver and blood in a dose-dependent manner | Davidson et al. |
| Chickens | Aflatoxins | 0.5/1.0 (21 d) | None | Growth inhibitory effects reduced | Araba & Wyatt |
| Chickens | Aflatoxins | 0 – 1.0 (21 d) | None | Feed conversions improved; growth inhibition diminished | Doerr |
| Chickens | Aflatoxins | 1.0 (21 d) | None | Growth inhibition completely prevented | Ledoux et al. |
| Chickens | Afl | 0.5 (21 d) | None | Decreased growth inhibitory effects; no effect against ochratoxinl | Huff et al. |
| Chickens | Afl/Trichothecenes | 0.5 (21 d) | None | Diminished growth inhibition; no effect against trichothecenes | Kubena et al. |
| Chickens | Afl/Trichothecenes | 0.25/0.37/0.8 (21 d) | None | Diminished growth inhibition; no effect against trichothecenes | Kubena et al. |
| Chickens | None | 0.5/1.0 (14 d) | None | HSCAS did not impair phytate or inorganic phosphorous utilization | Chung & Baker |
| Chickens | None | 0.5/1.0 (14 d) | None | HSCAS did not impair utilization of riboflavin, vitamin A, or Mn; slight reduction of Zn | Chung et al. |
| Chickens | Aflatoxins | 0.125 – 0.5 (21) | None | Protected against vitamin A depletion in the livers of chicks exposed to aflatoxins | Pimpukdee et al. |
| Chickens | None (def. diets) | 0,5 (19 d) | None | Did not affect growth performance or tibial mineral concentrations of chicks | Southern et al. |
| Turkeys | Aflatoxins | 0.5 (21 d) | None | Decreased mortality | Kubena et al. |
| Turkeys | Aflatoxins | 0.5 (21 d) | None | Decreased urinary excretion of aflatoxin M1 | Edrington et al. |
| Pigs | Aflatoxins | 0.5 | None | Decreased DNA adducts in the liver and reduced tissue residues of total aflatoxins | Beaver et al. |
| Pigs | Aflatoxins | 0.5 (42 d) | None | Diminished growth inhibition | Lindemann et al. |
| Pigs | Aflatoxins | 0.5/2.0 (28 d) | None | Decreased growth inhibition; prevention of serum effects and hepatic lesions | Harvey et al. |
| Pigs | Aflatoxins | 0.5/2.0 (28 d) | None | Diminished growth inhibition, hepatic lesions and immunosuppression | Harvey et al. |
| Pigs | Aflatoxins | 0.5 (35 d) | None | Growth inhibitory effects reduced | Schell et al. |
| Pigs | Ochratoxins | 1.0 | None | No significant effect | Bauer |
| Pigs | Trichothecenes | 0.5/1.0 | None | No significant effect | Patterson & Young |
| Dogs | Aflatoxins | 0.5 (48 h) | None | Significantly reduced the bioavailability of aflatoxins and excretion of M1 in urine | Bingham et al. |
| Lambs | Aflatoxins | 2.0 (42 d) | None | Diminished growth inhibition and immunosuppression | Harvey et al. |
| Dairy Cows | Aflatoxins | 0.5/1.0 (28 d) | None | Reduction of aflatoxin M1 in milk | Harvey et al. |
| Dairy Goats | Aflatoxins | 1.0/2.0/4.0 (12 d) | None | Reduction of aflatoxin M1 in milk | Smith et al. |
| Rats | Aflatoxins | 0.5 (21 d) | None | Significant prevention of maternal and developmental toxicity | Mayura et al. |
| Rats | Aflatoxins | 0.5 (21) | None | Decreased growth inhibition in pregnant rats | Abdel-Wahhab et al. |
| Rats | Aflatoxins | 0.5 (48 h) | None | Decreased urinary excretion of aflatoxin metabolites (M1 and P1) | Sarr et al. |
| Rats | None (HSCAS only) | 0.25, 0.5, 1.0, 2.0 (6 months) | None | No adverse effects including vitamin utilization | Afriyie-Gyawu et al. |

COMPOSITION AND METHODS FOR THE ENTEROSORPTION AND MANAGEMENT OF TOXINS

This application claims priority to U.S. Provisional Patent Application Ser. No. 60/816,824, entitled "Composition and Methods for the Enterosorption and Management of Aflatoxins in Human Populations at Risk for Hepatocellular Carcinoma and Acute Aflatoxicosis," filed on Jun. 27, 2006, the entire content of which is hereby incorporated by reference.

STATEMENT OF RIGHTS TO INVENTIONS MADE UNDER FEDERALLY SPONSORED RESEARCH

Federal grants or funds from NIH, USDA and USAID were used in the development of the present invention (NIH P42-ES04917, USDA Animal Health Grant 9700579, USAID LAG-G-00-96-90013-00, TAES H6215, and NIH Center Grant ES09106).

BACKGROUND

This invention is generally related to clay-based sorbent compositions and methods for decreasing the bioavailability and toxicity/carcinogenicity of toxins, particularly aflatoxins, in systems by sequestering these agents in the gastrointestinal tract (i.e., enterosoprtion). More specifically, an oral composition is described for use as an enterosorbent therapy to mitigate the adverse effects (both acute and chronic) of aflatoxins in human populations at risk for aflatoxicosis and liver cancer. This enhanced risk is due to frequent and high levels of aflatoxin exposure in the diet. The composition contains an effective amount of a processed calcium aluminosilicate clay in a powder form. This processed calcium aluminosilicate clay possesses less than the tolerable daily human intake of tetrachlorodibenzo-p-dioxin (TCDD) and priority toxic metal contamination based on EPA, JECFA and WHO recommendations. The compositions and methods are used as part of an oral treatment. Additionally, the clay of this invention does not interfere with the treated system's or medium's utilization of important vitamins and other micronutrients that are found naturally in the diet. The processed clay of this invention binds aflatoxins preferentially, with high affinity and high capacity in the gastrointestinal tract, resulting in a notable reduction in exposure (based on aflatoxin-specific biomarkers). Decreased exposure to aflatoxins from contaminated diets could reduce the risk of disease and death from these poisons.

Aflatoxins

Introduction:

Concerns about the quality and safety of foods destined for animal and human consumption have evoked a growing awareness of the significant hazards associated with chemicals known as the aflatoxins. In historical context, the aflatoxin problem in foods is longstanding, unavoidable and seemingly inextricable. Aflatoxins (Afs) are harmful by-products of mold growth and are potentially fatal to humans and animals. Importantly, the aflatoxins are heat stable, survive a variety of food processing procedures, and occur as contaminants of most foods (particularly those derived from maize and peanuts). Aflatoxin $B_1$ (Af$B_1$), the most toxic of four naturally occurring aflatoxins (FIG. 1), is a direct acting mutagen and has been shown to disrupt genes involved in carcinogenesis and tumor suppression. It reacts in vivo with DNA to give trans-8,9-dihydro-8-($N^7$-quanyl)-9-hydroxy-aflatoxin $B_1$ as the primary aflatoxin-DNA adduct. Along with hepatitis B virus infection, it has been implicated as a factor in the etiology of hepatocellular carcinoma (HCC). Aflatoxin $B_1$ has also been shown to be immunotoxic and antinutritional. In the U.S., the action level for Afs in foods intended for human consumption has been set to 20 ppb. A recent outbreak of aflatoxin poisoning in Kenya was linked to consumption of foods containing levels as high as 8,000 ppb, indicating a critical need for treatment regimens to alleviate acute aflatoxicosis in populations at high risk for aflatoxicosis.

Occurrence:

Drought is a common cause of fungal infection and enhanced production of aflatoxins. This is especially true in developing countries (40° N and S of the equator), where aflatoxins in the diet of humans and animals are largely uncontrolled. The problem impacts the poorest people, who are most likely to consume foods contaminated with aflatoxins and suffer the consequences, including disease and acute death. Thus, dietary interventions and therapies to alleviate aflatoxicosis in humans and animals are high priorities; the use of dietary montmorillonite clay as an aflatoxin enterosorbent, may provide a practical and cost-effective approach to the problem.

Chemopreventive Strategies that Modulate the Metabolism of Aflatoxin:

Avoiding consumption of aflatoxin contaminated foods can significantly reduce the risk of acute or chronic aflatoxicosis in systems, mediums, or subjects; however, in developing countries, a change in the diet is usually not feasible. One approach to the problem is the strategy of chemoprevention in high-risk populations. This strategy involves the use of natural or synthetic agents to block, retard, reverse or modulate the carcinogenic process. Many chemopreventive agents have been studied and some exist as natural constituents in the human diet such as those found in fruits and vegetables. Several of these have shown efficacy in protection against a wide range of carcinogens; however, most occur at very low levels in a nutritionally balanced diet and they are poorly absorbed in the gastrointestinal tract. Studies have investigated the use of the antischistosomal drug oltipraz as a chemopreventive agent in systems or subjects exposed to dietary aflatoxins in China. In clinical trials, researchers have demonstrated that oltipraz increases the level of glutathione S-transferase mediated conjugation of aflatoxin 8,9-epoxide and also results in the inhibition of cytochrome P450 1A2 activity. Other work has shown that oltipraz may also inhibit hepatitis B virus (HBV) transcription through elevation of p53 providing an additional contribution to HCC chemoprevention. Natural products such as chlorophyllin may also be used to sorb aflatoxins and reduce the amount of toxin reaching the liver. Chlorophyllins are constituents of the human diet that have been found to be effective anti-carcinogens in several animal models. Chlorophyllin is thought to enhance metabolism and act as an interceptor molecule by binding with carcinogens, such as Af$B_1$ thereby diminishing bioavailability. In a clinical trial in China, participants were randomly assigned to two groups, which were given 100 mg of chlorophyllin or a placebo three times a day for four months. Chlorophyllin consumption at each meal led to an overall 55% reduction in median urinary levels of aflatoxin-N7-guanine adducts compared with consumption of the placebo (Egner et al., 2001). The extended use of these compounds in humans would require careful evaluation including long-term effects of enzyme modulation and potential interferences with the uptake of essential nutrients from the diet. Green-tea derived polyphenols are also under investigation as possible interventions for populations at high risk for HCC. These compounds are highly effective chemopreventive agents against cancer at different organ sites in various animal models. Research has indicated that green tea inhibits the initiation of $AfB_1$-induced hepatocarcinogenesis in the rat by modulation of $AfB_1$ metabolism. Additional studies with B6C3F1 mice have shown that the administration of green tea (3% in water) prevented the hepatic focal lesion growth induced by dieldrin. Green tea co-treatment also resulted in an increase in the apoptotic index in mouse liver focal lesions. In humans, inverse associations between the level of green-tea consumption and the risk of development and/or time of cancer onset have also been observed.

Dietary Clay Interventions that Reduce the Bioavailability of Aflatoxins:

The consumption of clays (geophagy) has been recorded from traditional human societies for centuries and is "culturally acceptable" in Africa and China. Using multiple animal models, our laboratory has shown that calcium montmorillonite clays can be effective in preventing the adverse effects of dietary aflatoxins. The strategy of reducing foodborne exposure to mycotoxins via the inclusion of various binding agents or sorbents in the diet has been given considerable attention. As early as 1979, adsorbent clay minerals were reported to bind aflatoxin $B_1$ in liquids. Also, bleaching clays, that had been used to process canola oil, were found to lessen the effects of T-2 toxin.

HSCAS Enterosorbent Interventions for Aflatoxins in the Diet:

In the first enterosorbent study with aflatoxins, HSCAS (HSCAS™), a calcium montmorillonite clay that is sold as an anticaking additive for animal feeds, was reported to sorb aflatoxin $B_1$ with high affinity and high capacity in aqueous solutions and rescued broiler and Leghorn chicks from the toxic effects of 7,500 ppb of aflatoxin in the diet. Since these early studies, HSCAS and other similar montmorillonite and bentonite clays have been reported to diminish the effects of aflatoxins in a variety of young animals including rodents, chicks, turkey poults, ducklings, lambs, pigs, mink and trout. HSCAS has also been shown to decrease the bioavailability of radiolabeled aflatoxins and reduce aflatoxin residues in poultry, rats and pigs (FIG. 2). Levels of aflatoxin $M_1$ in milk from lactating dairy cattle and goats were also diminished with the inclusion of HSCAS in the diet.

Molecular Mechanisms and Thermodynamics for the Sorption of Aflatoxins to HSCAS:

Insight into the adsorption of $AfB_1$, onto the surfaces of HSCAS came from the observation that stereochemical differences between some of the aflatoxin analogs resulted in a significant effect on the tightness of binding (even though the carbonyl functional groups were identical). These results also suggested that the molecular mechanism for the adsorption of aflatoxins onto HSCAS may favor an optimal orientation where the furan is aligned away from the surface. $AfB_1$ is strongly bound to HSCAS based on the thermodynamics of the sorption and an estimated heat of sorption (enthalpy) of −40 kJ/mol. A potential chemical reaction that may explain these results is an electron donor acceptor (EDA) mechanism. This mechanism involves sharing of electrons from the negative surface of the clay with atoms in the adsorbed molecule that are partially positive. The carbons comprising the dicarbonyl system in aflatoxins are partially positive (electron poor) and have also been shown to be essential to the adsorption process. When the summation of partial charges of the carbons of the carbonyl functional groups for each ligand was plotted versus binding strength, there was a significant correlation. When the ligands that were not planar on the side of the molecule opposite the dihydrofuran functional group were removed from the set of test compounds, the correlation was significantly improved. Interference from compounds with stereochemical restrictive groups could also play an important role in the adsorption process. For the analogs that contain functional groups that make them larger than $AfB_1$, their insertion, docking and adsorption at clay surfaces, separating interlayer channels, might be restricted.

Specificity of HSCAS for Aflatoxins:

Research has supported the conclusions that HSCAS has a notable preference (and capacity) for the aflatoxins at levels in the diet at, or below, 0.5% w/w (the level that is recommended for anticaking activity in animals feeds). For example, HSCAS at a level of 0.5% in the diet of poultry, did not impair phytate or inorganic phosphorous utilization. In other poultry nutrition studies, the addition of HSCAS at concentrations of 0.5% did not impair the utilization of riboflavin, vitamin A, manganese, or zinc. Also, in earlier studies, HSCAS (at an inclusion rate of 0.5%) has been shown to protect young chickens from very high levels of aflatoxins (i.e., 7,500 ppb). While clay-based interventions are clearly effective for aflatoxins, an analogous technology is not yet available for other important mycotoxins. For the most part, unmodified NS clays do not "tightly" bind other structurally diverse mycotoxins, e.g., zearalenone, deoxynivalenol, T-2 toxin, ochratoxin A, cyclopiazonic acid, ergotamine, and fumonisins, nor do they significantly prevent the adverse effects of these mycotoxins when included in the diet of animals. For example, in enterosorbent studies in poultry with mycotoxins (other than the aflatoxins), the inclusion of HSCAS in the diet did not significantly prevent the adverse effects of cyclopiazonic acid, T-2 toxin, diacetoxyscirpenol, ochratoxin A, and fumonisins. The use of clay in mink fed zearalenone helped to alleviate some fetotoxicity but did not reduce the hyperestrogenic effects. Also, the addition of clay at 0.5 and 1.0% w/w in the diet, did not influence the average daily weight gain of pigs exposed to deoxynivalenol. The only effective method for decreasing the toxicity of deoxynivalenol in this study was the dilution of the contaminated maize with uncontaminated maize. The possibility of supplementing livestock diets with HSCAS to prevent fescue toxicity has also been investigated. Although in vitro experiments predicted good binding of ergotamine to montmorillonite clays in aqueous solution, HSCAS (at levels of 2.0% by weight) did not protect rats or sheep from fescue toxicosis. In order to further confirm the specificity of HSCAS for $AfB_1$, protocols were developed to nanostructure thin films of the HSCAS onto the surface of quartz and use the resulting composite as an affinity probe for aflatoxins in contaminated media. Our findings suggested that this composite media (when packed in small glass cleanup columns) was comparable in selectivity to the Aflatest affinity column from VICAM.

Chronic Animal Study with HSCAS:

In initial short-term animal studies with HSCAS, no observable adverse effects were reported following ingestion of clay in the diets. A more recent study in which Sprague-Dawley (S-D) rats ingested HSCAS at dietary concentrations as high as 2.0% throughout pregnancy showed neither maternal nor fetal toxicity, and also did not show significant trace metal bioavailability in a variety of tissues. A rodent model was also used to evaluate the relative safety of chronic exposure to HSCAS via the diet. The study involved male and female Sprague-Dawley rats which were fed rations containing 0, 0.25, 0.5, 1.0, and 2.0% levels of NS clay ad libitum over a 6.5-month period. The results of this study indicated that rats treated with 0.25-2% NS clay in the diet did not exhibit dose-dependent or HSCAS-related adverse effects on body weight gains, feed conversion ratios, relative organ weights, gross anatomy and histological appearance of major organs; hematology, and serum biochemistry parameters. Additionally, levels of selected essential nutrients including vitamins A and E, Fe, and Zn were unaffected. These findings suggested that enterosorbent therapy or dietary intervention with HSCAS may be a potential option for the management of aflatoxicoses in high-risk human populations.

Adverse Events Trial with HSCAS in Systems or Subjects:

Following the chronic rodent study, a two-week short-term safety evaluation of HSCAS was carried out in healthy human volunteers. This phase I Adverse Events trial was designed to determine short term safety and tolerance of HSCAS in subjects. Prior to encapsulation, HSCAS was analyzed for concentrations of various environmental contaminants, including dioxins/furans and heavy metals to insure compliance with federal and international standards (Table 1). For example, the amount of heavy metal contamination in a derived dose of HSCAS is less than the Joint FAO/WHO Expert Commission on Food Additives (JECFA) criteria. More specifically, a derived dose equal to 3 g of HSCAS/day for Co, Cr, Zn, Mo, Se, Ni, Hg, Pb, Cd, As, and dioxins (TCDD and OCDD) is below JECFA criteria.

HSCAS was sterilized at 121° C. prior to packaging into capsules. The HSCAS capsules were produced under sterile conditions using U.S. Good Manufacturing Practices. In the human study, the overall design followed the guidelines for a randomized and double blinded phase I clinical trial. A total of 50 adults who met the recruiting standards were voluntarily enrolled in the study. They were randomly divided into two study groups. The low dose group took three capsules of HSCAS (0.5 g) three times a day for two weeks. The high-dose group took three capsules of HSCAS (1.0 g) three times a day for two weeks. All capsules were of the same color and size. The two dose levels were extrapolated from previously published animal studies. Results indicated that both doses of HSCAS used in this study were tolerable for all study participants. Gastrointestinal adverse effects were noticed in some subjects, 24% (6/25) in the 1.5 g group and 28% (7/25) in the 3.0 g group. Symptoms included bloating, constipation, diarrhea, flatulence, and abdominal discomfort. Two participants in the low-dose (1.5 g HSCAS) group reported experiencing some degree of dizziness, an effect which was not evident in the high-dose (3.0 g NS) group. All symptoms described were recorded in the first 2-days after taking the NS capsules and no symptoms (or complaints) were recorded thereafter. All side-effects reported, except from one participant, were assessed to be mild, and no significant difference between the two treatment groups was observed. Results of this study showed that administration of HSCAS capsules at 1.5-3.0 g/day to healthy human subjects for 14 days was relatively safe, as demonstrated by the analysis of biochemical and hematological parameters, as well as physical examinations. It has been postulated that some clay minerals may sorb vitamins; however, in this study no statistical differences were observed in the levels of serum vitamins A and E after treatment with either dose of HSCAS. This evidence further confirms that HSCAS demonstrates binding specificity for AFs and lack of interaction with vitamins A and E. No significant differences were found in levels of the majority of minerals analyzed, with two exceptions: lower inorganic sulfur concentration in the low-dose group and higher strontium concentrations in both groups. The clinical significance of these findings is not yet known and will be monitored in future intervention studies.

Aflatoxin Carcinogenicity:

Human hepatocellular carcinoma (HCC) is one of the most common cancers worldwide and the leading cause of death in parts of China and Africa, where chronic infection with hepatitis B virus (HBV) and exposure to aflatoxins in the diet are considered the main etiological factors. In more developed countries, adequate food supplies combined with regulations that monitor these aflatoxin levels in foods, offer a means of protection and reduced exposure in human populations. In countries where starvation is endemic and food quality regulations are unavailable, daily exposure to aflatoxins substantially increases the risk of HCC and other adverse human health effects. In many of these cases disposal and/or substitution of mycotoxin-contaminated foodstuffs is not a viable option. Unfortunately, such realities of life still exist in the 21st century and highlight the importance of reducing or eliminating the dietary exposure to aflatoxins in order to improve the health status and quality of life in these high-risk human populations. Aflatoxins are difuranocoumarin derivatives produced by many strains of *Aspergillus flavus* and *Aspergillus parasiticus*; in particular, *A. flavus* is a common contaminant in agriculture. These toxigenic fungal species are distributed throughout the world, and are more prevalent in warm, sub-tropical and tropical climates in comparison with temperate environments. Natural contamination of cereal grains, oilseeds, nuts, fruits, tobacco, and a wide range of other commodities is a common occurrence. Of the four major aflatoxin congeners produced by *Aspergillus* sp., ($B_1$, $B_2$, $G_1$, and $G_2$), aflatoxin B1 ($AfB_1$) is the most potent hepatocarcinogen and has the greatest human health significance. The liver is the primary site of biotransformation of ingested aflatoxins. Initially, $AfB_1$ undergoes an oxidation by cytochrome P450 CYP1A2 and CYP3A4, yielding two aflatoxin-8,9-epoxide stereoisomers. The exo epoxide, a highly reactive intermediate, reacts with the N7 atom of guanine to form a promutagenic DNA adduct, $AfB_1$—$N^7$-guanine. This aflatoxin-DNA adduct is unstable and undergoes depurination leading to its excretion in urine. The exo epoxide is also capable of binding to lysine residues in serum albumin, as well as other cellular proteins. CYP1A2 also catalyzes the hydroxylation of $AfB_1$ to yield $AfM_1$, which is a major aflatoxin metabolite in humans and other oxidation products such as $AfP_1$, and $AfQ_1$. These metabolites can be excreted without further biotransformation or they can be conjugated by UDP-glucuronosyl transferases, however, $AfM_1$ is not a substrate for glucuronidation. The aflatoxin-8,9-epoxide intermediate is also a substrate for glutathione-5-transferases, which produce a stable, nontoxic, polar product excreted in the bile. The aflatoxin-glutathione product undergoes further sequential metabolism in the liver and kidneys to be excreted as a mercapturic acid (aflatoxin-N-acetylcysteine) in the urine. Aflatoxin was initially classified as a human carcinogen by the International Agency on Research in Cancer in 1993, and further epidemiological and experimental research continues to provide evidence of a strong link between aflatoxin exposure and HCC. In the Peoples Republic of China alone, HCC accounts for more than 200,000 deaths annually and is the third leading cause of cancer mortality. In particular, HCC is the leading cause of cancer death in Qidong, a city in eastern Jiangsu Province, People's Republic of China, and accounts for up to 10% of all adult deaths in some of the rural townships. Early evidence associating aflatoxin exposure to HCC was based largely on estimates of aflatoxin ingestion as measured in contaminated food or from dietary questionnaires. Further studies have relied on the measurement of various biomarkers in the urine and blood as a more accurate means of correlating aflatoxin exposure with the occurrence of HCC. The urinary AFB—$N^7$ guanine adduct has been used in many $AfB_1$ studies in mediums, systems, or subjects, as a quantitative indicator of exposure to aflatoxin. $AfM_1$ is a major urinary metabolite excreted following $AfB_1$ ingestion and may also be used as a linear biomarker of aflatoxin exposure. In addition, the aflatoxin-albumin adduct in serum has been used for longer term exposure estimates. The availability and application of these aflatoxin-specific biomarkers has helped to better characterize human exposure and susceptibility to aflatoxins in high risk populations. For example, nested case-control biomarker studies conducted in Shanghai in the early 1990s showed a significant link between aflatoxin exposure and HCC as well as a dramatic sixty-fold increase in the risk of liver cancer when aflatoxin exposure was concomitant with chronic hepatitis B infection. Subsequent studies in Taiwan and Qidong have confirmed these findings.

U.S. Pat. No. 5,178,832, issued to Phillips, et al., on Jan. 12, 1993, and titled "Selective Immobilization and Detection of Mycotoxins in Solution" describes how certain minerals, particularly various naturally occurring forms of aluminum oxide, will preferentially bind selective mycotoxins from a mixture of mycotoxins. These adsorbents, when used in various combinations and/or in conjunction with the adsorbents of the prior art, permit the construction of detector tubes which can resolve mycotoxins in solution and provide a semi-quantitative fluorescent determination of their concentration in feed or foodstuff samples. The detector tubes comprise transparent tubes packed with isolated layers of selected minerals. A solvent extract from a sample potentially contaminated with mycotoxins is passed through the column. As the mycotoxin mixture passes through the detector tube and is contacted by the various mineral adsorbents, selected mycotoxins are immobilized on a specific mineral while other mycotoxins and co-extracted organic compounds pass through that layer to be immobilized on subsequent downstream mineral layers. The presence of mycotoxins is determined by examining the developed detector tube under a long wave UV light source.

U.S. Pat. No. 5,165,946 issued to Taylor, et al., on Nov. 24, 1992, titled "Animal Feed Additive and Method for Inactivating Mycotoxins Present in Animal Feeds," describes a dry solid animal feed composition capable of inactivating mycotoxins. When feed was contaminated with mycotoxin and was admixed with a mycotoxin inactivating agent comprising particles of a phyllosilicate mineral capable of inactivating mycotoxins, the composite material enhanced the mycotoxin inactivating capacity of the phyllosilicate.

Clay as a Treatment for Aflatoxins.

The clay-based composition of this invention can be used to bind and treat exposure to environmental toxins, treat acute aflatoxin poisoning and prevent aflatoxin induced liver cancer and chronic aflatoxicosis. However, one of ordinary skill in the art will recognize that there are many different types of clay, and clay uses and applications have been well-documented throughout human history.

Clay is a generic term for an aggregate of hydrous silicate particles. Generally, clay consists of a variety of phyllosilicate minerals generally rich in silicon and aluminium oxides, and hydroxides. Clays are distinguished from other small particles present in soils such as silt by their small size, flake or layered shape, affinity for water and high plasticity index. Main groups of phyllosilicate clays include kaolinite, montmorillonite-smectite, illite, and chlorite.

Montmorillonite clay is typically formed as a weathering product of low silica rocks. Montmorillonite is a member of the smectite group and a major component of bentonite.

Varve (or varved clay) is clay with visible annual layers, formed by seasonal differences in erosion and organic content. This type of deposit is common in former glacial lakes from the ice age.

Quick clay is a unique type of marine clay, indigenous to the glaciated terrains of Norway, Canada, and Sweden. It is a highly sensitive clay, prone to liquefaction which has been involved in several deadly landslides.

Other names for clay include: HSCAS, Akipula, aluminium silicate, anhydrous aluminum silicates, askipula, beidellitic montmorillonite, benditos, bioelectrical minerals, cipula, chalk, clay dirt, clay dust, clay lozenges, clay suspension products, clay tablets, colloidal minerals, colloidal trace minerals, fossil farina, humic shale, Indian healing clay, kaolin, kipula, mountain meal, panito del sensor, plant-derived liquid minerals, tirra santa, Terra sigillata, white clay, white mud, etc.

Medicinal Uses of Clay.

Today, clay is used in many industrial processes to make bricks, cooking pots, art objects, dishware, sparkplug bodies, cement production and chemical filtering. According to folklore, eating clay has many medicinal purposes, but the scientific literature indicates that ingesting certain clays may be harmful to the consumer. The chemical nature of clays may allow them to sorb a variety of potentially detrimental agents. For example, clay pots containing candy (Jarritos brand Tamarindo candy) have been recalled in the United States by the Food and Drug Administration due to high levels of lead in the candy that was derived from the clay pots. Clay products may contain varying amounts of aluminum, arsenic, barium, lead, nickel, titanium and other trace metals. Additionally, elevated levels of 2,3,7,8-tetrachlorodibenzo-p-dioxin have been found in farm-raised catfish and eggs from chickens fed a diet including ball clay from a mine in Mississippi. Additionally, chronic clay eating may be associated with trace element deficiency. However, it should be pointed out that the group of clays used predominantly in the ceramics industry and consumed by systems or subjects are the kaolinites (Ball clays).

Therefore, clays (especially kaolinites) that are ingested by humans should not have elevated levels of toxic agents. The processed clay of this invention can be used to treat or prevent aflatoxin toxicity. Although clay has been used medicinally for centuries in Africa, India, and China, and by Native American groups, one of ordinary skill in the art understands there is a potential for severe adverse effects with chronic oral ingestion of certain clays. As described below, the scientific and medical communities believe these adverse effects may outweigh any potential benefits.

The practice of eating dirt, clay, or other non-nutritious substances may be referred to as "pica" or "geophagia," and is common in early childhood and in mentally handicapped or psychotic patients. There is some evidence that mineral deficiencies such as iron deficiency may lead to pica, and prevalence is higher in developing countries and in poor communities. Chronic clay ingestion may lead to iron malabsorption and further precipitate this condition. There is insufficient scientific evidence to recommend for or against the use of clay for any medical condition. The potential for adverse effects with chronic oral ingestion of clay may outweigh any potential benefits.

Clay products may contain varying amounts of aluminum, arsenic, barium, lead, nickel, titanium and other trace metals. Certain colloidal mineral supplements may also contain unsafe concentrations of radioactive metals. Ingestion of certain clays is possibly unsafe when used in patients during pregnancy or lactation, or when used in children. Some clays may possess potassium-binding capacity, and chronic ingestion of these clays has been associated with severe hypokalemia, particularly in patients with renal insufficiency. It has been suggested that habitual eating of kaolinic clays (pica or geophagia) may lead to iron malabsorption and severe deficiency, and may be associated with anemia and lead poisoning.

The following physiological problems have reported with "pica" or "geophagia:"

Allergy/hypersensitivity to certain clay, can be characterized by an edematous appearance, dilated cardiomyopathy, polyuria, and death. Additionally, skin dryness, skin ulcerations were noted over the upper and lower extremities of subjects.

Neurologic/CNS:

Pica has been associated with the development of lead poisoning in children, and may carry a risk of central nervous system damage. In one case report, a 6-year-old girl died from complications of lead poisoning and encephalopathy after ingesting lemonade from a glazed clay pitcher. The risk of neurolathyrism, a neurodegenerative, irreversible disorder that cause spastic paraparesis of the body that leads to paralysis, was reported to quadruple in a case-control study in Ethiopia when cooking grass pea with clay utensils.

Psychiatric:

Habitual pica may occur in patients with mental illness, including psychotic disorders.

Pulmonary/Respiratory:

In the 1960s, it was reported that children with a history of pica were predisposed to develop more frequent and severe respiratory infections than healthy children. Chronic bronchitis, dyspnea, and pneumoconiosis have been associated with dust exposure in the heavy clay industry.

Cardiovascular:

Pica was reported to be associated with dilated cardiomyopathy and death.

Gastrointestinal:

Clay eating may precipitate constipation or diarrhea. Heartburn, flatulence, loss of appetite, and vomiting after meals have also been reported. Clay eating has also been associated with intestinal obstruction and necrotizing enteritis, leading to bowel perforation. Colonic stones have been reported in two children with pica. Geophagia has been associated with hepatosplenomegaly.

Renal:

Clay possesses potassium-binding capacity, and chronic clay ingestion has been associated with severe hypokalemia, particularly in patients with renal insufficiency, but not in those receiving hemodialysis.

Endocrine:

Myopathy due to severe hypokalemia has been reported in I case report with large quantities of clay ingestion.

Genitourinary:

Chronic clay eating has been associated with polyuria and urge incontinence, as well as hypogonadism.

Hematologic:

Pica may lead to iron malabsorption and severe deficiency, and has been associated with anemia.

Musculoskeletal:

Myositis has been associated with chronic clay ingestion. Myopathy due to severe hypokalemia has been reported with large quantities of clay ingestion.

Infectious Disease:

Hookworm infections have been associated with ingestion of clay. Tetanus contracted from clay has been described in an infant who ate clay, and in a newborn whose umbilical cord was wrapped in clay.

Iron, Calcium, Magnesium:

Certain clay may act as a cation exchange resin. Calcium and magnesium in these clays can be exchanged with iron, making iron unavailable because of formation of insoluble iron complexes. Iron deficiency may result, and levels of calcium or magnesium may increase.

Potassium:

Certain clays possess potassium-binding capacity, and have been associated with hypokalemia.

One of ordinary skill in the art understands that there is insufficient scientific and clinical evidence in the literature to recommend for or against the medicinal use of certain clays, however, the current illustrations in medicine tend to teach away from using clay as a safe treatment in patients with aflatoxin poisoning, or liver cancer in predisposed subjects. The methods and compositions of this invention utilize isolated clay compositions that are not typically consumed by systems/subjects or used in the manufacture of ceramic eating and drinking utensils. The processed clay of this invention has a particular chemical makeup that does NOT impart adverse health effects when administered orally (based on extensive scientific studies in humans and animals).

SUMMARY

A first aspect of the current invention is an oral composition for use as a preventive therapy to mitigate the effects of environmental toxins, and particularly aflatoxin contaminated foods in subjects who are at risk for developing liver cancer and aflatoxicosis due to high level aflatoxin exposure. The composition comprises an effective amount of a processed calcium aluminosilicate clay in a powder form, wherein the processed calcium aluminosilicate clay contains less than the tolerable daily human intake of tetrachlorodibenzo-p-dioxin (TCDD) and priority toxic metal contamination based on EPA, JECFA and WHO recommendations. Also, the same clay has a high capacity and affinity for the aflatoxins. The processed calcium aluminosilicate clay has a chemical composition comprising: CaO above 3.2%; MgO ranging from 4.0-5.4%; $Fe_2O_3$ ranging from 5.4-6.5; $K_2O$ ranging from 0.50-0.90%; $Na_2O$ ranging from 0.10-0.30%; MnO ranging from 0.01-0.03%; $Al_2O_3$ ranging from 14.8-18.2%; and $SiO_2$ ranging from 62.4-73.5%; wherein, the chemical composition is given as weight percent. The preferred processed calcium aluminosilicate clay has an average particle size that is less than 80 microns and has a pH ranging from 5 to 9.

A second aspect of the current invention is a method of mitigating the effects of foodborne aflatoxins in subjects who are high risk for developing HCC and/or aflatoxicosis. The method comprises (a) administering orally an effective amount of a processed calcium aluminosilicate ("CAS") in a powder form, wherein the CAS contains acceptable levels of TCDD and toxic priority metal contamination, and is capable of binding the aflatoxins; (b) for acute toxicity, waiting a period of time (e.g. less than about 24 hours); and (c) repeating step (a)-(b) until the effects of aflatoxins are mitigated (d) for chronic toxicity, administration of CAS until free of exposure risk to aflatoxins. The preferred CAS has a chemical composition comprising: CaO above 3.2%; MgO ranging from 4.0-5.4%; $Fe_2O_3$ ranging from 5.4-6.5; $K_2O$ ranging from 0.50-0.90%; $Na_2O$ ranging from 0.10-0.30%; MnO ranging from 0.01-0.03%; $Al_2O_3$ ranging from 14.8-18.2%; and $SiO_2$ ranging from 62.4-73.5%; wherein, the chemical composition is given as weight percent. The preferred isolated CAS has an average particle size that is less than 80 microns and a pH ranging from 5 to 9.

The clay-based compositions of the current invention, also referred to as CAS, are capable of mitigating the effects of any environmental toxins, though not as efficiently as aflatoxins.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the chemical structures of predominant aflatoxin congeners.

FIG. 2 shows results of in vivo studies using HSCAS.

DETAILED DESCRIPTION

Figure 3:
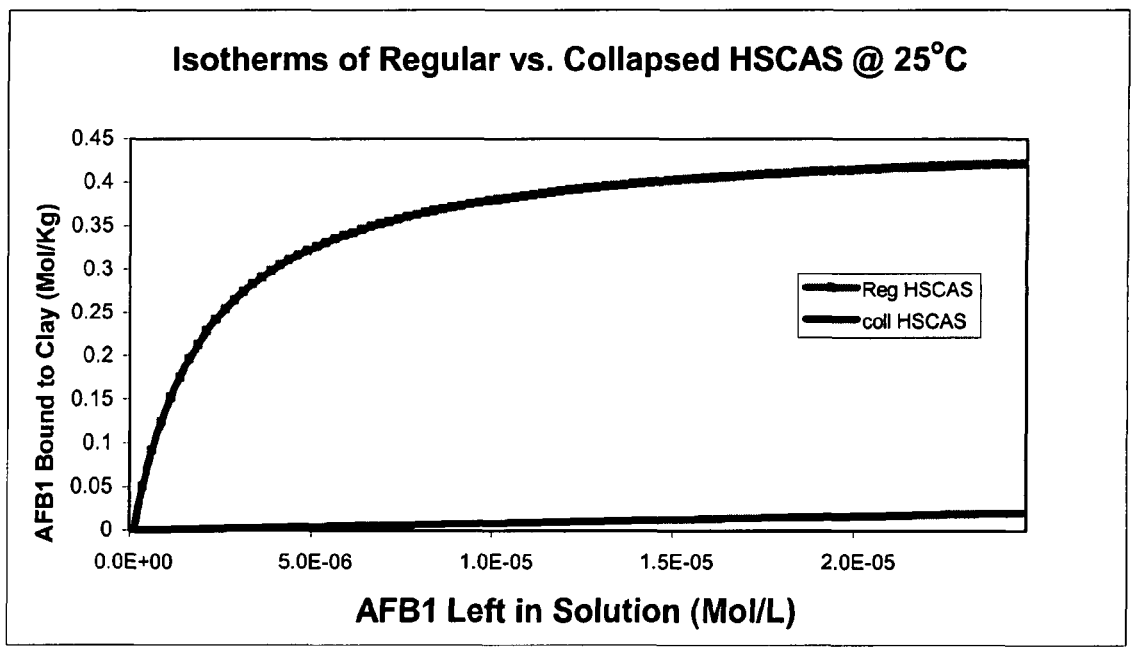
FIG. 3 shows the isotherms of regular vs. collapsed HSCAS.

Before describing the present invention in detail, it is to be understood that this invention is not limited to particular compositions or composition delivery systems, which may vary. It is also to be understood that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a base" includes mixtures of two or more bases, and the like.

In describing and claiming the present invention, the following terminology will be used in accordance with the definitions set out below.

"Active agent," "pharmacologically active agent," "composition," and "drug" are used interchangeably herein to refer to compositions and drugs that are useful for the prevention and treatment of aflatoxin poison and aflatoxin induced liver cancer. The terms also encompass pharmaceutically acceptable, pharmacologically active derivatives and analogs of such drugs, including, but not limited to, salts, esters, amides, prodrugs, active metabolites, inclusion complexes, analogs, and the like. Therefore, when the terms "active agent," "pharmacologically active agent", or "drug" are used, it is to be understood that applicants intend to include the active composition per se as well as pharmaceutically acceptable, pharmacologically active salts, esters, amides, pro-drugs, active metabolites, inclusion complexes, analogs, etc., which are collectively referred to herein as "pharmaceutically acceptable derivatives."

The present invention pertains to compositions and methods of preventing or treating aflatoxin poisoning using an effective amount of clay as an aflatoxin binding agent or sorbent. The aflatoxins are a group of carcinogenic mycotoxins produced primarily by *Aspergillus flavus* and *Aspergillus parasiticus* fungi and are often detected in foods and agricultural commodities. These compounds are heat stable and can survive a variety of food processing procedure; thus aflatoxins can occur as "unavoidable" contaminants of most foods and livestock feeds. Of four naturally occurring aflatoxins ($B_1$, $B_2$, $G_1$, and $G_2$), aflatoxin $B_1$ is the most toxic and has been shown to disrupt genes involved in carcinogenic and tumor suppression. In addition, several studies suggest that low-level exposure to aflatoxins may cause suppression of the immune system and increased susceptibility to disease.

Although not wanting to be bound by theory, no absolute methods are available for totally eliminating mycotoxin contamination in various agricultural commodities; however, clay-based approaches do offer a economical and practical solution for reducing dietary exposure to aflatoxins. Furthermore, the use of dietary aflatoxin enterosorbents and nonspecific binding agents to prevent and treat aflatoxin poisoning is described in the examples below.

The present invention also pertains to compositions and methods of preventing or treating the effects of any environmental toxin using an effective amount of clay as a toxin binding agent or sorbent.

EXAMPLES

The following examples are provided to further illustrate this invention and the manner in which it may be carried out. It will be understood, however, that the specific details given in the examples have been chosen for purposes of illustration only and not be construed as limiting the invention.

Example 1

Several strategies are available for managing aflatoxins in agricultural commodities, the simplest of which requires isolation and destruction of the contaminated source. This approach however, is often not practical since alternative food supplies may not be available, or replacement supplies may not be economically affordable. One of the most promising and well-studied approaches for prevention of aflatoxicoses in livestock involves the incorporation of clays or various "binding agents" into diets contaminated with these toxins. The additives reduce the bioavailability of the toxin in the gastrointestinal tract; that is, they serve as sequestering agents (enterosorbents) of the toxins, thus reducing uptake and distribution to the blood and target organs.

Adsorbent clay minerals have been reported to bind aflatoxin $B_1$ in liquids. In the first enterosorbent study with aflatoxins, a calcium montmorillonite clay that is commonly used as an anti-caking additive for animal feeds has been shown to significantly sorb aflatoxin $B_1$ with high affinity and high capacity in aqueous solutions and to protect broiler and Leghorn chicks from the toxic effects of 7,500 ppb aflatoxins in the diet. Since this initial study, calcium montmorillonite clay and other similar montmorillonite clays have been reported to diminish the toxic effects of aflatoxins in a variety of young animals including rodents, chicks, turkey poults, ducklings, lambs, mink and pigs. Clay in the diet has also been shown to diminish levels of aflatoxin $M_1$ in milk. More recently, urinary biomarkers of $AfB_1$ exposure in dogs were reduced by the inclusion of calcium montmorillonite clay. Thus, CAS at 0.5% (w/w) in the feed protected against the adverse effects of 7,500 ppb aflatoxins in the same feed. This high aflatoxin level would not normally be found as a contaminant of food or feed and (as such) represents a "worst case scenario." Aflatoxin protection can be shown at levels as low as 0.25% (w/w) in the diet. Extrapolating to the human, an approximate 3 g dose of CAS in a capsule would approximate the 0.25% level in food based on food intake data in Ghana and a body weight of 70 Kg.

GRAS Status and Safety Studies for In Vivo Use of Clay.

One of ordinary skill in the art would be aware that scientific publications support the use of calcium montmorillonite clay as an aflatoxin binding agent in animal feeds. A compilation of various in vivo studies involving calcium montmorillonite clay in multiple animal species is described herein (see FIG. 2). For example, hydrated sodium calcium aluminosilicate is generally recognized as safe for use in feeds at a level not exceeding 2 percent in accordance with good manufacturing or feeding practice.

In animal studies with calcium montmorillonite clay, no adverse effects from clay treatment, at levels up to 2.0% in the diet, have been reported. In recent studies in rodents, montmorillonite clays were evaluated for potential toxicity and trace metal bioavailability in pregnant Sprague-Dawley rats throughout the period of gestation following high level exposure in the diet (2.0% w/w). Clays were supplemented in the balanced diet of Sprague-Dawley rats during pregnancy at a level of 2.0% (w/w). Evaluations of toxicity were performed on gestation day 16 and included maternal body weights, maternal feed intakes, litter weights, in addition to embryonic resorptions. Liver and, kidneys, tibia, brain, uterus, pooled placental, and pooled embryonic mass were collected and weighed. Tissue were lyophilized and neutron activation analysis (NAA) was then performed. Elements considered by NAA included: Al, Br, Ca, Ce, Co, Cr, Cs, Cu, Dy, Eu, Fe, Hf, K, La, Lu, Mg, Mn, Na, Nd, Ni, Rb, S, Sb, Sc, Se, Sm, Sr, Ta, Th, Te, Th, Ti, TI, U, V, Yb, Zn, and Zr. Inductively coupled plasma-mass spectroscopy further confined that Al was below detection limits (0.5 ppm) in the brain, indicating no significant bioavailability of this metal from clay interactions in the GI tract. Animals supplemented with either clay were similar to controls with respect to toxicity evaluations and metal analysis, with the exception of decreased brain Rb following clay supplementation. Overall, the results of this study suggest that neither clay at high dietary concentrations, result in overt toxicity or influence mineral uptake or utilization in the pregnant rat. In some embodiments, clay was selected for testing due to its GRAS status and its purity priority trace metals and dioxin levels, see Table 1.

Other studies in rodents and subjects have confirmed the safety of calcium montmorillonite clay for application in human diets. In the rodent study, rats were fed rations containing about 0, 0.25, 0.5, 1.0, and 2.0% levels of calcium montmorillonite clay. Body weights, body weight gain, organ weights, histopathology, plasma biochemistry, serum vitamins A and E and micronutrients (Fe and Zn) were measured, standardized and compared to determine toxicity and any interactions of clay with critical nutrients at the end of the study. After 6 months exposure to clay, no morbidity or mortality was observed among treatment groups. There were no changes in the major organs, serum biochemistry or micronutrient levels. The ratios of organ weight to final body weight for the liver, kidneys, lungs, heart, brain, spleen, and tibia among the treatment groups in each sex were not significantly different histopathological analysis of the liver and kidneys indicated no differences between controls and clay treatments. These results suggest that inclusion of clay at levels less than 2.0% (w/w) in the diet should not result in overt toxicity and can be used safely to reduce exposure to aflatoxins in the gastrointestinal tract. In the human study, calcium montmorillonite clay was initially tested for trace metals and dioxin content in order to confirm the composition of matter and ensure low levels of contamination.

Calcium montmorillonite clay was then heat sterilized and packed into capsules for use in the study. The study design was based on 2 treatment groups: 1) low dose—3×500 mg capsules×3 times/day for a total of 2 weeks, and 2) high dose—3×1,000 mg capsules×3 times/day for a total of 2 weeks. The 2-week trial consisted of 50 healthy adults, age 22-40 selected by initial physical exams, laboratory analysis of biological fluids and questionnaire. One of ordinary skill in the art would be able to make capsules that are modified from the above description, that varied in dose, see Remmington's Pharmaceutical Sciences $17^{th}$ Edition. Participants were then given clay capsules before meals with a bottle of spring water. Medical personnel were onsite to monitor any complaints or adverse effects. Blood and urine samples were taken at the end of the 2 week period and laboratory analysis and physical examinations were administered again. Any adverse events were reported according to NIH guidelines. Compliance with the dosing protocol reached 100% over the two-week study period. Analysis of clinical and biochemical data for side effects monitoring, blood, and urine parameters for liver and kidney function did not show any specific adverse effects.

Mode of Action and Mechanistic Studies.

Several in vitro studies have assessed the sorption of aflatoxins onto the surface of hydrated sodium calcium aluminosilicate clay (HSCAS). HSCAS, in aqueous solution, has been shown to tightly and preferentially sorb $AfB_1$ and similar analogs of aflatoxin $B_1$ ($AfB_1$) that contain an intact β-dicarbonyl system in their molecular structure. Isothermal analysis of $AfB_1$, sorption to HSCAS indicated both high affinity and high capacity characteristics and also suggested that different sites and/or mechanisms of action may be involved in $AfB_1$ sorption at clay surfaces. The enthalpy of $AfB_1$ sorption (near ~40 kJ/mol) showed some variation, suggesting multiple sites on HSCAS with dissimilar thermodynamic properties. These findings indicate that multiple sites on the surface of HSCASs may act to chemisorb $AfB_1$ and that the optimal orientation of the $AfB_1$ molecule is most likely planar on interlayer clay surfaces. Functional groups on aflatoxin analogs may sterically hinder sorption at the surface of HSCAS or may block sorption by interacting across the interlayer region. Other mechanisms of $AfB_1$ sorption to HSCAS surfaces may involve the potential chelation of predominant interlayer cations such as calcium and various other edge-site metals.

Ingredient Description and Profile.

Calcium aluminosilicate clay (CAS) has a different composition from hydrated sodium calcium aluminosilicate (HSCAS) clay, which has a dark tan color. The CAS has the appearance of an offwhite to gray-greenish colored free flowing powder. The CAS is odorless having a specific gravity of about 2.4. The isolated CAS is negligibly soluble in water and has a pH in the range of about 5-9. Due to the silica and aluminum silicate components, the isolated CAS may have some adverse effects if dry particles are inhaled, but no adverse health effects are suspected from ingestion. The typical values are as follows:

Typical Physical Properties:

| | |
|---|---|
| Free Moisture (LOD) | 9% |
| Loose Bulk Density | 0.64 g/cc 40 lbs/ft3 |
| Packed Bulk Density | 0.80 g/cc 50 lbs/ft3 |
| Particle Size Distribution: | 5% + 100 mesh |
| | 18% + 200 mesh |
| | 60% + 325 mesh |

Typical Chemical Analysis:

| | |
|---|---|
| Chemical Analysis by X-Ray Fractionation (XRF) Spectroscopy (weight %): | % CaO 3.2-4.8 |
| | % MgO 4.0-5.4 |
| | % $Fe_2O_3$ 5.4-6.5 |
| | % $K_2O$ 0.50-0.90 |
| | % $Na_2O$ 0.10-0.30 |
| | % MnO 0.01-0.03 |
| | % $Al_2O_3$ 14.8-18.2 |
| | % $SiO_2$ 62.4-73.5 |

Additionally, testing of the processed clay products from Engelhard's (now BASF), Jackson, Miss. plant have confirmed low levels of TCDD in CAS (<0.33 parts per trillion, ppt). TCDD is given in Engelhard (BASF) specifications as an index of the presence of dioxins in food ingredients.

Analytical Procedures and Methods for Isothermal Adsorption Analysis.

Isothermal Adsorption analysis was performed using a stock solution of aflatoxin $B_1$ ($AfB_1$) which is prepared by dissolving pure $AfB_1$ crystals (Sigma Chemical Co., St. Louis, Mo.) in acetonitrile. A volume of the stock solution is then injected into purified (deionized) water, yielding an 8 μg/mL working solution of $AfB_1$. The working solution's concentration is then verified with a UV-vis spectrophotometer ($\lambda_{max}$=362 nm; $\epsilon$=21,865). The batch isotherm procedure entails the exposure of samples containing 100 μg of sorbent to an increasing concentration of solute ($AfB_1$)(0.4, 0.8, 1.6, 2.4, 3.2, 4, 4.8, 6, 6.4, 7.2, and 8 μg/mL). This study uses three replicates at each solute concentration. The solute concentration is achieved by adding an appropriate amount of working $AfB_1$ solution to sterile 17×100 mm polypropylene centrifuge test tubes and then adding a complementary amount of purified water to bring the total volume to 5 mL/tube. Approximately 10 mg of sorbent is weighed in a 16×125 mm disposable borosilicate glass test tube, and purified water is added to the sorbent to make a 2 mg/mL suspension. This sorbent/water suspension is vortexed for 3 s before each 50 μL transfer to each replicate by an autopipetter. The mixing is repeated before each transfer. Along with the samples, there are three controls consisting of 5 mL of purified water, 5 mL of $AfB_1$ working solution without sorbent, and 5 mL of the lowest concentration of $AfB_1$ without sorbent. The samples and controls are capped and placed on an electric orbital shaker at 1,000 rpm for 24 h in an incubator at either 15, 25, or 37° C. After shaking, the samples are centrifuged at 10,000 rpm for 15 min at the same temperature that the shaking occurred. The UV-vis absorption of $AfB_1$ remaining in the supernatant from the samples and controls is measured with a spectrophotometer. At the highest $AfB_1$ concentration level, the supernatant is saved for analysis by HPLC to check for any degradation compounds since the adsorption calculations are dependent on a different calculation.

Data Calculations and Curve Fitting.

The UV-vis absorption data are used to calculate the amount of $AfB_1$, left in solution and the amount adsorbed for each data point. Using TableCurve 2D software (Systat Software Inc., Richmond, Calif.) these data are fit to the Langmuir isotherm equation:

$$q = Q_{max} \times \left( \frac{K_d \times C_w}{1 + K_d \times C_w} \right)$$

where q is the amount of $AfB_1$ adsorbed, $Q_{max}$ is the maximum amount of $AfB_1$ adsorbed, $C_w$ is the equilibrium concentration of $AfB_1$ in solution and $K_d$ is the distribution constant. The Langmuir equation is entered into the TableCurve 2D program as a user-defined function and has limits and first approximations for variable parameters. The parameter limits for $Q_{max}$ are positive numbers ranging from 0 to a maximum of 1 mol/kg. Parameter limits for $K_d$ range from 0 to $1\times10^{25}$. Starting estimates for the parameters $Q_{max}$ and $K_d$ are determined by TableCurve 2D. After these values are entered into the Langmuir user-defined function in TableCurve 2D, the data is fit, and theoretical values for $Q_{max}$ and $K_d$ are obtained. The $\Delta H_{ads}$ (enthalpy of adsorption) is calculated by comparing the individual $K_d$ values at 15, 25, and 37° C. by the equation:

$$\Delta H_{ads} = \frac{-R \ln(K_{d2} / K_{d1})}{(1/T_2) - (1/T_1)}$$

The definition of $K_d$ is derived by solving for $K_d$ from the Langmuir equation giving:

$$K_d = q/(Q_{max} - q)C_w$$

The $Q_{max}$ is taken from the fit of Langmuir equation to the adsorption data at 15, 25, and 37° C.

Methods for COLE Index.

A measure of expansive properties, the coefficient of linear extensibility (COLE) index is the ratio of the volume of a soil after wetting to the volume of soil before wetting minus one. COLE=(volume of clay after wetting/volume of clay before wetting)−1. COLE index values greater than 0.03 indicate that significant smectite (swelling clay) is present in the sample. The general procedure can be summarized as follows:

1. Add 5 mL (5 $cm^3$) of dry clay to a 25 mL graduated cylinder.

2. Add distilled water to the clay bringing the total volume to 25 mL.

3. Shake or stir suspension vigorously to ensure thorough wetting of clay.

4. Allow suspension to stand for 24 hr. at room temperature.

5. Measure the expanded volume of settled clay.

Shrink-swell potential correlates closely with the kind and amount of clay. The greatest shrink-swell potential occurs in soils that have high amounts of 2:1 lattice clays, such as smectites. Illitic clays are intermediate, and kaolinitic clays are least affected by volume change as the content in moisture changes. Adsorption isotherms of regular vs. heat collapsed HSCAS at 25° C. are shown in FIG. 3.

Example 2

Primary hepatocellular carcinoma (HCC) has unique geographic, sex, and age distributions which are likely determined by specific etiologic factors (i.e. hepatitis and aflatoxin exposure). The incidence of HCC varies widely according to geographic location. The distribution of HCC also differs among ethnic groups within the same country, and between regions within the same country.

High incidence regions (more than 15 cases per 100,000 population per year) include sub-Saharan Africa, the People's Republic of China, Hong Kong, and Taiwan. Over 40 percent of all cases of HCC occur in the People's Republic of China, which has an annual incidence of 137,000 cases. In contrast, North and South America, most of Europe, Australia and parts of the Middle East are low incidence areas with fewer than three cases reported per 100,000 population per year. However, the incidence in the United States has increased during the past two decades, possibly due to a large pool of people with longstanding chronic hepatitis C.

Males are far more likely to develop HCC than females, and the disparity is more pronounced in high incidence regions, where males are affected 2.1 to 5.7 times more frequently than females (mean 3.7:1). The ratio decreases to a mean of 2.4:1 in intermediate incidence areas, and is lower in low incidence regions. Although not fully understood, these differences in sex distribution are thought to be due to variations in hepatitis carrier states, exposure to environmental toxins, and the trophic effect of androgens.

The majority of HCCs occur in patients with chronic liver disease or cirrhosis. Thus, older patients with longstanding liver disease are more likely to develop HCC. Several large prospective studies conducted in both Asia and western Europe have noted a mean age at presentation between 50 and 60 years. In sub-Saharan Africa, however, the mean age of presentation of HCC is decreasing, with a mean age of 33 years at presentation.

Efforts to understand the unique distribution of HCC have augmented our understanding of the risk factors for the development of this disease. Thus, a variety of important risk factors for the development of HCC have been identified. These include the hepatitis B carrier state, aflatoxins, chronic hepatitis C virus (HCV) infection, hereditary hemochromatosis, and cirrhosis of almost any cause. However, HCC can also occur in patients without known risk factors. The role for surveillance in any of these disorders is discussed separately.

Hepatitis B Carrier State.

The association between the hepatitis B carrier state and hepatocellular carcinoma has been demonstrated in several large population based studies and in other reports. In one report, for example, 22,707 male government employees in Taiwan, 15 percent of whom were HBV carriers (hepatitis B surface antigen positive), were followed between 1975 and 1978. The relative risk of HCC in these HBsAg carriers was 223 times that of noncarriers. In another series, the relative risk of HBsAg was 6.9 among 917 Japanese patients with cirrhosis or chronic hepatitis.

Aflatoxins.

Aflatoxin may contribute to the pathogenesis of HCC. Aflatoxin is a mycotoxin that commonly contaminates corn, and peanuts. High rates of dietary aflatoxin intake have been associated with HCC. As an example, the Penghu Islets in Taiwan have an extremely high incidence of HCC which is not entirely accounted for by the HBV carrier state. In a study in which 20 patients with HCC from this region were compared to 86 age-matched controls, the patients were more likely to have aflatoxin $B_1$-albumin adducts (65 versus 37 percent; adjusted odds ratio 5.5); 94 percent of the patients were HBsAg carriers. In another study from Shanghai, the odds of developing HCC among individuals with HBV and exposure to aflatoxin was 59.4 times the normal population incidence.

Mutations of the p53 tumor suppressor gene have been demonstrated in patients with hepatocellular carcinoma who have been chronically exposed to aflatoxin. Similar findings also have been demonstrated in animal models for hepatocarcinogenesis in which p53 mutations have been observed in laboratory animals exposed to HBV and aflatoxins. The potentiating effect of these risk factors has also been demonstrated in transgenic mice that express hepatitis B surface antigen; in one study, some of these mice were bred to lack one of the p53 alleles and/or were exposed to aflatoxin. At 13 months of age, high-grade HCC developed in all seven mice with each of the three risk factors compared to 62 percent of mice with both p53 alleles even though they were exposed to aflatoxin and 25 percent of mice lacking one p53 allele, but not exposed to aflatoxin.

Consuming aflatoxins that are established causative agents for HCC is risky. However, many citizens of the world having low socioeconomic means usually have a choice between ingesting the contaminated food, or not eating at all. Given this choice, the risk of possible HCC outweighs starvation and certain death.

One aspect of the current invention is a method of mitigating the effects of aflatoxins in persons predisposed to HCC by administering orally an effective amount of an isolated low sodium, calcium aluminosilicate clay in a powder form, tablet, or capsule at least once per day, preferably before, during, or after each meal. The isolated low sodium, calcium aluminosilicate clay is substantially free from dioxins and toxic heavy metal contamination, and is capable of binding aflatoxins. In a preferred embodiment, the isolated low sodium, calcium aluminosilicate clay has a chemical composition comprising: CaO above 3.2%; MgO about 4.0-5.4%; $Fe_2O_3$ about 5.4-6.5; $K_2O$ about 0.50-0.90%; $Na_2O$ about 0.10-0.30%; MnO about 0.01-0.03%; $Al_2O_3$ about 14.8-18.2%; and $SiO_2$ about 62.4-73.5% as a weight percent. Additionally, in a preferred embodiment, the isolated calcium aluminosilicate clay has an average particle size that is less than about 80 microns. However, a nominal 200 mesh particle size was chosen for uniformity and purity. These characteristics were desirable in order to investigate and compare the sorption of aflatoxins onto the surfaces of diverse clays and to delineate the thermodynamics and kinetics of the process. One of ordinary skill in the art will recognize that clay minerals are structurally and chemically diverse. Many are ineffective and/or nonselective for the aflatoxins. The CAS of this invention has been evaluated to contain: (a) acceptable thermodynamic characteristics of ligand sorption; (b) acceptable levels of priority metals and dioxins/furans; (c) efficacy in multiple animals species; (d) safety in long-term studies; (e) and negligible interactions with vitamins and micronutrients.

Example 3

Aflatoxins (AFs) are harmful by-products of mold growth produced primarily by the fungi *Aspergillus flavus* and *A. parasiticus*. The naturally occurring AFs (e.g. $B_1$, $B_2$, $G_1$, and $G_2$) have been characterized as hazardous contaminants that occur either separately or concurrently in a variety of foods consumed by humans and animals. Aflatoxin $B_1$ ($AFB_1$) has been characterized as genotoxic, immunotoxic and hepatocarcinogenic. Humans and animals with acute aflatoxicosis typically experience symptoms including jaundice, low-grade fever, GI bleeding, edema, depression, anorexia, diarrhea, fatty liver, ascites, abdominal pain and, potentially, liver failure and death based on dose. Previous reports have revealed a strong dose-response relationship between exposure to AFs and growth impairment, particularly stunting (a reflection of chronic malnutrition) and underweight (an indicator of acute malnutrition), as seen among children in Benin and Togo, West Africa.

One of the most severe outbreaks of acute AF poisoning occurred recently in Kenya (East Africa) and was linked to the consumption of meals prepared from locally grown and poorly stored maize contaminated with AFs at levels as high as 8,000 ppb. The outbreak claimed 125 lives, about 39.4% of the 317 cases reported from January to 20 Jul. 2004. Previous reports have also indicated that AF contamination of foods intended for humans, particularly maize and groundnuts, constitute major food safety problems in Ghana due to poor handling and storage. For instance, Awuah and Kpodo (1996) reported AF levels ranging from 5.7 to 22,168 ppb in market groundnut samples in Ghana. Another study in Ghana indicated that total AF levels in "kenkey" (a common maize-based meal) ranged from 6.2 to 196.1 ppb, with a mean value of 50.9 ppb, in 94% of the samples collected.

The most common effect associated with chronic $AFB_1$ exposure is the increased incidence of hepatocellular carcinoma (HCC). $AFB_1$ is implicated as a major risk factor in the etiology of HCC, particularly in tropical areas of sub-Saharan regions of Africa, Southeast Asia and South America. The carcinogenic potency of $AFB_1$ in individuals positive for hepatitis B virus (HBV) surface antigen (HBsAg) is about 30-fold higher compared to individuals who are negative for HBsAg. Therefore, it is imperative to develop and implement intervention strategies that are effective against AFs in the diet, particularly for humans at high-risk for aflatoxicosis or AF-synergized risks, such as HCC from HBV. Given the estimate that 80% of HCC cases occur in developing countries, preventive strategies should be economically feasible, culturally acceptable and sustainable.

It is well documented in the extant scientific literature that AFs are ubiquitous, naturally occurring contaminants in a variety of food products and have been associated with disease and death in humans and animals. While this problem may not pose a significant threat to developed countries, AF contamination in food products remains a serious burden in the developing world where a lack of untainted food supplies and poverty present a major and persistent challenge. Avoiding consumption of AF-contaminated foods is one of the most fundamental approaches for reducing risk of aflatoxicosis in humans. However, this is not feasible for many communities in developing countries and emphasizes the need for viable intervention strategies to manage aflatoxin contaminated diets and treat aflatoxicosis.

One approach is chemoprevention. This strategy involves the use of natural or synthetic agents to block, retard, reverse or modulate the carcinogenic process of AFs. Many chemopreventive agents have been studied and some exist as natural constituents in the human diet. In numerous clinical trials, researchers have demonstrated that chemopreventive chemicals, such as oltipraz, chlorophyllins and green tea derived polyphenols, are effective against AFs in various animal models and humans. Since these compounds are absorbed by the gastrointestinal tract and affect cellular metabolism, their extended use in humans would require very careful evaluation, including long-term effects of enzyme modulation and interferences with the uptake of essential nutrients from the diet. In the current example, a study is conducted of the dietary inclusion of a calcium aluminosilicate clay that is not absorbed and can preferentially bind AFs in the gastrointestinal tract and reduce toxin bioavailability to the blood, liver and other organs.

NovaSil® (NS) (Englehard Chemical Corp., Iselin, N.J.) is a naturally occurring, processed calcium montmorillonite clay used as an anti-caking agent. Equilibrium adsorption isotherms and molecular modeling studies have shown that NS preferentially binds AFs that contain a planar ketolactone system. Previous short-term studies in rodents, chicks, turkey poults, pigs, lambs, dairy goats and cattle, confirmed that dietary inclusion of NS results in significant protection from AFs. In all these studies, no observable adverse effects were reported following dietary ingestion of NS clay. In developmental toxicology studies in Sprague-Dawley (S-D) rats fed dietary NS at concentrations as high as 2% (w/w) throughout pregnancy, no NS-related maternal or fetal toxicity was detected and no significant changes occurred in trace metal bioavailability in a variety of maternal and fetal tissues. In a recent long-term study (6.5 months) in S-D rats treated with 0.25-2% (w/w) dietary NS clay, there were no dose dependent or NS-related adverse effects on body weight gains, relative organ weights, gross and histological appearance of major organs, or hematological and serum biochemistry parameters. Additionally, levels of essential nutrients including vitamins A and E, and the micronutrients Fe and Zn were unaffected.

Prior to initiating the clinical study described in this example, NS clay was analyzed for potentially toxic metal and dioxin contaminants to ensure: 1) compliance with international and federal standards, and (2) levels below the TDI (tolerable daily intake) for foods based on JECFA standards. The results, shown in Table 1 below, indicate that NS clay does not contain any contaminants that exceed the mandated standards.

TABLE 1

Priority metals and dioxins/furans in NS

| Chemical/Compound[a] | Avg Conc. in NS (mg/Kg)[b] | 3 g NS (mg)[c] | JECFA 1998 TDI (mg/day)[d] |
|---|---|---|---|
| As | 2.2267 | 0.00668 | 0.310 |
| Ba | 72.4333 | 0.21730 | 3.570 |
| Cd | 0.2603 | 0.00078 | 0.060 |
| Co | 1.3566 | 0.00407 | 0.016 |
| Cr | 1.1233 | 0.00337 | 0.250 |
| Hg | 0.0090 | 0.00003 | 0.043 |

TABLE 1-continued

Priority metals and dioxins/furans in NS

| | | | |
|---|---|---|---|
| Mo | 0.1500 | 0.00045 | 0.110 |
| Ni | 2.8233 | 0.00847 | 0.300 |
| Pb | 10.3333 | 0.03100 | 0.210 |
| Se | 0.5333 | 0.00160 | 0.057 |
| Sr | 1430.000 | 4.29000 | 5.000 |
| Zn | 66.93333 | 0.20080 | 10.000 |

| Dioxins/Furans | TEQ (pg/g NS) | TEQ pg/Kg-BW/day | TDI (pg/Kg-BW/day) |
|---|---|---|---|
| TCDD, TCDF, etc. | ND | — | 2.3 |
| OCDD + HpCDD | 0.0679 | 0.0029 | 2.3 |

[a] Priority toxic metals and dioxin/furans based on EPA (Superfund) and the Joint FAO/WHO Expert Commission on Food Additives (JECFA) criteria;
[b] Concentrations of priority metals and dioxin/furans were determined in parent NS;
[c] Derived dose of metals and TEQ for dioxins/furans corresponding to 3 g of NS (assuming bioavailability of the total concentration);
[d] Tolerable daily intake from foods based on JECFA criteria. The estimated median intake of Sr worldwide from food and water is 1-5 mg/day (WHO).

Given the safety and efficacy of NS, as demonstrated in a variety of animal models, it was hypothesized that NS-based intervention would be beneficial for the treatment of humans who are frequently exposed to high levels of aflatoxins and at risk of aflatoxicoses. As a precursor to a human clinical trial with NS in Ghana, a short-term (2 weeks) double-blind phase I study was conducted to: (1) evaluate the safety and tolerance of NS capsules in 50 healthy human volunteers; and (2) establish optimal protocols for human intervention studies. After 14 days of NS ingestion (1.5 and 3.0 g day$^{-1}$), participants' compliance (99.1%) was excellent; physical examination results, urinalysis, serum biochemical and hematological parameters were unaffected; serum minerals and vitamins A and E levels were not significantly different from baseline values (Wang et al. 2005). Apart from its demonstrated safety, the 3.0-g dose of NS per day used for the clinical intervention trials, was extrapolated from previous in vitro and in vivo studies, including Pimpukdee et al. (2004), showing that 0.25% NS in the diet was the minimal effective dose that protected chicks from AF toxicity. This study provided the basis for the current Phase IIa human intervention study at Ejura-Sekyedumase district (ESD) of the Ashanti region of Ghana, West Africa.

The ESD of the Ashanti region was chosen as the intervention study site based on a report that AFB$_1$-albumin adducts and aflatoxin M1 metabolites were detected in 100% of 140 sera samples and 91.2% of 91 urine samples collected from study participants in the area (Jolly et al. 2006). These findings are supported by Wild et al. (1992) in that a majority (75-100%) of people from East and West African countries test positive for blood AFB$_1$-albumin adducts. In this report, our main objective was to evaluate the safety of NS when administered to humans for the management of aflatoxicoses by: (1) determining potential adverse effects of NS in human subjects over a 3-month period and (2) establishing a basis and dosimetry for long-term (Phase IIb or Phase III) studies in human subjects.

Ejura-Sekyedumase district (ESD) is one of the 21 districts in the Ashanti Region, Ghana. Its climatic conditions and soil fertility favor cropping and approximately 76% of the populace engages in agriculture. The main crops produced and consumed in this area include maize, groundnuts, yams, cassava, cotton and tobacco (Adu and Mensah-Ansah 1995; District Health Directorate, Ejura/Sekyedumase 2005). The District Health Director and other health personnel coordinated the community entry process and introduced the research team to the leaders and residents of six communities, which constitute over half of the district population. Prior to the study, four of these communities had established AF baseline data and demographic information (Jolly et al. 2006). The other two communities are in the Ejura sub-district, which has the highest population in the entire area.

Leaders of each community organized a meeting for the investigators to define the purpose, duration, time frame, responsibilities of potential participants and monitors and other aspects of the study, and to allow the residents time for questions and answers. After the community entry and sensitization process, a total of 507 residents from the six communities volunteered to participate in the study. Following explanation of the informed consent document, volunteers signed it and completed a survey instrument comprising health history and food frequency questionnaires. Subjects were then given coded identification numbers and were provided sterile covered cups to collect specimens of their first urine in the morning. On the sample collection day, volunteers went through physical examinations performed by on-site physicians. Also, they provided urine specimens for urinalysis and human chorionic gonadotropin (HCG) test to determine pregnancy status, and donated a total of 15 ml blood in two tubes (5 ml in one tube and 10 ml in another) for AF exposure analysis, liver and kidney function, and hematology. The 5-ml aliquots of the blood specimens were sent to the Ejura District Hospital, Ashanti Region, Ghana for hematological analysis (mainly WBC count, hemoglobin and hematocrit). Aliquots of sera collected from the 10-ml blood specimens were used for liver and kidney function tests at the Noguchi Memorial Institute for Medical Research (NMIMR), University of Ghana, Legon, Accra. The remaining serum samples were stored at −20° C. and later shipped to Texas Tech University (TTU) to determine AFB$_1$-albumin adduct levels of each volunteer.

Individuals (males and females) who qualified as study subjects met the following criteria: healthy status based on physical examination results, age 18-58 years, intake of corn and/or groundnut-based foods at least 4 times a week, blood AFB$_1$-albumin adduct levels>0.5 μmol AFB$_1$ per mg albumin adducts (LOD=0.05 μmol AFB$_1$ permg albumin), no history of chronic disease(s), no use of prescribed medications for chronic or acute illness, non-pregnant and/or non-breastfeeding females, normal ranges of hematological parameters, liver and renal function indicators (blood and urine parameters), and a signed consent form. Subjects with abnormal liver function values (ALT) were excluded from the study. Therefore, no acute hepatitis patients were included in the study, regardless of their HBV status (HB sAg+ or HBsAg—). Of the 507 volunteers, there were 302 subjects who met all of the inclusion criteria other than the AF-Alb adduct levels. A target population of 180 subjects was selected from this group based exclusively on their adduct levels. To determine if NS was effective and further evaluate its safety, a total sample size of 180 subjects (with 60 per treatment group) was chosen based on the standard 100-300 subjects required by the US NIH Guidelines (2006) for Phase II clinical studies. At the beginning of the trial, two females and one male dropped out leaving 177 (101 males, 76 females) who were finally recruited as study participants.

NovaSil clay (NS) was obtained from Engelhard Chemical Corporation (Iselin, N.J., USA). Initially, the NS clay used for the human study was evaluated for potential environmental contaminants including polychlorinated dibenzo-p-dioxins/furans (PCDDs/PCDFs) and heavy metals. Evaluation of NS for the US Environmental Protection Agency (USEPA) priority dioxins/furans (17) was performed by Columbia Analytical Services (CAS), Inc. (Houston, Tex., USA). Standardized procedures of USEPA methods were used for sample preparation, cleanup and analysis with high resolution capillary column gas chromatography/high resolution mass spectrometry (USEPA Method 1613B). Also, the NS clay was analyzed for heavy metals (e.g. As, Cd, Hg, and Pb) by CAS, Inc. (Kelso, Wash., USA). Metal analysis procedures followed standard USEPA protocols (e.g. Method 6010B and 7471A). NS clay (containing acceptable levels of contaminants) was sent to College Pharmacy (Colorado Springs, Colo., USA) for encapsulation under sterile conditions in a setting with good manufacturing practices. Capsules, with the same size, shape and color, were formulated to contain 500 mg NS, 250 mg NS or placebo, based on previous dosimetry protocols (Wang et al. 2005). The capsules were then sterilized in sealed plastic containers, approximately 180 capsules/container, by electron beam irradiation (National Center for Electron Beam Food Research, Texas A&M University). A target dose range of 8.2-9.4 KGy was applied and followed protocols similar to those used for sterilizing human foods in the USA. All other chemicals, reagents and solvents used were obtained commercially at the highest purity available.

The overall study design followed the guidelines for a randomized, double-blind, placebo controlled Phase II clinical trial. Study protocol was approved by both the TAMU Institutional Review Board (IRB) and NMIMR-IRB for Ethical Clearance in Ghana. Screening of volunteers was initiated in September 2005. The trial started in December 2005 and was completed in April 2006 (including a 1-month post-trial follow-up). The subjects who met the recruitment criteria were randomly divided into three study groups (60/group) based on serum $AFB_1$-albumin adduct levels. The first three subjects with the highest AF exposure levels were randomly divided into the three groups, followed by participants with the next three highest exposure levels and so on until all the 180 subjects were divided. As a double-blind study, the participants, on-site doctors, nurses and all other field workers had no knowledge of the contents of the capsules. To ensure maximum compliance to the defined treatment regimens, maintain blinding to weights of NS capsules and participant well-being, trained study monitors delivered the capsules daily, witnessed ingestions and recorded any symptoms that subjects might have experienced. Physical examinations were performed monthly to evaluate the general health status of study subjects. Urine and blood samples from each participant were collected at the beginning (time 0), 1, 2 and 3 months of NS ingestion. After 3 months of capsule ingestion, subjects were monitored without NS treatment for another month. At the end of the fourth month, participants underwent final physical examinations and blood and urine specimens were collected. EDTA-blood samples were sent to Komfo Anokye Teaching Hospital (KATH) in Kumasi, Ghana for hematological analysis utilizing an Auto-Analyzer, Sysmex KX-21 (Sysmex Corporation, Kobe, Japan). Serum biochemical analysis was performed at NMIMR with a chemistry auto-analyzer (Eos Bravo Plus; Hospitex Diagnostics, Italy). An Electrolyte (Na/K) auto-analyzer (Humalyte; Human Diagnostic, Germany) was used for electrolyte analysis at NMIMR. Portions of urine and serum samples were shipped to TAMU and TTU for efficacy evaluations. Briefly, urine samples were analyzed for an acute biomarker of AF exposure, AFM1, following protocols reported by Groopman et al. (1992), with modifications of Sarr et al. (1995) and Wang et al. (1999). $AFB_1$-albumin adduct, another biomarker delineating long-term exposure to AFs, was measured in the serum using protocols reported by Wang et al. (1996).

Participants were given ID numbers and randomly assigned to one of the following three treatment groups: high-dose (HD), low-dose (LD) or placebo (PL), implying that they would take two capsules containing 500 mg NS, 250 mg NS and 250 mg placebo, respectively, 3 times day—1 (before meals and with at least 100 ml of water) over a period of 3 months. In total, the HD and LD groups received 3.0 and 1.5 g NS $day^{-1}$, respectively. As a safety precaution, 3.0 g NS was selected as the highest dose since it represented the MED (minimal effective dose) of NS for AFs based on previous animal studies. Dose selection for this study was also based on extrapolations from previously published dosimetry data in animal models (Phillips 1999; Phillips et al. 2002, 2006) and NS levels used for a short-term human study in the USA (Wang et al. 2005). The HD (3.0 g NS $day^{-1}$) represents approximately 0.25% NS (w/w) of the estimated amount of food consumed daily by an average Ghanaian. Furthermore, up to 2% NS (w/w) in the diet, which is 8 times higher than the HD level in this study, exhibited no significant adverse effects in rodents following 6.5 months of exposure (Afriyie-Gyawu et al. 2005).

To monitor potential toxicity of NS ingestion, a symptom checklist was developed and included with the Daily Diary Worksheet (DDW) as an assessment tool. Study monitors recorded any adverse events and were required to report any health problem to the supervisor and/or on-site physician. Physicians on the investigative team reviewed the DDW every 2 weeks. Symptoms were assessed based on the following criteria:

Mild (grade 1), slightly bothersome and relieved with symptomatic treatment;

Moderate (grade 2), bothersome and interfered with activities and only partially relieved with symptomatic treatment;

Severe (grade 3), prevented regular activities and not relieved with symptomatic treatment.

Whenever symptom(s) were reported, physical examinations and laboratory analysis were performed for verification, if necessary, during the study. Subjects were treated by the on-site physician and allowed to continue the study if symptoms were not perceived to be related to NS ingestion. If symptoms were linked to NS capsules, the participant was treated and asked to discontinue capsule ingestion. The on-site physician had access to an Adverse Event Report document, developed under US NIH Guidelines, for reporting any adverse effects to the investigators and the IRBs of NMIMR and TAMU.

All data were entered by the data management team at NMIMR using the coded identification numbers of the subjects. Personnel, other than the investigators, had no access to the names of the participants. All data from the questionnaires, clinical reports, DDW for ingestion and toxicity monitoring and adverse event episodes were entered and managed using Microsoft Excel software. Upon completion of the data entry process, two investigators independently reviewed the recorded data to ensure accuracy.

To show the safety of NS capsule ingestion, the statistical evaluation focused on the comparisons among different treatment levels and different time points. Means, standard deviations and medians were calculated for each parameter, and the values of parameters are expressed as mean±SD unless otherwise stated. To the parameters that were normally distributed, two-factorial ANOVA and Bonferroni procedures were used to compare significant differences between means of different treatment arms and times. Chi-square test was used for analysis of adherence and rate of side effect/toxicity data. To the parameters that were not normally distributed, Kruskal-Wallis test or Wilcoxon rank sum test were used to compare the difference among different treatment groups and different time points. A P value of less than 0.05 (two-tailed) was considered significant. All analyses were done with SAS software version 9.1.3 (SAS Institute Inc., Cary, N.C., USA).

The amount of dioxins/furans and metal in the NS clay was analyzed. Among the 17 USEPA priority PCDDs/PCDFs, 1,2,3,4,6,7,8-heptachlorodibenzo-p-dioxin (HpCDD) and octachlorodibenzo-p-dioxin (OCDD) were the only two contaminants in NS present above the limits of detection (LODs=1.11 parts per trillion (ppt) for HpCDD and 1.91 ppt for OCDD). The mean concentrations of HpCDD and OCDD in NS clay were 4.42 and 23.74 ppt, respectively. Applying the toxic equivalent factors (TEFs) (WHO 1998), the toxic (or TCDD) equivalent (TEQ) values of these dioxins were calculated to be 0.0442 and 0.00237 ppt for HpCDD and OCDD, respectively, with a combined TEQ of 0.0466 ppt in NS. In the HD treatment, the 3.0-g of NS provided a TEQ of 0.1397 pg day$^{-1}$. According to WHO standards, the tolerable human intake (THI) of TCDD is 2.3 pg kg$^{-1}$ BW day$^{-1}$, translated to be 161 pg day$^{-1}$ for a 70-kg man and 138 pg day$^{-1}$ for a 60-kg woman. Based on these values, the TEQ from 3.0 g NS day$^{-1}$ would be approximately 1,000 and 1,100 times lower than the daily WHO-THI standards for an average woman and man, respectively. Heavy metals, such as As, Cd and Pb, had levels that ranged from 7- to 80-fold lower (data not shown) in 3 g NS day$^{-1}$ compared to the standard recommended values (JECFA 1998). Hg was found to be below the detection limit (LOD=0.009 mgkg$^{-1}$ NS) based on the analytical method used.

All 507 volunteers screened were positive for serum $AFB_1$-albumin adducts (range: 0.1-4.7 pmol $AFB_1$ mg$^{-1}$ albumin). Table 2 below delineates the demographic characteristics of the subjects enrolled in the study. Initially, we selected a total study population of 180 based on defined inclusion criteria and randomly divided them into three groups (60 per group)—HD, LD and PL—based on participants' serum $AFB_1$-albumin adduct levels. Three subjects (one from LD and two from PL groups) were removed once the day treatment was initiated—two females became pregnant and one male opted out because of a new job. Physical parameters, such as age, body weight and diastolic blood pressure, were not significantly affected after 3 months of NS ingestion. At the end of trial, the mean values of systolic blood pressure (SBP), although no clinical significance, were significantly reduced (P<0.01) for LD (112.7±15.0 mmHg) and PL (117.4±19.8 mm Hg) compared to baseline values of 121.9±23.1 and 129.9±24.5 mm Hg, respectively. The SBP of the HD group was unchanged.

TABLE 2

Demographics and physical parameters

| Demographic characteristics | Treatment group | | |
| --- | --- | --- | --- |
| | High dose | Low dose | Placebo |
| Participants | 60 | 59 | 58 |
| Gender | | | |
| Male | 34 | 31 | 37 |
| Female | 26 | 28 | 21 |

TABLE 2-continued

Demographics and physical parameters

| Demographic characteristics | Treatment group | | |
| --- | --- | --- | --- |
| | High dose | Low dose | Placebo |
| Community | | | |
| Dromankoma | 13 | 12 | 20 |
| Ejura Group | 10 | 8 | 9 |
| Nkwanta | 6 | 8 | 5 |
| Hiawoanwu | 18 | 15 | 12 |
| Kasei | 3 | 5 | 3 |
| Kotokoli Line | 10 | 11 | 9 |
| Age (years)[a] | 38.6 ± 13.0 | 37.3 ± 11.8 | 36.5 ± 10.8 |
| Body weight (kg)[a] | | | |
| Before trial | 60.9 ± 10.2 | 59.8 ± 11.0 | 62.6 ± 9.8 |
| After trial | 61.4 ± 10.1 | 62.9 ± 10.3 | 61.3 ± 10.9 |
| Systolic blood pressure (SBP) (mmHg)[a,b] | | | |
| Before trial | 126.4 ± 22.6 | 121.9 ± 23.1 | 129.9 ± 24.5 |
| After trial | 121.0 ± 20.0 | 112.7 ± 15.0** | 117.4 ± 19.8** |
| Diastolic blood pressure (DBP) (mmHg)[a,b] | | | |
| Before trial | 79.1 ± 15.8 | 77.1 ± 15.2 | 81.5 ± 14.7 |
| After trial | 79.0 ± 16.2 | 75.0 ± 11.3 | 77.2 ± 13.7 |

[a]Mean ± SD;
[b]normal values are 120/80 for SBP/DBP;
*P < 0.05,
**P < 0.01 compared to baseline values.

The percentages of study participants who completed the entire 3-month trial were 90.0, 89.8 and 94.8% for HD, LD and PL, respectively, and the overall number of subjects who completed the study constituted 91.5%. A total of 15 (six from HD, six from LD and three from PL) of the 177 study subjects did not complete the study. In terms of compliance, 97.4, 96.4 and 98.6% of participants in HD, LD and PL groups, respectively, adhered to the NS-treatment regimen according to the study protocol. The overall adherence (number of times capsules were taken) among the participants, whether or not they completed the study, was over 97%. Data representing participant compliance and study completion are summarized in Table 3 below.

TABLE 3

Participant compliance and completion of treatment regimen

| | Treatment group | | | |
| --- | --- | --- | --- | --- |
| | High dose | Low dose | Placebo | Overall |
| Participants | | | | |
| Started | 60 | 59 | 58 | 177 |
| Completed (3 months) | 54 | 53 | 55 | 162 |
| Completion (%) | 90.0% | 89.8% | 94.8% | 9135% |
| Treatment regimen | | | | |
| Times capsule taken | 14847 | 14697 | 15035 | 44579 |
| Times capsule missed | 390 | 543 | 220 | 1153 |
| Total reported | 15237 | 15240 | 15255 | 45732 |
| Adherence (%) | 97.4 | 96.4 | 98.6 | 97.5 |

Symptoms reported to the study monitors by participants are indicated in Table 4 below. The NS dose levels (1.5 or 3.0 g day) were tolerable for the participants in the HD and LD groups. Symptoms reported included nausea, vomiting, diarrhea, abdominal discomfort, heartburn and dizziness. Over 50% of the reported symptoms occurred during the first 2 weeks of the study and the rest were reported intermittently afterwards until the end of the study. Forty-five study participants (approximately 56% females and 44% males) reported at least one of these symptoms across all the three groups—17 (37.8%) from HD, 13 (28.9%) from LD and 15 (33.3%) from the PL groups. None of these effects appeared to be dose-dependent or NS-related, except for the episodes of nausea. A majority of these symptoms were reported by between one and three of the subjects in any of the groups, except for vomiting, diarrhea, heartburn and dizziness, which were reported by more than three people but in no particular dose-dependent trend. For instance, a single 44-year-old female subject in the HD group was responsible for 20 of the 28 times dizziness was recorded (Table III). Heartburn incidences also appear to be high in the LD group, but only two subjects reported the effect—one subject reporting 18 of the 22 times recorded. Most of the symptoms were graded as "mild," a few of them "moderate," and none of them were "severe" incidences. Over 99% of the time, participants reported no adverse health consequences throughout the study.

TABLE 4

Health incidences reported

| Adverse event | Treatment group | | | |
|---|---|---|---|---|
| | High dose | Low dose | Placebo | Overall |
| Indigestion | 1[a] | 1 | 4 | 6 |
| Nausea | 6 | 4 | 0 | 10 |
| Vomiting | 4 | 8 | 2 | 14 |
| Constipation | 0 | 1 | 0 | 1 |
| Diarrhea | 21 | 2 | 13 | 36 |
| Flatulence | 1 | 10 | 1 | 12 |
| Loss of appetite | 7 | 3 | 2 | 12 |
| Abdominal discomfort | 10 | 15 | 8 | 33 |
| Heartburn | 11 | 22 | 2 | 35 |
| Dizziness | 28 | 21 | 32 | 81 |
| Insomnia | 0 | 1 | 1 | 2 |
| Bloating | 0 | 0 | 0 | 0 |
| No side-effect | 15,148 (99.42%) | 15,152 (99.42%) | 15,190 (99.77%) | 45,491 (99.47%) |
| Total incidence | 89 (0.58%) | 88 (0.58%) | 65 (0.43%) | 242 (0.53%) |

[a]Indicates number of times a health incidence was reported.

In the hematological analysis, shown in Table 5 below, there were no significant, dose-dependent effects in any of the parameters among the three treatment groups, either before or after the 3-month trial (data not shown). In terms of time effects, only % monocytes in the white blood cell (WBC) differential analysis showed significant reductions in: HD group at end of trial (2.2±1.7%, mean±SD) compared to the baseline value (3.2±2.1%) ($P<0.05$); PL control group (2.5±2.1%) at end of trial compared to the baseline value (3.4±1.7%) ($P<0.01$) (Table IV). This effect was not observed in the LD group. All other parameters were unaffected. In addition, no significant differences were observed between the NS-treated (HD and LD) and placebo (PL) groups in all the parameters evaluated.

TABLE 5

Hematological analysis

| Parameter | High dose | | Low dose | | Placebo | | Clinical reference |
|---|---|---|---|---|---|---|---|
| | Before trial | After trial | Before trial | After trial | Before trial | After trial | |
| WBC ($10^9$ $l^{-1}$) | 5.3 ± 3.4[a] | 5.6 ± 1.9 | 4.9 ± 1.5 | 5.6 ± 1.5 | 5.0 ± 1.4 | 5.5 ± 2.1 | 3.4-8.9 |
| RBC ($10^6$ $mm^{-3}$) | 4.9 ± 0.5 | 5.0 ± 0.6 | 4.8 ± 0.5 | 4.9 ± 0.6 | 4.9 ± 0.6 | 5.0 ± 0.6 | 2.5-5.5 |
| HEMOGL (g $dl^{-1}$) | 13.8 ± 1.7 | 13.9 ± 1.5 | 13.5 ± 1.8 | 13.8 ± 1.9 | 13.5 ± 1.5 | 13.8 ± 1.6 | 11.7-16.5 |
| HEMATOC (%) | 43.2 ± 4.9 | 43.2 ± 4.4 | 42.7 ± 4.8 | 43.1 ± 5.1 | 41.5 ± 5.6 | 42.9 ± 4.5 | 37.1-51.4 |
| MCV (fl) | 87.7 ± 6.3 | 87.3 ± 6.2 | 89.1 ± 7.2 | 87.6 ± 8.1 | 86.3 ± 7.2 | 86.6 ± 6.7 | 86-110 |
| MCH (pg) | 27.9 ± 2.7 | 28.1 ± 2.8 | 28.1 ± 3.0 | 28.1 ± 3.4 | 32.8 ± 31.0 | 28.0 ± 2.5 | 26-38 |
| MCHC (g $dl^{-1}$) | 31.8 ± 1.4 | 32.2 ± 1.4 | 31.5 ± 1.4 | 31.6 ± 2.6 | 31.5 ± 3.6 | 31.2 ± 5.3 | 31-37 |
| PLT (109 $l^{-1}$) | 226.2 ± 90.1 | 223.7 ± 63.6 | 223.6 ± 96.0 | 240.6 ± 75.1 | 229.8 ± 69.7 | 231.9 ± 60.9 | 97-356 |
| NEUTRO (%) | 34.1 ± 9.6 | 36.6 ± 7.5 | 32.2 ± 8.9 | 35.5 ± 10.5 | 34.4 ± 9.3 | 37.8 ± 10.1 | 40-75 |
| LYMPHO (%) | 49.1 ± 9.2 | 46.1 ± 7.9 | 50.1 ± 9.6 | 47.9 ± 10.2 | 48.2 ± 9.0 | 47.5 ± 8.4 | 20-45 |
| MONO (%) | 3.2 ± 2.1 | 2.2 ± 1.7± | 2.6 ± 1.6 | 2.1 ± 1.6 | 3.4 ± 1.7 | 2.5 ± 2.1** | 2-10 |

TABLE 5-continued

Hematological analysis

| | Treatment group | | | | | | Clinical reference |
|---|---|---|---|---|---|---|---|
| | High dose | | Low dose | | Placebo | | |
| Parameter | Before trial | After trial | Before trial | After trial | Before trial | After trial | |
| EOSINO (%) | 13.4 ± 7.7 | 15.0 ± 8.8 | 15.0 ± 10.0 | 14.4 ± 9.0 | 15.9 ± 17.0 | 12.2 ± 5.7 | 1-6 |
| BASO (%) | 0.2 ± 0.5 | 0.1 ± 0.4 | 0.1 ± 0.4 | 0.1 ± 0.2 | 0.2 ± 0.5 | 0.1 ± 0.4 | <1 |

[a]Mean ± SD,
*P < 0.05,
**P < 0.01 significant compared to corresponding baseline values.

Analysis of serum biochemistry indicated isolated statistically significant differences in a few parameters as presented in Table 6 below. Alanine aminotransferase (ALT) level significantly increased only in the PL group at the end of trial compared to the baseline value (P<0.05). Total bilirubin (T-BILI) contents marginally decreased in the HD (P<0.01) and PL (P<0.05) groups after 3 months of NS ingestion compared to baseline levels. This effect did not occur in the LD group. Also, blood urea nitrogen (BUN) levels were significantly reduced in all the treatment groups at the end of the study compared to baseline values. Serum creatinine (CREAT) levels slightly increased in all groups at the end of trial (P<0.01). Sodium levels significantly increased at end of trial in the HD and LD groups compared to baseline values. This effect did not occur in the PL group. Potassium level in the PL group was slightly reduced at the end of trial compared to baseline (P<0.01). In all these biochemical effects, no statistically significant differences were observed between the NS-treated groups and the placebo group at the end of trial. All other serum biochemical parameters evaluated were unaffected. Two physicians (one practicing clinician in Ghana and one non-practicing in the USA) validated the results of all the parameters evaluated in the study.

hematological and biochemical parameters. Apart from the randomized, double-blind and placebo-control design, considerable efforts were made to minimize potential confounding variables. For instance, analysis of PCDD/PCDF indicated that HD and LD groups received 1000 and 2000 times less dioxin in the encapsulated NS than the WHO-THI standards. This is important because PCDD/PCDF congeners can accumulate in fatty tissues and become highly toxic to humans (Startin et al. 1990; Jensen 2001).

Study participants were selected based on predefined inclusion criteria, but the randomization process was conducted strictly on the basis of their serum $AFB_1$-albumin adduct concentrations. This deliberate design feature led to the disparity in numbers of participants (per group) regarding gender and community representation. Body weight and blood pressure values were unaffected in a dose-dependent fashion. Participants' adherence to the treatment regimens was excellent (over 97%) and more than 90% of the study subjects completed the study, which is noteworthy for a 3-month study (Table II). The NS dose levels were tolerable for the participants. None of the few symptoms reported appeared to be NS-related except for nausea. However, only one person reported nausea six times and one person reported it four times in the HD and LD groups, respectively, during the 3-month trial.

TABLE 6

Serum biochemistry

| | Treatment group | | | | | | Clinical reference range |
|---|---|---|---|---|---|---|---|
| | High dose | | Low dose | | Placebo | | |
| Parameter | Before trial | After trial | Before trial | After trial | Before trial | After trial | |
| ALT@($UI^{-1}$) | 13.0 ± 11.0* | 13.8 ± 8.9 | 12.7 ± 7.8 | 15.4 ± 13.5 | 13.7 ± 7.6 | 18.9 ± 21.0* | 0-45 |
| AST@($UI^{-1}$) | 29.1 ± 10.3 | 28.3 ± 14.4 | 30.7 ± 20.2 | 31.3 ± 18.2 | 29.2 ± 12.8 | 31.5 ± 12.0 | 0-35 |
| ALK-P@($UI^{-1}$) | 183.8 ± 77.0 | 183.1 ± 44.2 | 168.0 ± 53.9 | 171.7 ± 52.4 | 161.5 ± 45.6 | 162.5 ± 59.7 | 0-270 |
| T-BILI@(mg@$dl^{-1}$) | 0.8 ± 0.3 | 0.6 ± 0.4** | 0.7 ± 0.3 | 0.6 ± 0.3 | 0.8 ± 0.3 | 0.6 ± 0.3* | 0-1 |
| GGT@($UI^{-1}$) | 31.4 ± 14.9 | 33.1 ± 21.1 | 47.3 ± 98.5 | 35.0 ± 27.3 | 26.8 ± 12.5 | 29.2 ± 9.7 | 0-50 |
| T-PROT@(g@$dl^{-1}$) | 8.9 ± 1.2 | 8.8 ± 1.3 | 8.8 ± 1.3 | 8.8 ± 1.5 | 8.1 ± 1.2 | 8.4 ± 1.3 | 5-8 |
| ALBUM@(g@$dl^{-1}$) | 4.8 ± 0.6 | 4.6 ± 0.4** | 4.7 ± 0.3 | 4.6 ± 0.5 | 4.7 ± 0.8 | 4.6 ± 0.5 | 3.5-5.5 |
| BUN@(mg@$dl^{-1}$) | 11.8 ± 4.7 | 9.9 ± 3.0* | 13.7 ± 6.1 | 1.1 ± 3.8* | 12.5 ± 4.9 | 10.3 ± 3.3** | 8-23 |
| CREAT@(mg@$dl^{-1}$) | 0.7 ± 0.2 | 1.0 ± 0.2** | 0.8 ± 0.2 | 1.0 ± 0.3** | 0.8 ± 0.7 | 1.0 ± 0.3** | 0.6-1.6 |
| TRIGLYC@(mg@$dl^{-1}$) | 89.6 ± 27.5 | 82.8 ± 32.1 | 93.0 ± 40.4 | 80.6 ± 30.7 | 82.3 ± 28.1 | 81.7 ± 31.0 | 40-200 |
| Ca@(mg@$dl^{-1}$) | 9.5 ± 1.3 | 9.1 ± 0.8 | 9.4 ± 1.6 | 9.0 ± 0.7 | 9.0 ± 1.2 | 8.8 ± 0.9 | 8.6-10.4 |
| Mg@(mg@$dl^{-1}$) | 1.9 ± 0.4 | 1.9 ± 0.2 | 2.0 ± 0.4 | 1.9 ± 0.3 | 1.9 ± 0.4 | 1.9 ± 0.3 | 1.3-2.4 |
| Na@(mmol $l^{-1}$) | 142.2 ± 6.6 | 146.2 ± 9.7* | 141.8 ± 6.5 | 146.7 ± 7.1** | 142.6 ± 6.9 | 145.4 ± 8.9 | 120-146 |
| K@(mmol $l^{-1}$) | 4.6 ± 0.7 | 4.4 ± 0.5 | 4.6 ± 0.5 | 4.4 ± 0.5 | 4.7 ± 0.7 | 4.4 ± 0.5** | 3.0-5.0 |

[a]Mean ± SD;
*P < 0.05,
**P < 0.01 significant compared to corresponding baseline values.

Results of this study indicate that administration of NS capsules (1.5 and 3.0 g $day^{-1}$) over a 3-month period, was apparently safe, as evidenced by physical examinations, Hematological analysis indicated that there were no dose-dependent significant differences between the NS-treated and PL control groups at the end of trial. In the HD and PL groups, WBC differential analysis showed significant reductions of % monocytes between the baseline and end of trial. However, this effect was well within the clinical reference range and was not observed in the LD group (Table 4). All other parameters were statistically equivalent between the NS-treated groups and the placebo control. This suggests that dietary NS is unlikely to promote inflammatory processes, impair immunity, cause alterations to bone marrow or lead to an increased incidence of infectious diseases.

Serum biochemical analysis showed isolated statistically significant differences in a few parameters with no particular trends of association or dose dependency (Table 5). Additionally, all measured parameters were within the normal physiological ranges. Overall, the effects of these parameters lacked dose-dependency and, thus, suggest that NS exhibited no significant adverse effects on the physiological levels of these standard biochemical parameters.

This phase IIa clinical intervention trial evaluates the safety and efficacy of NS clay for preventing dietary AFs in human subjects. Although significant changes in a few parameters were observed, the effects did not appear to be NS-related or dose-dependent and all were within the normal physiological boundaries. This evidence suggests that short-term inclusion of NS at a minimal effective dose (MED) of 0.25% (w/w) would not likely produce overt toxicity in humans. Importantly, these findings support the prospect of using NS to rescue and protect humans who are acutely exposed to high levels of dietary AFs. Further studies are warranted to optimize the dosimetry and delivery methods for NS. Phase IIb and phase III intervention and epidemiologic studies are also needed to confirm the safety and efficacy of NS for long-term therapy and the potential inclusion in foods for humans in areas with high incidence/prevalence of HBV and at high risk for aflatoxicosis.

Example 4

Dietary exposure to aflatoxins (AF) decreases serum and tissue vitamin (Vit) A and E levels, in addition to causing liver damage. To further evaluate the influence of NS on utilization of these two vitamins in humans, levels of Vit A and E were measured by HPLC methods in 655 serum samples collected at 0, 1, and 3 months from the individuals in the phase 2a clinical trial carried out in Example 3 above, which involved 177 healthy Ghanaian volunteers who either received 1.5 g NS/day (low dose), 3.0 g NS/day (high dose), or placebo for 3 months. Blood samples from each participant were collected at the beginning (time 0, baseline, BL), 1 month (week 4, W4), three month (week 12, WI 2), and 1 month after the trial completed (week 16, W16).

Serum Vit A and E were extracted using a liquid-liquid extraction method, followed by analysis with a Thermo Finnigan (Waltham, Mass.) HPLC system with UV detector. A gradient was adjusted to elute Vit A (detected at 325 nm), and vitamin E (detected at 292 nm), simultaneously. Standard curves were generated for sample quantification. The concentrations of the Vit A and E were adjusted by volume of the serum sample.

More specifically, human serum vitamins A (VA) and E (VE) were extracted under subdued red light following procedures previously described (Ruperez et al. 2004). Briefly, human serum samples (50 ml) were mixed with 150 ml of ethanol:chloroform (3:1, v/v, containing 0.01% BHT antioxidant) to precipitate proteins and were further extracted with 300 ml of hexane in a 1.5 ml microcentrifuge tube. After centrifugation, the hexane layer was removed and dried by Centrivap® (Labconco, Kansas, Miss.). The residue was reconstituted with 300 ml of mobile phase for HPLC analysis according to the procedures of Burri et al. (2003). Analysis was carried out using a Thermo Finnigan Liquid chromatograph with a P4000 pump, an AS3000 autosampler with a 100 ml loop, and a UV6000 LP photodiode array detector (Thermo Separation Products, Riviera Beach, Fla.). Chromatographic separation was achieved with a Microsorb 100-5 C18 column with 150 mm 4.6 mm ID and 5 mm particle size (Varian, Palo Alto, Calif.) using mobile phase A (ACN:THF:MeOH:AA at 85:5:5:5, v/v/v/v) and mobile phase B (ACN:THF:MeOH:AA at 55:35:5:5, v/v/v/v) under a flow rate of 1 ml/min with an injection volume of 50 ml. The elution profile consisted of 95% A and 5% B for the first 5 min, followed by a gradient to 5% A and 95% B over 13 min. Afterwards, conditions were maintained for 2 min. and then the column was washed with 95% A and 5% B for 8 min. The total run time was 28 min. Quantitation of both vitamins was based on comparison of peak areas and retention times to reference standards.

Mean, median, and standard deviations (SD) were calculated for serum Vit A and E concentrations, and values were expressed as mean±SD. Comparison of serum Vit A and E levels in three treatment groups at different time points were performed by using ANOVA or the Kruskal-Wallis test. Dose and time effects of NS treatment on the levels of Vit A and E were analyzed using a nonparametric mixed model. A p-value of less than 0.05 (two-tailed) was considered statistically significant. All data were analyzed using SAS software version 9.1.3 (SAS Institute Inc., Cary, N.C.).

Figure 4:
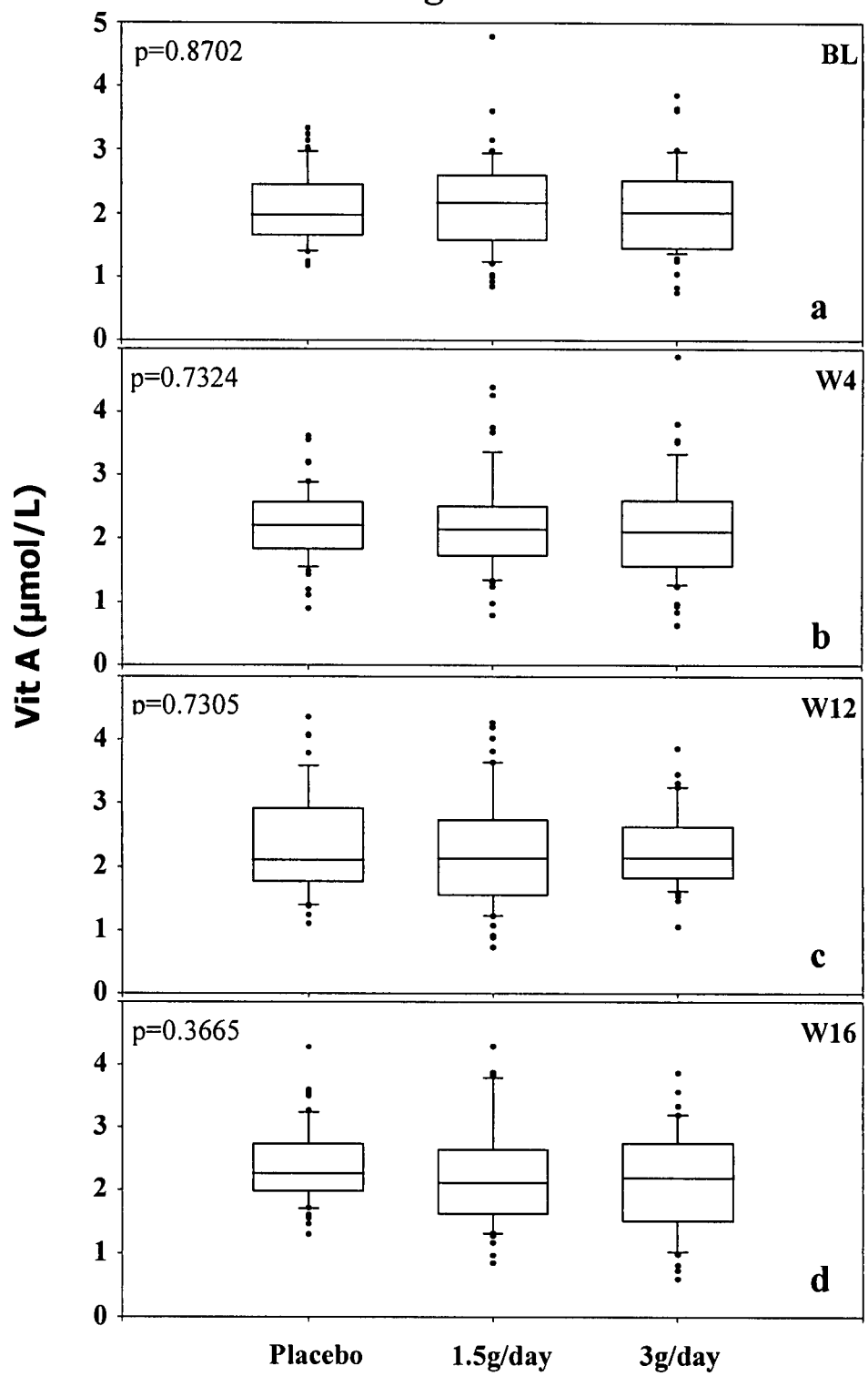
FIG. 4 shows levels of vitamin A in three groups ingesting different levels of a CAS after different time periods.

Results for serum Vit A levels in the study subjects are shown in Table 7 below. The baseline serum levels of Vit A were comparable (P=0.8702) for groups of the placebo (2.09±0.56 mol/L), the low dose (2.15±0.74 µmol/L), and the high dose (2.14±0.92 µmol/L) (FIG. 4$a$). No significance was found among groups of the low dose (2.28±0.85 µmol/L), high dose (2.21±0.95 µmol/L) and the placebo (2.21±0.57 µmol/L) in 1 month samples (P=0.7324) (FIG. 4$b$). No significance was found among groups of low dose (2.22±0.87 µmol/L), high dose (2.30±0.71 µmol/L), and the placebo (2.32 0.83 µmol/L) in 3 month samples (P=0.7305) (FIG. 4$c$). Furthermore, levels of Vit A (P=0.3665) were not statistically significant among the treated groups and the placebo group in samples collected at 1 month after the trial (FIG. 4$d$).

TABLE 7

Vit A levels (µmol/L) in three groups at different time points

| Group | N | Mean | Median | SD |
|---|---|---|---|---|
| 3.0 g/day, BL | 58 | 2.138 | 2.017 | 0.916 |
| 3.0 g/day, W4 | 57 | 2.208 | 2.104 | 0.945 |
| 3.0 g/day, W12 | 53 | 2.302 | 2.140 | 0.712 |
| 3.0 g/day, W16 | 52 | 2.197 | 2.189 | 0.902 |
| 1.5 g/day, BL | 57 | 2.145 | 2.169 | 0.743 |
| 1.5 g/day, W4 | 56 | 2.277 | 2.149 | 0.848 |
| 1.5 g/day, W12 | 51 | 2.224 | 2.132 | 0.865 |
| 1.5 g/day, W16 | 51 | 2.291 | 2.117 | 0.963 |
| Placebo, BL | 55 | 2.085 | 1.976 | 0.561 |
| Placebo, W4 | 57 | 2.210 | 2.214 | 0.570 |
| Placebo, W12 | 54 | 2.321 | 2.106 | 0.828 |
| Placebo, W16 | 54 | 2.369 | 2.266 | 0.596 |

BL (baseline),
W4 (week 4),
W12 (week 12),
W16 (week 16)

Figure 5:
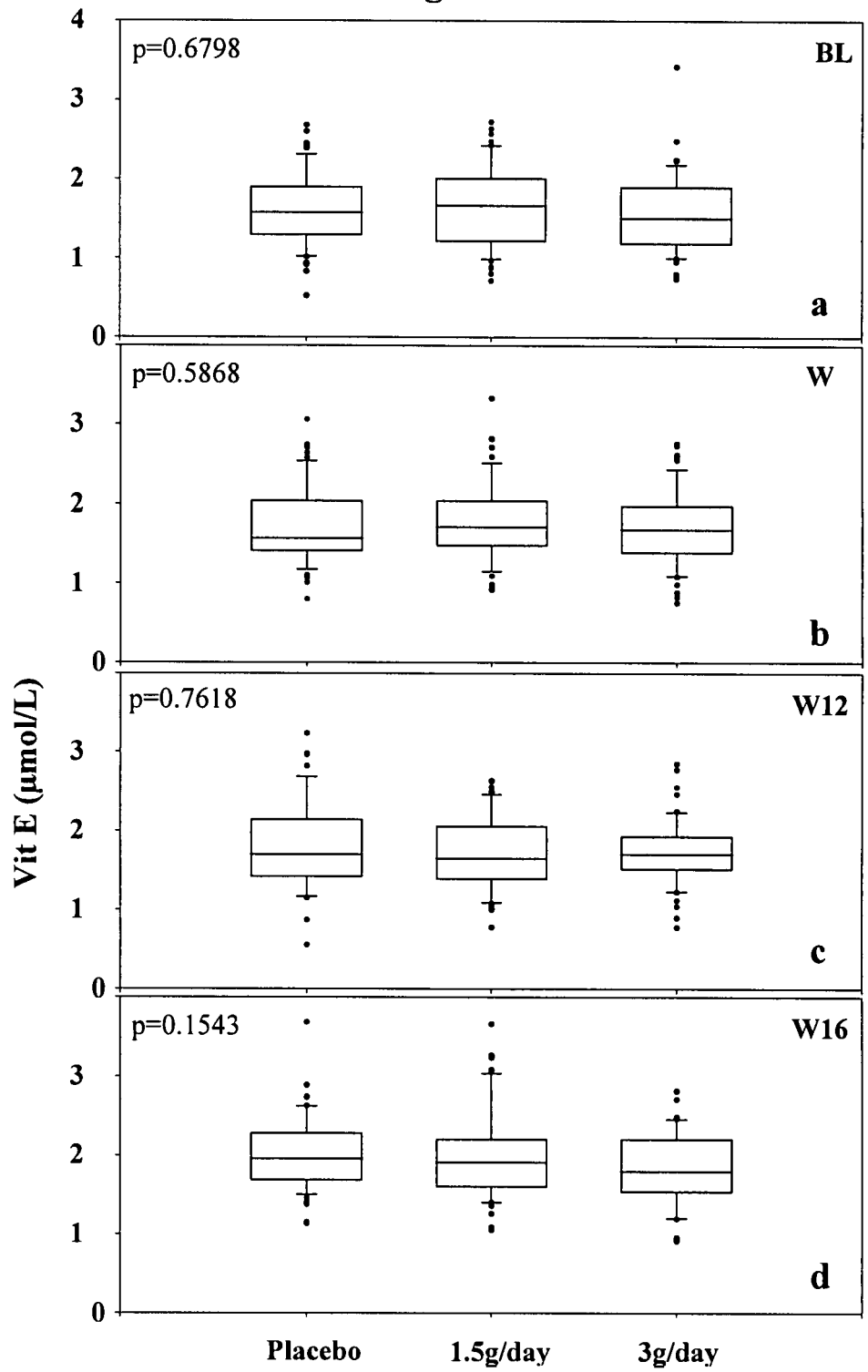
FIG. 5 shows levels of vitamin E in three groups ingesting different levels of a CAS after different time periods.

Results for serum Vit E levels in the study subjects are presented in Table 8 below. The baseline serum levels of Vit E were also comparable (P=0.6798) for groups of the placebo (16.07±4.74 µmol/L), the low dose (16.40±5.08 µmol/L), and the high dose (15.64±4.97 µmol/L) (FIG. 5a). No significance was found among groups of low dose (17.9±4.99 µmol/L), high dose (17.08±4.83 µmol/L) and the placebo (17.32±4.97 µmol/L) in 1 month samples (P=0.5868) (FIG. 5b). No significance was found among groups of low dose (17.03±4.71 µmol/L), high dose (17.33±4.21 µmol/L), and the placebo (18.01±6.29 µmol/L) in 3 months samples (P=0.7618) (FIG. 5c). Furthermore, levels of Vit E (P=0.1543) were not statistically significant among the treated groups and the placebo group in samples collected at 1 month after the trial (FIG. 5d).

TABLE 8

Vit E levels (µmol/L) in three groups at different time points

| Group | N | Mean | Median | SD |
|---|---|---|---|---|
| 3.0 g/day, BL | 58 | 15.641 | 15.091 | 4.968 |
| 3.0 g/day, W4 | 57 | 17.076 | 16.842 | 4.830 |
| 3.0 g/day, W12 | 53 | 17.326 | 17.012 | 4.208 |
| 3.0 g/day, W16 | 52 | 18.410 | 17.983 | 4.82 |
| 1.5 g/day, BL | 57 | 16.400 | 16.624 | 5.080 |
| 1.5 g/day, W4 | 56 | 17.900 | 17.146 | 4.990 |
| 1.5 g/day, W12 | 51 | 17.026 | 16.449 | 4.714 |
| 1.5 g/day, W16 | 51 | 20.180 | 19.148 | 5.721 |
| Placebo, BL | 55 | 16.065 | 15.771 | 4.736 |
| Placebo, W4 | 57 | 17.324 | 15.667 | 4.967 |
| Placebo, W12 | 54 | 18.010 | 16.998 | 6.286 |
| Placebo, W16 | 54 | 20.168 | 19.566 | 4.608 |

BL (baseline),
W4 (week 4),
W12 (week 12),
W16 (week 16)

The results show that dietary intervention with NS clay over a period of 3 months did not significantly influence the levels of Vit A and Vit E in the serum of study participants. These results indicate that NS intervention in a population at high risk for aflatoxicosis (and potentially malnourished) will not interfere with the utilization of these important micronutrients.

Example 5

To further evaluate the influence of NS on humans, concentrations of minerals (classified as nutrient and non-nutrient) were measured in serum samples of subjects in the phase 2a clinical trial carried out in Example 3 above at the beginning and end of the study. Nutrient minerals included: Cu, Fe, K, Mg, Na, P, S, Zn, Co, Cr, Mn, Mo, Ni and Se. Non-nutrient minerals included: Ag, Al, As, Ba, Be, Cd, Hg, Li, Pb, Sb, Sr, Ti, Tl, U, and V. The individuals in the study included 177 healthy Ghanaian volunteers who either received 1.5 g NS/day (low dose), 3.0 g NS/day (high dose), or placebo for 3 months.

Analysis of trace minerals in human serum samples were measured as follows. Serum samples (approximately 0.45 g) were mixed with 200 ml of concentrated nitric acid in a 15 ml centrifuge tube and heated overnight at 90° C. and cooled. Then 100 ml of 30% $H_2O_2$ was added and the samples were heated at 70° C. for one hour and cooled; then 50 ml of concentrated hydrochloric acid was added and the samples were heated at 70° C. for one hour and cooled; then the samples were brought to a final volume of 10 ml with purified water. Mercury (Hg) concentrations were determined by cold vapor atomic absorption (CVAA) using an M-7500 (Cetac Technologies, Omaha, Nebr.) with stannous chloride as a reductant. Aluminum (Al), boron (B), barium (Ba), beryllium (Be), calcium (Ca), cobalt (Co), copper (Cu), iron (Fe), potassium (K), magnesium (Mg), molybdenum (Mo), sodium (Na), phosphorus (P), sulfur (S), silicon (Si), strontium (Sr), titanium (Ti), vanadium (V), and zinc (Zn) were determined with an inductively coupled plasma-optical emission spectrometer (ICP-OES) using a CirOS (Spectro Analytical Instruments, Fitchburg, Mass.) with axial viewing and ytterbium (Yb) as an internal standard. Silver (Ag), arsenic (As), cadmium (Cd), chromium (Cr), manganese (Mn), nickel (Ni), lead (Pb), selenium (Se), and thallium (Tl) were determined with an inductively coupled plasma-mass spectrometer (ICP-MS) using an Elan 6100 (Perkin-Elmer, Wellesley, Mass.) with As, Cr, Mn, and Se acquired in DRC mode, and bismuth (Bi), gallium (Ga), and rhodium (Rh) as internal standards. In addition to blanks, spiked blanks, duplicate samples, and spiked samples, standard reference materials (Seronorm, Billingstad, Norway) were prepared and analysed with each batch of samples, to verify results. The results are shown in Tables 9 and 10 below.

TABLE 9

Analysis of non-nutritional minerals in serum samples of study subjects: Baseline levels vs. High Dose of NS at the end of the trial

| Minerals | Before Trial | After Trial |
|---|---|---|
| Ag (Silver) (µg/L) | 0.23 ± 0.03 | 0.26 ± 0.27 |
| Al (Aluminum) (µg/L) | 132.08 ± 71.92 | 130.17 ± 73.56 |
| As (Arsenic) (µg/L) | 8.83 ± 1.45 | 8.63 ± 1.63 |
| Ba (Barium) (µg/L) | 80.07 ± 15.23 | 115.92 ± 32.89* |
| Be (Beryllium) (µg/L) | 1.11 ± 0.06 | 1.11 ± 0.12 |
| Cd (Cadmium) (µg/L) | 0.70 ± 0.38 | 0.71 ± 0.39 |
| Hg (Mercury) (µg/L) | 5.57 ± 0.30 | 5.60 ± 0.60 |
| Li (Lithium) (µg/L) | 22.30 ± 1.15 | 22.37 ± 2.44 |
| Pb (Lead) (µg/L) | 16.13 ± 8.55 | 15.03 ± 9.25 |
| Sb (Antimony) (µg/L) | 1.11 ± 0.01 | 1.13 ± 0.15 |
| Sr (Strontium) (µg/L) | 71.50 ± 18.47 | 99.94 ± 28.24* |
| Ti (Titanium) (µg/L) | 111.43 ± 6.00 | 111.91 ± 12.08 |
| Tl (Thallium) (µg/L) | 0.24 ± 0.06 | 0.25 ± 0.20 |
| U (Uranium) (µg/L) | 0.24 ± 0.12 | 0.22 ± 0.02 |
| V (Vanadium) (µg/L) | 11.14 ± 0.60 | 11.19 ± 1.21 |

*$P < 0.01$

TABLE 10

Analysis of nutritional minerals in serum samples of study subjects: Baseline levels vs. High Dose of NS at the end of the trial

| Minerals | Before Trial | After Trial |
|---|---|---|
| Ca (calcium) (mg/L) | 91.99 ± 4.77 | 95.17 ± 6.27 |
| Cu (Copper) (mg/L) | 1.33 ± 0.33 | 1.27 ± 0.22 |
| Fe (Iron) (mg/L) | 1.32 ± 0.60 | 1.33 ± 0.44 |
| K (Potassium) (mg/L) | 218.77 ± 24.15 | 192.70 ± 19.27 |
| Mg (Magnesium) (mg/L) | 18.36 ± 1.56 | 19.47 ± 1.73 |
| Na (Sodium) (mg/L) | 3113.33 ± 74.28 | 3183.50 ± 134.93 |
| P (Phosphorous) (mg/L) | 108.93 ± 12.82 | 115.12 ± 15.98 |
| S (sulfur) (mg/L) | 1224.50 ± 77.62 | 1276.67 ± 105.04 |
| Zn (Zinc) (mg/L) | 1.28 ± 0.44 | 1.36 ± 0.37 |
| Co (Cobalt) (µg/L) | 1.35 ± 0.96 | 1.35 ± 0.83 |
| Cr (Chromium) (µg/L) | 6.57 ± 7.95 | 6.16 ± 3.36 |
| Mn (Manganese) (µg/L) | 5.84 ± 6.04 | 5.81 ± 8.30 |
| Mo (Molybdenum) (µg/L) | 16.32 ± 4.68 | 22.23 ± 11.58 |
| Ni (Nickel) (µg/L) | 18.05 ± 7.70 | 18.16 ± 6.32 |
| Se (Selenium) (µg/L) | 116.50 ± 22.06 | 124.57 ± 23.41 |

No significant differences were found in the levels of most of the analyzed minerals, except for calcium, potassium and molybdenum. Serum Ca and K levels were within the normal range. The normal range values for Mo were not available. Serum barium and strontium were the only non-nutritional metals that were significantly increased at the end of the study. It is difficult to evaluate the elevation of these divalent cations because no clinical reference is available. Both strontium and barium are naturally present in food and water; the levels of Sr and Ba contained in a 3 g (high) dose of NS clay are well below the extrapolated TDI for foods. In conclusion, the results of these studies support the prospect of using NS clay in the diet of humans to block, or significantly diminish exposure to AFs and to prevent the adverse effects of AFs in humans consuming AFs-contaminated grains. Moreover, framework minerals such as Al are not significantly bioavailable from the stomach and intestinal tract. The only minerals that were significantly increased from NS clay exposure were Ba and Sr, and the normal range of clinical reference for these metals are not available.

Example 6

The amount of dioxin present in CASAD clay containing a variety of particle sizes and the amount of dioxin present in CASAD clay after being sized to contain only particles less than 80 microns was measured as previously described. Prior to sizing, the CASAD clay contained the amounts of dioxin shown in Table 11 below.

TABLE 11

| Analyte | Concentration Found (pg/L) | Detection Limit (pg/L) |
|---|---|---|
| 2,3,7,8-TCDD | — | 0.024 |
| 1,2,3,7,8-PeCDD | — | 0.025 |
| 1,2,3,4,7,8-HxCDD | — | 0.039 |
| 1,2,3,6,7,8-HxCDD | — | 0.044 |
| 1,2,3,7,8,9-HxCDD | — | 0.042 |
| 1,2,3,4,6,7,8-HpCDD | 0.121 | 0.043 |
| OCDD | 1.243 | 0.108 |
| Total Tetra-Dioxins | 1.284 | 0.024 |
| Total Penta-Dioxins | 1.820 | 0.025 |
| Total Hexa-Dioxins | 1.994 | 0.039 |
| Total Hepta-Dioxins | — | 0.043 |

As shown in Table 11, CASAD clay prior to sizing contained 0.121 pg/L of hepta-chlorodibenzo-p-dioxin (1,2,3,4,6,7,8-HpCDD) and 1.243 pg/L of octa-chlorodibenzo-p-dioxin (OCDD). In addition, the total tetra-dioxins were measured at 1.284 pg/L, the total penta-dioxins were measured at 1.820, and the total hexa-dioxins were measured at 1.994. The other dioxins tested were either absent or at a level below the detection limit of the testing apparatus. The CASAD clay was then sized so that it contained only particles less than 80 microns in size. The same analysis of dioxin content was performed. The results are shown in Table 12 below.

TABLE 12

| Analyte | Concentration Found (pg/L) | Detection Limit (pg/L) |
|---|---|---|
| 2,3,7,8-TCDD | — | 0.024 |
| 1,2,3,7,8-PeCDD | — | 0.025 |
| 1,2,3,4,7,8-HxCDD | — | 0.039 |
| 1,2,3,6,7,8-HxCDD | — | 0.044 |
| 1,2,3,7,8,9-HxCDD | — | 0.042 |
| 1,2,3,4,6,7,8-HpCDD | — | 0.043 |
| OCDD | 0.362 | 0.108 |
| Total Tetra-Dioxins | — | 0.024 |
| Total Penta-Dioxins | — | 0.025 |
| Total Hexa-Dioxins | — | 0.039 |
| Total Hepta-Dioxins | — | 0.043 |

The results show that dioxin content is greatly reduced in CASAD clay having a particle size less than 80 microns. The only remaining detected dioxin was octa-chlorinated dioxin (OCDD), at a reduced amount of 0.362 pg/L.

Example 7

Aflatoxins (AFs), produced predominantly by *Aspergillus flavus* and *Aspergillus. Parasiticus*, represent a group of naturally occurring fungal metabolites (mycotoxins) that have long been recognized as hazardous contaminants of food. Aflatoxin $B_1$ ($AFB_1$) is hepatotoxic and genotoxic, and has been categorized as a known human carcinogen (Group I). Acute exposure to high levels of $AFB_1$, via the diet causes disease (aflatoxicosis) and death in humans, as evidenced by numerous reports, including the recent outbreak in Kenya. Chronic exposure to low levels of AFs is one of the major risk factors in the etiology of human hepatocellular carcinoma (HCC) in several regions of Africa and Southeast Asia. Importantly, $AFB_1$, has also been shown to be a potent immunotoxic agent in animals and humans. Therefore, development and application of practical and highly effective intervention strategies and therapies for aflatoxicoses are critical for improving human health, especially in high-risk populations.

Humans and animals (for centuries and on most continents) have been reported to eat clay minerals (geophagy). The reasons for this behavior are generally ill-defined, but clay eating is usually perceived to be beneficial and safe. For example, Clay eating by people in close contact with nature is very common, and in many parts of South America and Africa, the dietary use of clay is culturally acceptable. NovaSil clay (NS) is a naturally-occurring and heat processed calcium montmorillonite that is commonly used as an anticaking additive in animal feed. Previous research has shown that NS is a selective enterosorbent for aflatoxins when included in the diet at levels up to 0.5% (weight to weight) in animal models. NS significantly protected a variety of young animals from aflatoxicosis, including chicks, turkey poults, pigs, lambs, and rodents. In addition, NS also reduced AF residues in milk from dairy cows and goats, as well as biomarkers of AF exposure in rodents. Mechanistically, NS decreases the uptake of AF in the gastrointestinal tract, leading to significantly reduced AF exposure and subsequent toxicity. Information derived from equilibrium adsorption isotherms and molecular modeling studies has indicated that NS has a preference for AFs containing a planar ketolactone system.

No observable adverse effects have been reported in short-term animal studies following the addition of NS to the diet. No maternal or fetal toxicity was found in Sprague-Dawley (S-D) rats ingesting NS at dietary concentrations as high as 2.0% throughout pregnancy. In addition, no significant changes in trace metal bioavailability were found in a variety of maternal or fetal tissues. In a chronic study, S-D rats treated with 0.25-2.0% NS clay in the diet over a six-month period did not exhibit dose-dependent adverse effects on body weight gains, feed conversion ratios, relative organ weights, gross and histological appearance of major organs, and hematological and serum biochemistry parameters. Also, essential nutrient levels including vitamins A and E, Fe, and Zn were unaffected.

Given the safety and efficacy of NS in multiple animal models, as well as its low cost, NS inclusion may be especially beneficial in the diets of humans that are at high risk for aflatoxicosis in developing countries. Initially, a two-week phase I clinical trial in healthy volunteers showed that daily intake of NS up to 3 g/day had no significant adverse effect on human subjects. Based on the findings from this study, a 3-month randomized, double-blinded, and placebo controlled phase IIa intervention trial was carried out in 180 Ghanaians who were exposed to AFs from their diet. In this example, the efficacy of NS intervention was evaluated by analyzing biomarkers in serum and urine samples collected prior to the study (baseline), at 1-month and 3-month of the intervention, and at 1-month post intervention. Results of this study support the prospect of using NS in the diet of humans to block, or significantly diminish exposure to AFs and to prevent the adverse effects of AFs in humans consuming AF-contaminated foods.

[$^3$H]-AFB$_1$ (28 Ci/mmol) was purchased from Moravek Biochemicals (Brea, Calif., USA). Standard AFB$_1$, M$_1$ and radioimmunoassay reagents were obtained from Sigma (St. Louis, Mo., USA). Monoclonal antibody 2B11 was kindly provided by Dr. G. N. Wogan at MIT.

Immunoaffinity columns were purchased from VICAM (Watertown, Mass., USA). NS clay was originally obtained from Engelhard Chemical Corporation (Iselin, N.J., USA), and was further examined for potential environmental contaminants including polychlorinated dibenzo-p-dioxins/furans (PCDDs/PCDFs) and heavy metals to insure compliance with federal and international standards, as previously described in detail (Afriyie-Gyawu et al., 2007; Wang et al., 2005). NS capsules were prepared at College Pharmacy, Colorado Springs, Colo. under sterile conditions according to good manufacturing practices (GMP). All of the capsules including the matching placebo were of the same size, shape and color. All other chemicals and reagents used were obtained commercially at the highest purity available unless otherwise specified.

Four communities from the Ejura-Sekyedumase district (ESD) and two communities from the Ejura sub-district were selected for screening of study subjects. These two districts belong to the Ashanti Region in Ghana, where approximately 76% of the populace engages predominantly in agriculture. Crops grown in this area mainly include maize, groundnuts, yams, cassava, cotton, and tobacco. AF exposure data and demographic information were established in 4 of these communities prior to this study (Jolly et al., 2006).

Figure 6:
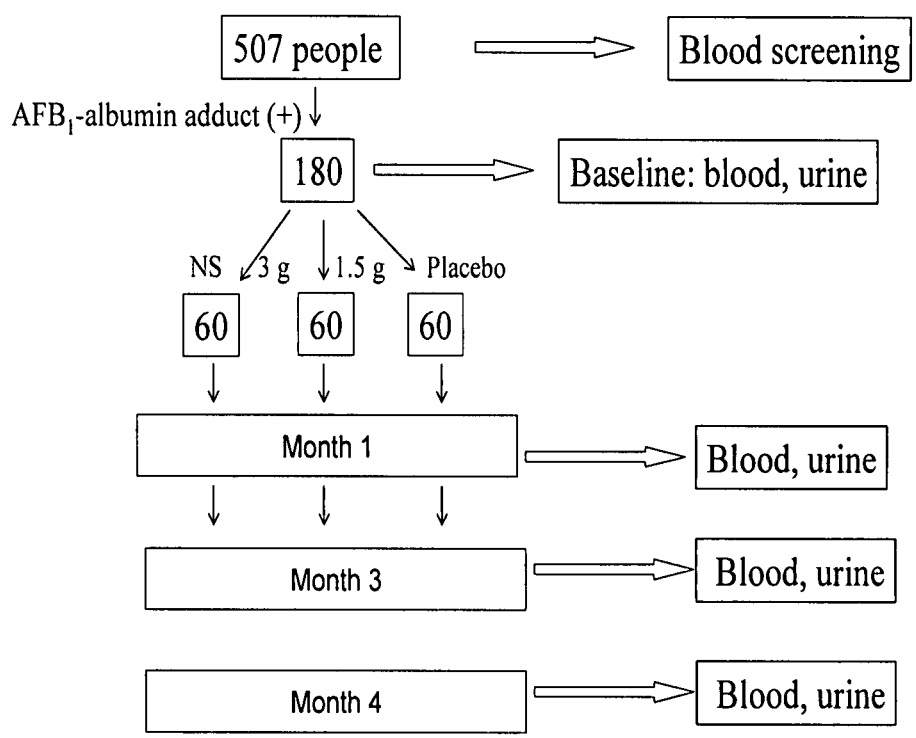
FIG. 6 shows an overall study design of a NS intervention trial.

The trial was initiated in September, 2005 and was completed in April, 2006. The overall study design followed the guidelines for a randomized, double-blinded, placebo controlled Phase II clinical trial as previously described in examples above. Study protocol was approved by the Institutional Review Board at Texas A&M University and the Noguchi Memorial Institute for Medical Research Institutional Review Board for Ethical Clearance in Ghana. FIG. 6 shows a flow chart of the overall study design and sample collection procedure. Briefly, 180 subjects were recruited from a total of 507 screened volunteers who met the following criteria: informed consent; serum AFB$_1$-albumin adduct levels>0.5 µmol AFB$_1$/mg albumin; age 18-58 yr; healthy status based on physical examination results, hematological parameters, liver and renal function indicators, and no history of chronic disease(s); no use of prescribed medications for chronic or acute illness; and non-pregnant and/or non-breastfeeding for females. These participants were randomly assigned to one of three groups: 3.0 g, 1.5 g, and the placebo and took 2 capsules containing either 500 mg NS, 250 mg NS, or 250 mg placebo 3 times/day (before meals and with at least 100 ml of water) over a period of 3 months. Dose selection was based on the efficacy and safety of NS demonstrated in previous animal studies (Phillips et al., 1999; Phillips et al., 2002, 2006) and dosimetry data from a short-term human study in the USA (Wang et al., 2005). Blood and urine samples were collected from each study participant at the beginning of the study (baseline), at 1-month and 3-months of intervention, and at 1-month following the end of the trial. Serum, plasma and blood cells were immediately separated and stored at −20° C. Morning urine samples were collected, measured for volume, and 50 mL aliquots were stored at −20° C. Aliquots of each sample were shipped frozen to Texas A&M University and Texas Tech University for biomarker analysis. The laboratory personnel who performed the analyses were blinded to sample sources.

Serum AFB$_1$-albumin adducts were measured by a quantitative RIA procedure (Wang et al., 1996) Briefly, serum samples were concentrated and resuspended in phosphate buffered saline (PBS). Serum albumin was quantified by a bromocresol purple dye binding method (Sigma, St. Louis, Mo., USA), and the amount of total protein was determined using the Bradford procedure (Pierce Biotechnology Inc., Rockport, Ill., USA). Subsequently, total protein was digested with Pronase (Calbiochem, La Jolla, Calif., USA) and the digests were extracted with acetone. AFB$_1$-albumin adducts were quantified with the RIA procedure in duplicate serum protein digests each containing 2 mg protein. Pooled normal human serum standards (Sigma, St. Louis, Mo., USA) were used to determine nonspecific inhibition in the assay. A nonlinear regression method (Gange et al., 1996) was used to establish the standard curve for the RIA. Concentrations of AFB$_1$-albumin adducts were expressed as amount of AFB$_1$ per mg albumin. The detection limit of the assay was 0.01 µmol/mg albumin.

AFM$_1$ levels in urine samples were analyzed with immunoaffinity column purification followed by HPLC-fluorescence detection described by Groopman et al. (Groopman et al., 1992), with modifications of Sarr et al. (Sarr et al., 1995) and Wang et al. (Wang et al., 1999). Briefly, each of the urine samples (5.0 ml) was adjusted to an acidic pH with 0.5 ml of 1.0 M ammonium formate (pH 4.5), and the volume was increased to 10 ml with water and vortexed. The sample was then loaded on a 1 ml preparative Aflatest P immunoaffinity column (VicamLP, Watertown, Mass., USA) at a flow rate of approximately 0.3 ml/min as described previously (Wang et al., 1999). After washing, the purified AF fraction was eluted with 80% methanol and dried under N$_2$ for analysis using a Waters HPLC system (Waters Corporation, Milford, Mass.) with fluorescence detection capabilities. A 250 mm×4.6 mm LiCrospher RP-18 endcapped column with a pore size of 100 Å and a particle size of 5 µm (Alltech Associates, Deerfield, Ill., USA) was used to resolve AF metabolites. The mobile phase consisted of 22% ethanol in water which was buffered with 20 mM ammonium formate (pH 3.0). Chromatographic separation of AFs was achieved by isocratic elution of the mobile phase for 20 min. Samples were injected (100 µl) on the column and the elution rate was 1.0 ml/min. The AFM$_1$ peak was detected at a retention time of approximately 15.4 min. The limit of detection for this method was 10 pg/ml of urine for AFM$_1$. Urinary concentrations of $AFM_1$ were expressed as pg/mg creatinine in order to correct for variations in urine dilution among individual samples.

All of the data generated were stored in an Excel database and analyzed with SAS software version 9.3 (SAS Institute Inc., Cary, N.C.). Median, mean, standard deviations (SD) and range were calculated for concentrations of $AFB_1$-albumin adduct and $AFM_1$ and the values were expressed as median and mean±SD unless otherwise stated. To assess the efficacy of NS intervention, the statistical evaluation focused on the comparisons among different treatment levels and different time points. To the parameters that were normally distributed, two-factorial ANOVA and Bonfferoni procedures were used to compare significant differences between means of different treatment arms and times. To the parameters that were not normally distributed, the Kruskal-Wallis test or Wilcoxon rank sum test were used to compare the differences among different treatment groups and different time points. To evaluate the effect of dose and time interactions on NS treatment, a nonparametric mixed-effect model was applied as previously described (Brunner et al., 2002). A P value of less than 0.05 (two-tailed) was considered significant.

A total of 180 subjects were recruited for this intervention trial with NS and treatment was initiated in 177 subjects. The overall adherence among the participants and sample availability for biomarker analyses were satisfactory. A total of 162 subjects (91.5%) completed the 3-month trial. Detailed information about the numbers of samples at each time collection, for analyses of $AFB_1$-albumin adducts in serum and $AFM_1$ levels in urine are listed in Table 13 below. Among the 4 time points of sample collection, >95% blood and >90% urine samples were collected from participants; this validated our use of $AFB_1$ biomarkers of exposure for the delineation of NS efficacy.

TABLE 13

| Treatment group | Sample No. | | | |
|---|---|---|---|---|
| | Baseline | 1-month | 3-month | 4-month |
| Serum | | | | |
| Placebo | 55 | 56 | 54 | 54 |
| NS 1.5 g | 57 | 56 | 52 | 51 |
| NS 3.0 g | 59 | 57 | 53 | 52 |
| Urine | | | | |
| Placebo | 53 | 52 | 55 | 54 |
| NS 1.5 g | 53 | 53 | 51 | 43 |
| NS 3.0 g | 53 | 52 | 53 | 52 |

Figure 7:
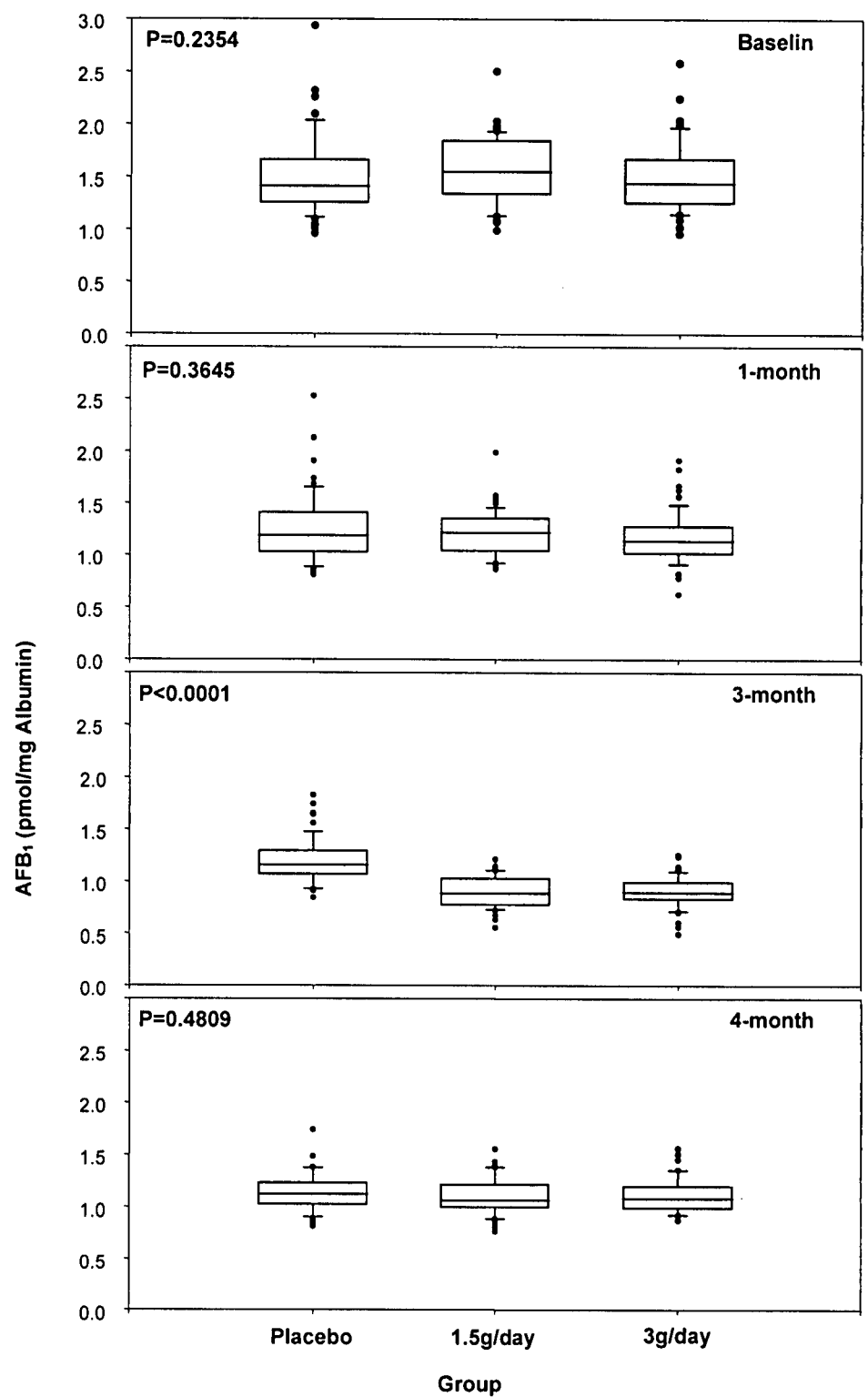
FIG. 7 shows the dose effects of NS intervention on serum $AFB_1$-albumin adduct levels.
Figure 8:
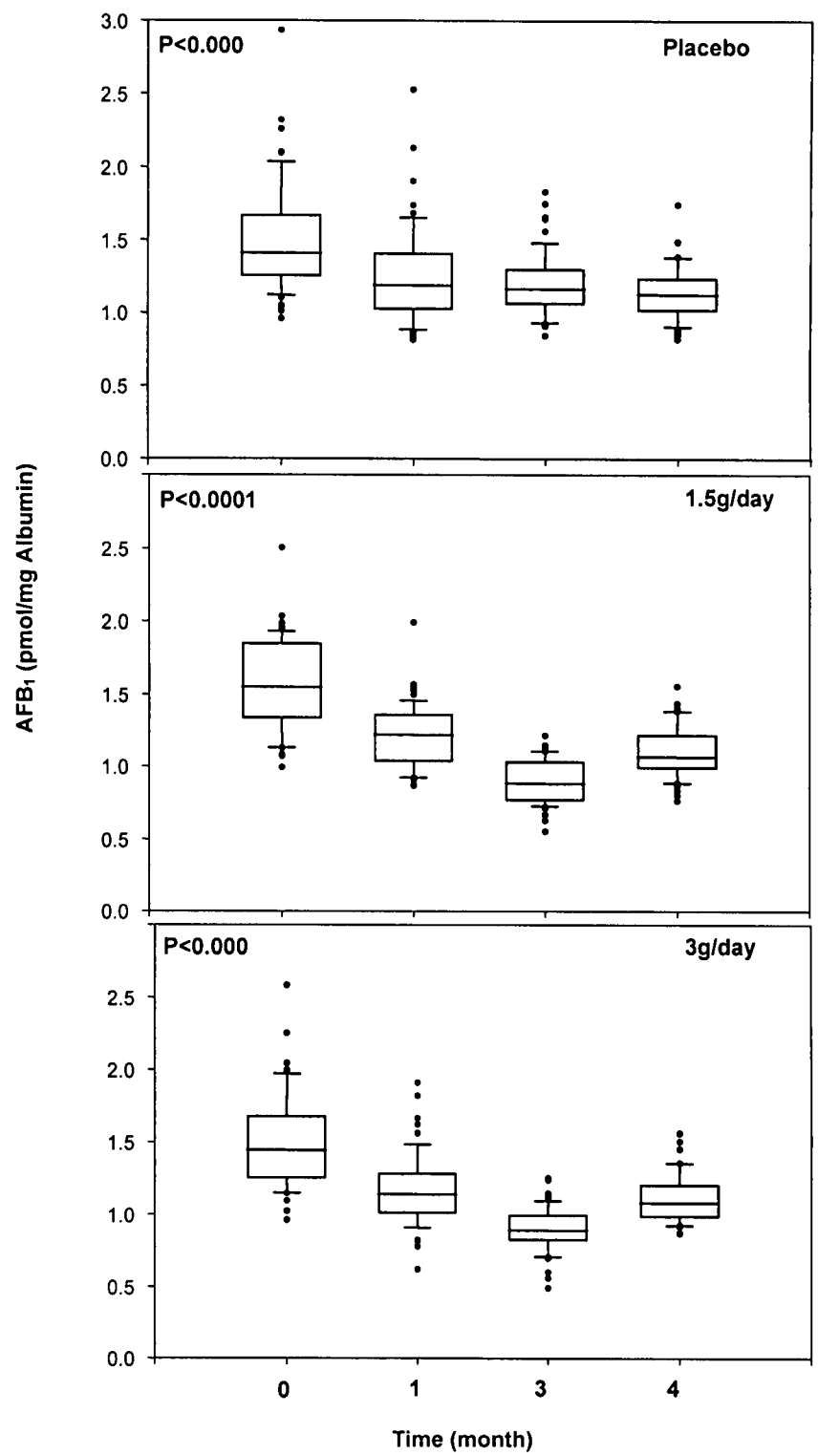
FIG. 8 shows the time effects of NS intervention on serum $AFB_1$-albumin adduct levels.

A total of 656 serum samples collected over a 4-month study period were analyzed for $AFB_1$-albumin adducts. Average levels (mean±SD) and the range of serum $AFB_1$-albumin adducts in three study groups (placebo, 1.5 g NS, and 3 g NS) at different time points are shown in Table 14 below. The distributions of overall $AFB_1$-albumin adduct levels in these three groups throughout the study duration are shown in FIGS. 7 and 8. The boxplots show distributions of $AFB_1$-albumin adduct levels in each group at each time point. The box values ranged from 25 to 75 percentile of the total samples, the line within it indicating the median value. The bars on both sides of a box represent values ranging from 5 to 25 percentile and from 75 to 95 percentile, respectively. High $AFB_1$-albumin adduct levels were observed in baseline samples, and there were no significant differences among groups (P=0.2354). No statistically significant differences were observed in $AFB_1$-albumin adduct levels among the three study groups at 1-month after the NS intervention (P=0.3645). However, statistically significant decreases in $AFB_1$-albumin adduct levels were observed at 3-months after the intervention in both the 1.5 g NS and 3 g NS groups (P<0.0001) as compared to the placebo group. No statistically significant differences in $AFB_1$-albumin adduct levels were found among the 3 groups at 4-months, which was one month post intervention. As shown in FIG. 8, significant decreases in adduct levels were seen in all three treatment groups over the 4-month study period, showing a significant time effect on the $AFB_1$-albumin adduct level. However, the pattern of time effect was different between the NS treated groups and the placebo group. For the placebo group, the reduction rate of $AFB_1$-albumin adduct at 1- and 3-months after the intervention was 16.1% and 19.9%. For the 1.5 NS and 3.0 NS groups, the reduction rates of $AFB_1$-albumin adduct levels were 22.3% and 22.4% at 1-month after the intervention and were 42.8% and 40.2% at 3-months after the intervention, respectively. There were no consistent changes in the placebo groups between 3-months and 4-months; however, levels of serum $AFB_1$-albumin adduct increased significantly in the two intervention groups and were back to levels comparable to those of the placebo group at 4-months. Non-parametric mixed-effect model analysis further showed significant effects of dose, time, and dose-time interaction for reducing serum $AFB_1$-albumin adduct levels, and this reduction was attributable to the NS intervention (Table 16 below).

TABLE 14

| Treatment group | $AFB_1$-albumin adducts (pmol/mg Albumin)* | | | |
|---|---|---|---|---|
| | Baseline | 1-month | 3-month | 4-month |
| Placebo | 1.493 ± 0.375 (0.961-2.934) | 1.253 ± 0.335 (0.810-2.528) | 1.195 ± 0.216 (0.839-1.829) | 1.137 ± 0.180 (0.815-1.739) |
| NS 1.5 g | 1.563 ± 0.315 (0.990-2.504) | 1.214 ± 0.215 (0.865-1.990) | 0.894 ± 0.155 (0.553-1.211) | 1.096 ± 0.178 (0.764-1.554) |
| NS 3.0 g | 1.505 ± 0.322 (0.960-2.584) | 1.168 ± 0.244 (0.621-1.911) | 0.900 ± 0.156 (0.491-1.251) | 1.116 ± 0.175 (0.867-1.560) |

*Data are presented in the format: mean ± SD (range).

Figure 9:
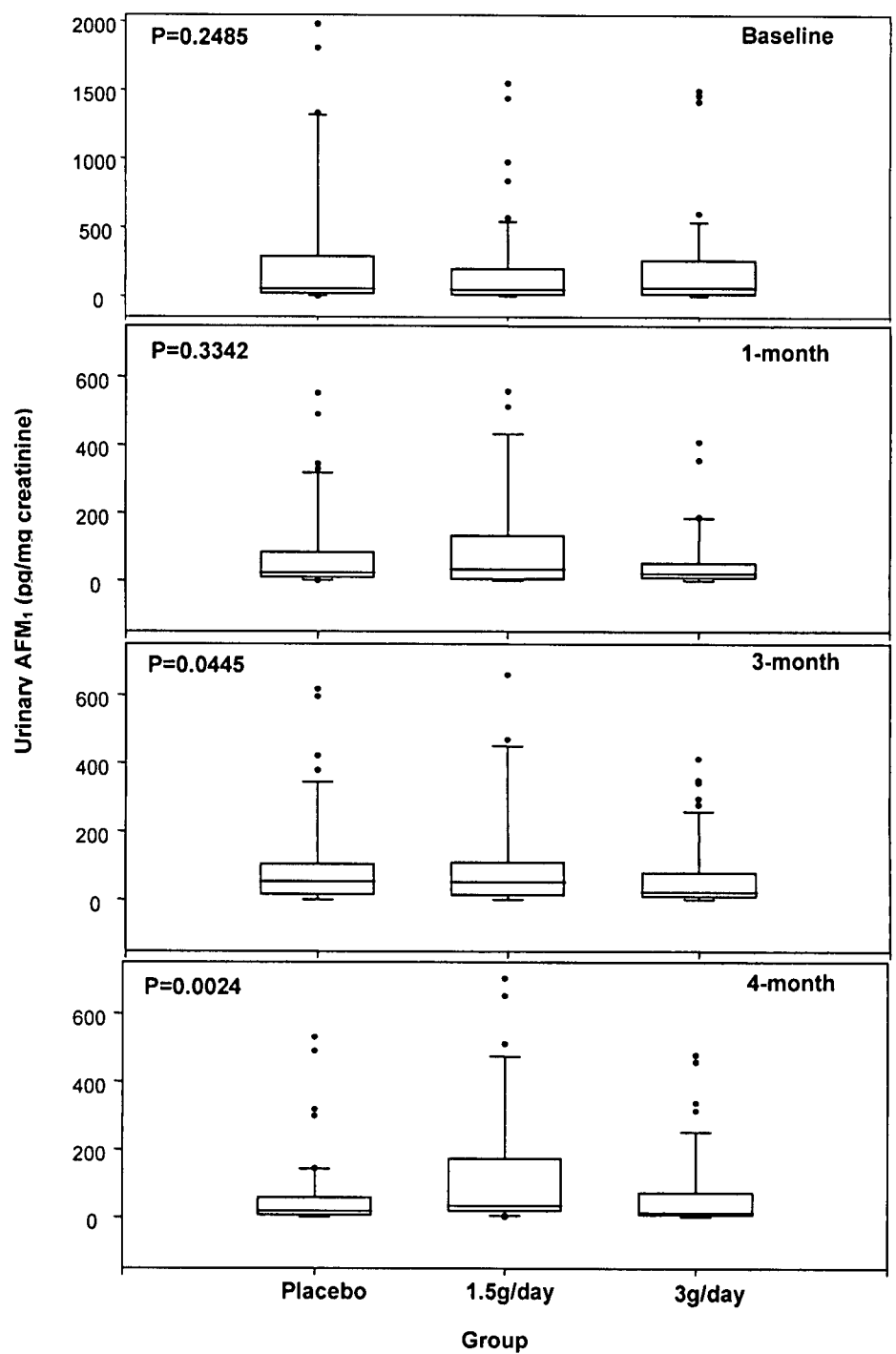
FIG. 9 shows the dose effects of NS intervention on urinary $AFM_1$ levels.
Figure 10:
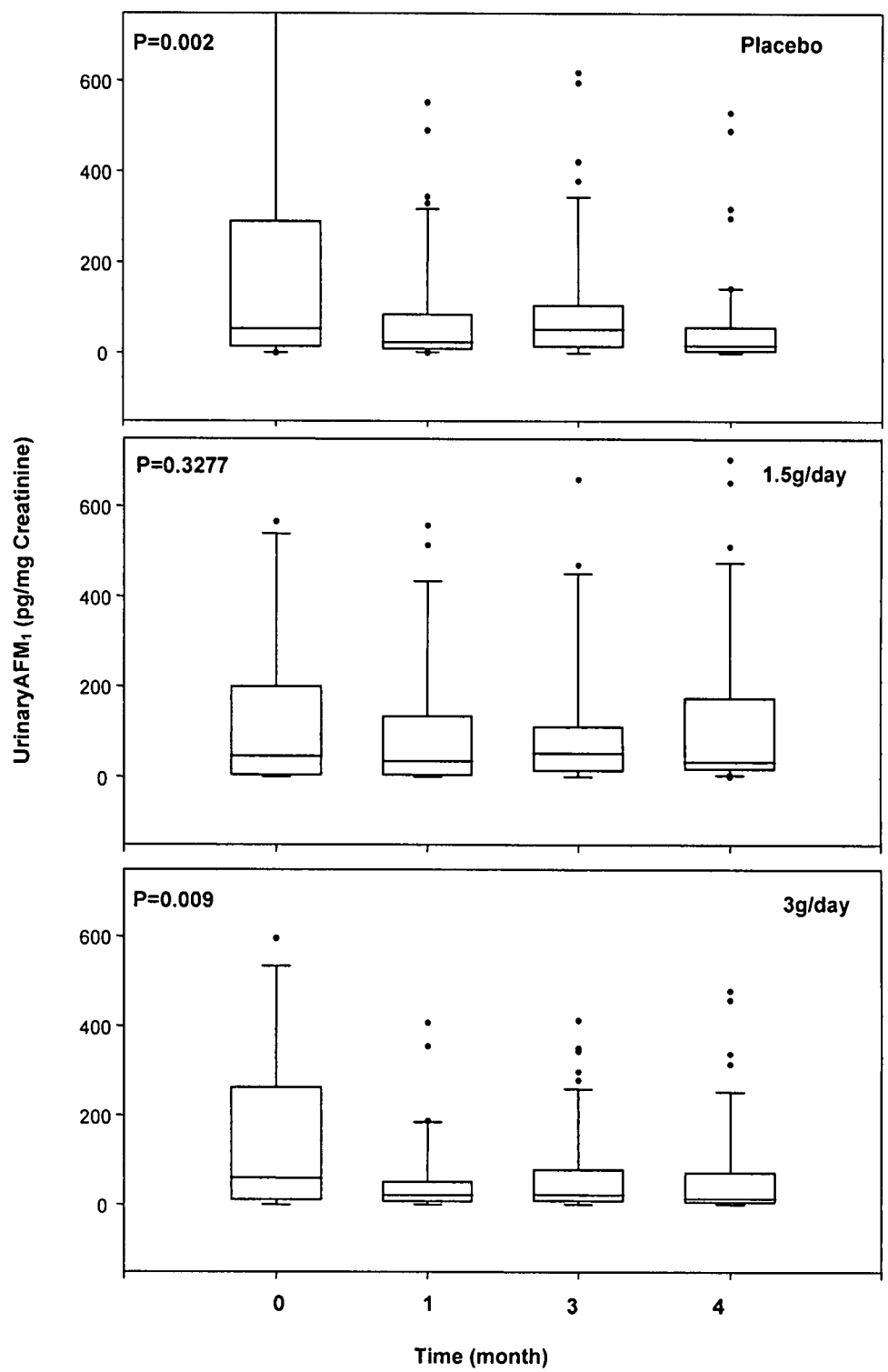
FIG. 10 shows the time effects of NS intervention on urinary $AFM_1$ levels.

A total of 624 urine samples over the 4-month study period were analyzed for $AFM_1$. Average levels and the range of $AFM_1$ in three study groups (placebo, 1.5 g NS, and 3 g NS) at different time points are presented in Table 15 below. The distribution of urinary $AFM_1$ levels in these three groups throughout the study duration are shown in FIGS. 9 and 10. The boxplots show distributions of $AFM_1$ levels in each group at each time point. The box values ranged from 25 to 75 percentile of the total samples, the line within it indicating the median value. The bars on both sides of a box represent values ranging from 5 to 25 percentile and from 75 to 95 percentile, respectively. Since the $AFM_1$ data is highly skewed, non-parametric analysis was applied for all statistical evaluations. There were no significant differences in median $AFM_1$ levels among the three study groups at baseline (P=0.2485). No significant differences were found in median $AFM_1$ levels among the three groups at 1-month after the NS intervention (P=0.3342). However, statistically significant decreases in median $AFM_1$ levels were observed at 3-months after the NS intervention (P=0.0445). Although the median $AFM_1$ level was comparable between the placebo group and the 1.5 g NS group (P=0.3951), a reduction rate of 58.7% in the median $AFM_1$ level was found between the 3 g NS group and the placebo group (P=0.0391). A reduction rate of 57.8% in the median $AFM_1$ level was also found between the 3 g NS group and the 1.5 g NS group (P=0.0219). Significant differences in median $AFM_1$ levels (P=0.0024) were also found among the three study groups at 4-months post intervention, which was mainly due to higher $AFM_1$ levels in the 1.5 g NS group. As shown in FIG. 10, significant decreases in $AFM_1$ levels were seen in the 3.0 g NS group over the 4-month study period, showing a significant time effect (P=0.009). Although a significant time effect was also noticed in the placebo group (P=0.002), levels of $AFM_1$ were highly variable, as shown by higher median levels at baseline and 3-months and lower median levels at 1-month and 4-months. No significant time effect for $AFM_1$ levels was found in the 1.5 g NS group over the 4-month study period (P=0.3277). Non-parametric mixed-effect model analysis also showed a significant dose-time interaction for reducing urinary $AFM_1$ levels, and this interaction was attributable to the NS intervention (Table 4).

adduct is also the most reliable molecular biomarker for studying human exposures to AFs. Highly significant associations between $AFB_1$-albumin adduct levels and $AFB_1$ intakes were found in human populations from several regions of the world. Furthermore, about 2% of the ingested $AFB_1$, is reported to be covalently bound to serum albumin, a value very similar to that observed when rats were administered $AFB_1$. Using various analytical techniques, $AFB_1$-albumin adduct was detectable in almost 100% of sera from adults and in 12-100% of sera from children in China and various African countries. In addition to studying AF exposure, $AFB_1$-albumin adduct has been used as a biological response indicator of acute and chronic aflatoxicosis in Africa, risk of HCC in Taiwan, China, and Africa, and infectious disease linked immune suppression. Moreover, $AFB_1$-albumin adduct has been regularly used as the surrogate efficacy biomarker for assessment of different agents and techniques in human intervention trials.

In this study, high levels of serum $AFB_1$-albumin adduct were observed in the participants at baseline before NS intervention (1.52±0.34 μmol/mg albumin; range: 0.96-2.93 μmol/mg albumin). These levels were higher than those

TABLE 15

| Treatment group | $AFM_1$ (pg/mg Creatinine)* | | | |
|---|---|---|---|---|
| | Baseline | 1-month | 3-month | 4-month |
| Placebo | 53.416 | 24.576 | 52.379 | 17.316 |
| | 644.224 ± 2026.527 | 94.709 ± 160.128 | 181.256 ± 675.903 | 56.837 ± 110.138 |
| | (0.018-13297.670) | (0.018-798.106) | (0.018-5006.335) | (0.018-529.405) |
| NS 1.5 g | 45.542 | 34.187 | 51.174 | 32.868 |
| | 183.582 ± 334.957 | 202.064 ± 639.731 | 307.080 ± 1248.346 | 358.585 ± 1594.004 |
| | (0.018-1547.390) | (0.018-4338.524) | (0.018-8878.776) | (0.018-10510.813) |
| NS 3.0 g | 60.266 | 20.989 | 21.609 | 12.221 |
| | 256.299 ± 615.168 | 175.094 ± 818.406 | 67.312 ± 102.544 | 70.392 ± 155.679 |
| | (0.018-3901.901) | (0.018-5882.708) | (0.018-411.681) | (0.018-873.717) |

*Data are presented in the format: median, mean ± SD (range).

Safety and efficacy are the two most important criteria for assessing potentially therapeutic and/or clinical intervention agents. The safety (and dosimetry) of NS has been well-documented in animal and human studies, including the 3-month trial in Ghana (Afriyie-Gyawu et al., 2007). The main objective of this study was to determine efficacy of NS in humans. The ability of NS to preferentially sorb AF in the stomach and intestines resulting in decreased AF bioavailability and toxicity has been clearly demonstrated in various animal models. Results from this study confirmed our work in animals and showed that administration of NS for 3 months significantly reduced serum $AFB_1$-albumin adduct levels and urinary $AFM_1$ levels in human subjects. To our knowledge, this is the first study to explore the efficacy and health benefits of dietary inclusion of NS clay by monitoring AF-specific biomarkers in a human population at risk for aflatoxicosis.

AF-specific biomarkers currently used in human and animal studies include $AFB_1$ metabolites and $AFB_1$-macromolecular adducts, i.e., $AFM_1$ in urine and $AFB_1$-albumin adducts in serum. The $AFB_1$-albumin adduct (compared to urinary AF metabolites) serves as a very important biomarker since its longer in vivo half-life may reflect integrated exposures over longer time periods. From a practical perspective pertinent to epidemiological studies, the measurement of serum $AFB_1$-albumin adducts offers a rapid and facile approach that can be used to screen very large numbers of people, e.g., 507 people (Afriyie-Gyawu et al., 2007) and other intervention studies. The $AFB_1$-albumin reported from the Gambia, Benin and the United Kingdom, and were comparable to levels found in populations at high-risk for liver cancer in China. Therefore, the study participants in Ghana represented a population at high risk for AF exposure. In this study, it was found that daily NS capsule administration produced significant dose- and time-effects in reduction of serum $AFB_1$-albumin adduct (Table 14). A significant (>40% reduction in $AFB_1$-albumin adduct levels) was observed at 3-months in both 1.5 g NS and 3 g NS intervention groups compared to the placebo group (Table 14 and FIG. 8). Although decreases in this biomarker level were also observed at 1-month after the intervention in two NS treatment groups, no significant differences were found, due to decreased adduct level in the placebo group. The delay in adduct reduction seen in this study was similar to a previous chemoprevention trial with Oltipraz in Qidong, China, in which a significant reduction of serum $AFB_1$-albumin adduct levels was observed only after the $5^{th}$ week of treatment. This delay is probably attributable to the long half-life of albumin, which is estimated to be approximately 3 weeks in normal and healthy people. Importantly, the $AFB_1$ bound to albumin ($AFB_1$-albumin adduct) may be stable for years. Similar findings were reported with oltipraz, where $AFB_1$-albumin adduct levels were detected until albumin turnover had passed three half-lives. The significant time-effect observed in this study, including the decrease in the placebo group, is also consistent with previous findings in the oltipraz trial and a recent education intervention study. In our current study, $AFB_1$-albumin adduct levels in both the 1.5 g NS and 3 g NS groups were elevated and went back to the placebo group level at the $4^{th}$ month, a month after the intervention, which further confirmed the efficacy of NS in reducing $AFB_1$ exposure from the diet.

$AFM_1$ is a metabolite of $AFB_1$ that is prevalent in urine and milk, and its formation from parent $AFB_1$ is catalyzed mainly by hepatic CYP1A2 in humans. The excretion of $AFM_1$ in urine represents recent $AFB_1$ exposure (i.e., within 24 or 48 hours). Thus, $AFM_1$ levels in urine are used as a short-term biomarker of $AFB_1$ exposure. Both serum $AFB_1$-albumin adduct and urinary $AFM_1$ have been extensively characterized and validated as biomarkers for $AFB_1$ exposure in many human populations. Levels of serum $AFB_1$-albumin adduct and $AFM_1$ excreted in human urine have shown significant correlation with dietary intake of AFs and with the risk of human HCC. Concurrent with reductions in serum $AFB_1$-albumin adduct levels at 3-months after the intervention, urinary $AFM_1$ levels were also significantly reduced in the 3 g NS group as compared to other treatment arms in this study (Table 15 and FIG. 9). A reduction rate of up to 58.7% in the median $AFM_1$ level found in the 3 g NS treatment group is comparable to the reduction rate of 55% in the median $AFB_1$—$N^7$-Guanine level after 3 months intervention with 100-mg chlorophyllin. The $AFB_1$—$N^7$-Guanine product is also a short-term biomarker like $AFM_1$. In this study, no significant effect in urinary $AFM_1$ levels was observed in the 1.5 g NS group, which is potentially due to considerable intra- and inter-individual variations in the measurement of a short-term biomarker. Significant time-effect of $AFM_1$ levels was also observed in all study groups, including the placebo group, which may reflect variations in daily dietary AF exposure levels (FIG. 10). Variations of urinary $AFM_1$ levels were also found in previous screening studies in a similar population in Ghana (Jolly et al., 2006) as well as other populations (Wang et al., 2001). The very wide range of $AFM_1$ levels (from undetectable up to 13.3 ng/mg creatinine) that were observed in our study participants suggests that genotypic or phenotypic variations of AF metabolizing enzymes, e.g. CYP1A2, may play a role in individual susceptibility to AF exposure. Nevertheless, in this study significant dose-time interaction effects (Table 16 below) associated with reduced urinary $AFM_1$ levels (and serum $AFB_1$-albumin adducts) confirmed the efficacy of NS administration by capsule.

TABLE 16

| Effect | Serum $AFB_1$-albumin adducts | Urinary $AFM_1$ |
|---|---|---|
| Dose | 7.890(p = 0.00043) | 2.234(p = 0.10715) |
| Time | 179.330(p = 0.00000) | 5.764 (p = 0.00067) |
| Dose * Time | 13.992(p = 0.00000) | 2.143 (p = 0.04950) |

In summary, the results of this study suggest that intervention with NS clay can effectively reduce AF exposure from contaminated diets, as represented by AF-specific biomarkers in blood and urine, i.e., $AFB_1$-albumin adduct and $AFM_1$. Long-term (phase IIb or phase III) studies will ultimately be required to further evaluate efficacy of NS intervention as an enterosorbent therapy for acute aflatoxicosis and for the prevention of chronic aflatoxin-induced disease when included in the diet of high risk populations.

One skilled in the art readily appreciates that this invention is well adapted to carry out the objectives and obtain the ends and advantages mentioned as well as those inherent therein. Thus, it should be evident that a composition of CAS in a capsule form and a tablet form are different, and these different forms of oral dosages can be used a method to prevent or treat poisoning and prevent aflatoxin-related liver cancer. Additionally, variations of the composition and methods are encompassed by the invention. For example, techniques may change as manufacturing of larger quantities of the composition are needed, such industrial scaling of composition production are understood to be within the spirit of the invention. The materials, methods, procedures and techniques described herein are presently representative of the preferred embodiments and are intended to be exemplary and are not intended as limitations of the scope. It is understood that one of ordinary skill in the art of pharmaceutical sciences would have available many pharmaceutical reference books, such as Remmington's Pharmaceutical Sciences $17^{th}$ Edition. Alfonso Gennaro editor, Mack Publishing Company Easton, Pa. 18042, that would allow one to modify and change formulations for the compositions and method of this invention. As such, changes therein and other uses will occur to those skilled in the art which are encompassed within the spirit of the invention or defined by the scope of the pending claims.

REFERENCES CITED

The following references, to the extent that they provide exemplary procedural or other details supplementary to those set forth herein, are specifically incorporated herein by reference.

U.S. PATENT DOCUMENTS

U.S. Pat. No. 5,178,832, issued to Phillips, et al., on Jan. 12, 1993, and titled "Selective Immobilization and Detection of Mycotoxins in Solution."

U.S. Pat. No. 5,165,946 issued to Taylor, et al., on Nov. 24, 1992, titled "Animal Feed Additive and Method for Inactivating Mycotoxins Present in Animal Feeds."

OTHER PUBLICATIONS

Remmington's Pharmaceutical Sciences $17^{th}$ Edition. Alfonso Gennaro editor, Mack Publishing Company Easton, Pa. 18042, Entire Book, pages 1-1983.

Remmington's Pharmaceutical Sciences $17^{th}$ Edition. Alfonso Gennaro editor, Mack Publishing Company Easton, Pa. 18042, Chapter 68, pages 1278-1321.

Remmington's Pharmaceutical Sciences 17th Edition. Alfonso Gennaro editor, Mack Publishing Company, Easton, Pa. 18042, Chapter 84, pages 1492-1517.

Harvey, R. B., D. E. Clark, W. E. Huff, L. F. Kubena, D. E. Corrier and T. D. Phillips: 1988. Suppression of serum iron binding capacity and bone marrow cellularity in pigs fed aflatoxin. Bull. Environ. Contam. Toxicol. 40:576 583.

Harvey, R. B., W. E. Huff, L. F. Kubena, D. E. Corrier and T. D. Phillips: 1988. Progession of aflatoxicosis in growing pigs. Am. J. Vet. Res. 49(4):482 487.

Phillips, T. D., L. F. Kubena, R. B. Harvey, D. R. Taylor and N. D. Heidelbaugh: 1988. Hydrated sodium calcium aluminosilicate: High affinity sorbent for aflatoxin. Poult. Sci. 67:243 247.

Harvey, R. B., W. E. Huff, L. F. Kubena, and T. D. Phillips: 1989. Evaluation of diets co-contaminated with aflatoxin and ochratoxin fed to growing pigs. Am. J. Vet. Res. 50:1400-1405.

Harvey, R. B., L. F. Kubena, W. E. Huff, D. E. Corrier D. E. Clark and T. D. Phillips: 1989. Effects of aflatoxin, deoxynivalenol, and their combinations in the diets of growing pigs. Am J Vet Res, 50(4):602 607.

Harvey, R. B., L. F. Kubena, T. D. Phillips, W. E. Huff and D. E. Corrier: 1989. Prevention of aflatoxicosis by addition of hydrated sodium calcium aluminosilicate to the diets of growing barrows. Am. J. Vet. Res. 50(3):416 420.

Harvey, R. B., L. F. Kubena, W. E. Huff, D. E. Corrier, G. E. Rottinghaus, and T. D. Phillips: 1990. Effects of treatment of growing swine with aflatoxin and T-2 toxin. Am. J. Vet. Res. 51:1688-1693.

Kubena, L., R. Harvey, W. Huff, D. Corrier, T. Phillips and G. Rottinghaus: 1990. Ameliorating properties of a hydrated sodium calcium aluminosilicate on the toxicity of aflatoxin and T-2 toxin. Poult. Sci. 69:1078-1086.

Kubena, L. F., R. B. Harvey, T. D. Phillips, D. E. Corrier and W. E. Huff: 1990. Diminution of aflatoxicosis in growing chickens by the dietary addition of a hydrated, sodium calcium aluminosilicate. Poult. Sci. 69:727-735.

Phillips, T. D., Afriyie-Gyawu, E., Wang, J.-S., Williams, J., Huebner, H. 2006. The potential of aflatoxin sequestering clay, D. Barug, D. Bhatnagar, H. P. van Egmond, J. W. van der Kamp, W. A. van Osenbruggen, A. Visconti, eds, In: The Mycotoxin Factbook, Wageningen Academic Publishers, The Netherlands, pp. 329-46.

Phillips, T. D., B. A. Sarr, B. A. Clement, L. F. Kubena and R. B. Harvey: 1990. Prevention of aflatoxicosis in farm animals via selective chemisorption of aflatoxin. In Mycotoxins, Cancer and Health (Pennington Center Nutrition Series, Vol. 1), pp. 223-228, Louisiana State University Press, Baton Rouge and London.

Phillips, T. D., B. A. Clement, L. F. Kubena and R. B. Harvey: 1991. Prevention of aflatoxicosis and aflatoxin residues with HSCAS. Vet. Human Toxicol. 32:15-19.

Harvey, R. B., L. F. Kubena, T. D. Phillips, D. E. Corrier, M. H. Elissalde and W. E. Huff: 1991. Diminution of aflatoxin toxicity to growing lambs by dietary supplementation with hydrated sodium calcium aluminosilicate. Am. J. Vet. Res. 52:152-156.

Harvey, R. B., T. D. Phillips, J. A. Ellis, L. F. Kubena, W. E. Huff and D. V. Peterson: 1991. Effects of aflatoxin Ml residues in milk by addition of hydrated sodium calcium alumi-nosilicate to aflatoxin-contaminated diets of dairy cows. Am. J. Vet. Res. 52:1556-1559.

Kubena, L. F., W. Huff, R. B. Harvey, A. Yersin, M. Elissalde, D. Witzel, L. Giroir, T. D. Phillips and H. Peterson: 1991. Effects of hydrated sodium calcium alumino-silicate on growing turkey poults during aflatoxicosis. Poult. Sci. 70:1823-1830.

Huff, W. E., L. F. Kubena, R. B. Harvey and T. D. Phillips: 1991. Efficacy of hydrated sodium calcium aluminosilicate to reduce the combined toxicity of aflatoxin and ochratoxin A. Poult. Sci.

Kubena, L. F., R. B. Harvey, W. E. Huff, M. H. Elissalde, A. G. Yersin, T. D. Phillips and G. E. Rottinghaus: 1993. Efficacy of HSCAS to reduce the toxicity of aflatoxin and diacetoxy-scirpenol. Poult. Sci. 72:51-59.

Harvey, R. B., L. F. Kubena, M. H. Elissalde and T. D. Phillips. 1993. Efficacy of zeolitic ore compounds on the toxicity of aflatoxin to growing broiler chickens. Avian Diseases 37:67-73.

Kubena, L. F., R. B. Harvey, T. D. Phillips and B. A. Clement. 1993. Effect of hydrated sodium calcium aluminosilicates on aflatoxicosis in broiler chicks. Poult. Sci. 72:651-657.

Phillips, T. D., B. A. Clement, and D. L. Park. 1994. Approaches to reduction of aflatoxins in foods and feeds. In: The Toxicology of Aflatoxins: Human Health, Veterinary, and Agricultural Significance (D. Eaton and J. Groopman, eds), pp. 383-406, A. Press, NY.

Harvey, R., L. Kubena, M. Elissalde, D. Corrier, and T. D. Phillips. 1994. Comparison of two hydrated sodium calcium aluminosilicate compounds to experimentally protect growing barrows from aflatoxicosis. J. Vet. Diagn Invest 6:88-92.

Smith, E. E., T. D. Phillips, J. A. Ellis, R. B. Harvey, L. F. Kubena, J. Thompson, and G. Newton: 1994. Dietary hydrated sodium calcium aluminosilicate reduction of aflatoxin M1 residue in dairy goat milk and effects on milk production and components. J. Anim. Sci. 72:677-682.

Sarr, A. B., K. Mayura, and T. D. Phillips: 1994. Effects of hydrated sodium calcium aluminosilicate on the metabolic profile of AFB1 in Fischer-344 rats. Toxicol. Lett. 75:145-151.

Phillips, T. D., A. B. Sarr, and P. G. Grant. 1995. Selective chemisorption and detoxification of aflatoxins by phyllosilicate clay. Natural Toxins. 3:204-213.

Washburn, K. S, and T. D. Phillips. 1995. Development of a field-practical assay for water-solvated chlorophenols. J. Hazard. Mat. 41:371-381.

Abo-Norag, M., T. S. Edrington, L. F. Kubena, R. B. Harvey, and T. D. 1995. Phillips. Influence of hydrated sodium calcium aluminosilicate and virginiamycin on aflatoxicosis in broiler chicks. Poult. Sci. 74:626-632.

Safe, S., K. Washburn, T. Zacharewski and T. Phillips. 1995. Synthesis and characterization of hydroxylated polychlorinated biphenyls (PCBs) identified in human serum. Chemo-sphere. 31:3017-3023.

Ramu, J., Clark, K., Woode, G. N., Sarr, A. B. and T. D. Phillips. 1997. Adsorption of cholera and heat-labile *Escherichia coli* enterotoxins by various adsorbents: An in vitro study. J. Fd. Protect. 60:1-5.

Grant, P. G., and T. D. Phillips. 1998. Isothermal adsorption of aflatoxin B1 on HSCAS. J. Ag. Fd. Chem. 46:599-605.

Clark, K. J., A. B. Sarr, P. G. Grant, T. D. Phillips and G. N. Woode. 1998. In vitro studies on the use of clay, clay minerals and charcoal to adsorb bovine rotavirus and bovine coronavirus. Vet. Microbiol. 63:137-146.

Grant, P. G., S. L. Lemke, M. R. Dwyer and T. D. Phillips. 1998. Modified Langmuir equation for S-shaped and multisite isotherm plots. J. Langmuir 14(15):4292-4299.

Lemke, S. L., P. G. Grant and T. D. Phillips. 1998. Adsorption of zearalenone by organophilic montmorillonite clay. J. Ag. Fd. Chem. 46:3789-3796.

Lopez, Y., N. P. Keller, B. Sarr, T. D. Phillips, R. G. Cuero and O. D. Smith. 1998. Visual estimation of aflatoxin production in peanut with *Aspergillus* norsolorinic acid mutants. Peanut Sci. 25:92-99.

Huebner, H. J., Lemke, S. L., Ottinger, S. E., Mayura, K., and Phillips, T. D. 1999. Molecular characterization of high affinity, high capacity clays for the equilibrium sorption of ergotamine. Food Additives and Contam. 16:159-171.

Phillips, T. D. 1999. Dietary clay in the chemoprevention of aflatoxin-induced disease. Toxicological Sciences 52:118-126.

Lemke, S. L., Mayura, K., Reeves, W. R., Wang, N., Fickey, C. and Phillips, T. D. 2001. Investigation of organophilic montmorillonite clay inclusion in zearalenone-contaminated diets using the mouse uterine weight bioassay. J. Toxicol. Environ. Hlth.: 62:243-258.

Lemke, S. L., Ottinger, S. E., Mayura, K., Ake, C. L., Pimpukdee, K., Wang, N. and Phillips, T. D. 2001.

Development of a multi-tiered approach to the in vitro prescreening of clay-based enterosorbents. Animal Feed Sci. Technol. 93:17-29

Phillips, T. D., Lemke, S. L. and Grant, P. 2002. Characterization of clay-based enterosorbents for the prevention of aflatoxicosis. Advances in Experimental Medicine and Biology (Eds, J. W. DeVries, M. W. Trucksess, and L. S. Jackson), Vol. 504, pp. 157-173, Kluwer Academic/Plenum Publishers, New York.

Bingham A. K., Phillips T. D., Bauer J. E. 2003. Potential for dietary protection against the effects of aflatoxins in animals. J Am Vet Med. Assoc. 222(5): 591-6.

Pimpukdee, K., Kubena, L. F., Bailey, C. A., Huebner, H. J., Afriyie-Gyawu, E., and Phillips, T. D. 2004. Aflatoxin-induced toxicity and depletion of hepatic vitamin A in young broiler chicks: Protection of chicks in the presence of low levels of NOVASIL PLUS☐ in the diet, Poult. Sci. 83: 737-744.

Herrera, P., Burghardt, R., Huebner, H. J. and Phillips, T. D., 2004. The efficacy of sand-immobilized organoclays as filtration bed materials for bacteria. Food Microbiol. 21: 1-10.

Wiles, M. W., Huebner, H. J., Afriyie-Gyawu, E., Taylor, R. J., Bratton, G. R., and Phillips, T. D., 2004. Toxicological evaluation and metal bioavailability in pregnant rats following exposure to clay minerals in the diet. J. Toxicol Environ. Hlth. Part A. 67 (11): 863-874.

Huebner, H. J., Herrera, P., and Phillips, T. D. 2004. Clay-based interventions for the control of chemical and microbial hazards in food and water. In: Preharvest and Postharvest Food Safety—Contemporary Issues and Future Directions (Eds, R. C. Beier, S. D. Pillai, and T. D. Phillips), IFT Press and Blackwell Publishing, Ames, Iowa Bingham, A. K., Huebner, H. J., Phillips, T. D., and Bauer, J. E. 2004. Identification and reduction of urinary aflatoxin metabolites in dogs. Food and Chemical Toxicology, 42, 1851-1858.

Williams, J. H., Phillips, T. D., Jolly, P. E., Stiles, J. K., Jolly, C. M. and Aggarwal, D. 2004. Human aflatoxicosis in developing countries: A review of toxicology, exposure, potential health consequences and interventions. Am. J. Clin Nutr 80: 1106-22.

Cizmas L, McDonald T J, Phillips T D, Gillespie A M, Lingenfelter R A, Kubena L F, Phillips T D, Donnelly K C. 2004. Toxicity characterization of complex mixtures using biological and chemical analysis in preparation for assessment of mixture similarity. Environ Sci Technol. 38(19):5127-33.

Afriyie-Gyawu, E., Mayura, K., Wiles, M. C., Huebner, H. J., Julian, J., Fickey, C. and Phillips, T. D., 2005. Prevention of zearalenone-induced hyperestrogenism in prepubertal mice. J. Toxicol Environ. Hlth. Part A. 68: 353-368.

Wiles, M. C., Ake, C. L., Donnelly, K. C., McDonald, T. J., Huebner, H. J., Burghardt, R. C., and Phillips, T. D., 2005. Matrix-immobilized organoclay for the removal of toxic contaminants from groundwater. Chemosphere (In Press).

Jolly, P., Jiang, Y., Ellis, W., Awuah, R., Nnedu, O., Phillips, T., Wang, J. S., Afriyie-Gyawu, E., Tang, L., Person, S., Williams, J., Jolly, C. 2006. Determinants of aflatoxin levels in Ghanaians: sociodemographic factors, knowledge of aflatoxin and food handling and consumption practices. Int J Hyg Environ Health 209: 345-58.

Phillips, T. D., Afriyie-Gyawu, E., Wang, J.-S., Williams, J., Huebner, H.2006. The potential of aflatoxin sequestering clay, D. Barug, D. Bhatnagar, H. P. van Egmond, J. W. van der Kamp, W. A. van Osenbruggen, A. Visconti, eds, In: The Mycotoxin Factbook, Wageningen Academic Publishers, The Netherlands, pp. 329-46.

Wang, J.-S., Luo, H., Billam, M., Wang, Z., Guan, H., Tang, L., Goldston, T., Afriyie-Gyawu, E., Lovett, C., Griswold, J., Brattin, B., Taylor, R. J., Huebner, H. J., Phillips, T. D. 2005. Short-term safety evaluation of processed calcium montmorillonite clay (NovaSil) in humans. Food Addit Contam 22: 270-9.

Wang, J.-S., Qian, G. S., Zarba, A., He, X., Zhu, Y. R., Zhang, B. C., Jacobson, L., Gange, S. J., Munoz, A., Kensler, T. W., et al. 1996. Temporal patterns of aflatoxin-albumin adducts in hepatitis B surface antigen-positive and antigen-negative residents of Daxin, Qidong County, People's Republic of China. Cancer Epidemiol Biomarkers Prev 5: 253-61.

Wang, J.-S., Shen, X., He, X., Zhu, Y. R., Zhang, B. C., Wang, J. B., Qian, G. S., Kuang, S. Y., Zarba, A., Egner, P. A., Jacobson, L. P., Munoz, A., Helzlsouer, K. J., Groopman, J. D., Kensler, T. W. 1999. Protective alterations in phase 1 and 2 metabolism of aflatoxin $B_1$ by oltipraz in residents of Qidong, People's Republic of China. J Natl Cancer Inst 91: 347-54.

Wang, L. Y., Hatch, M., Chen, C. J., Levin, B., You, S. L., Lu, S. N., Wu, M. H., Wu, W. P., Wang, L. W., Wang, Q., Huang, G. T., Yang, P. M., Lee, H. S., Santella, R. M. 1996. Aflatoxin exposure and risk of hepatocellular carcinoma in Taiwan. Int J Cancer 67: 620-5.

Wang, J.-S., Abubaker, S., He, X., Sun, G., Strickland, P. T., Groopman, J. D. 2001. Development of aflatoxin B(1)-lysine adduct monoclonal antibody for human exposure studies. Appl Environ Microbiol 67: 2712-2717.

Wang, J.-S., Groopman, J. D. 1999. DNA damage by mycotoxins. Mutat Res 424: 167-81.

Wang, J.-S., Huang, T., Su, J., Liang, F., Wei, Z., Liang, Y., Luo, H., Kuang, S. Y., Qian, G. S., Sun, G., He, X., Kensler, T. W., Groopman, J. D. 2001. Hepatocellular carcinoma and aflatoxin exposure in Zhuqing Village, Fusui County, People's Republic of China. Cancer Epidemiol Biomarkers Prev 10: 143-6.

Gange, S. J., Munoz, A., Wang, J. S., Groopman, J. D. 1996. Variability of molecular biomarker measurements from nonlinear calibration curves. Cancer Epidemiol Biomarkers Prev 5: 57-61.

Groopman, J. D., Hasler, J. A., Trudel, L. J., Pikul, A., Donahue, P. R., Wogan, G. N. 1992. Molecular dosimetry in rat urine of aflatoxin-N7-guanine and other aflatoxin metabolites by multiple monoclonal antibody affinity chromatography and immunoaffinity/high performance liquid chromatography. Cancer Res 52: 267-74.

Sarr, A. B., Mayura, K., Kubena, L. F., Harvey, R. B., Phillips, T. D. 1995. Effects of phyllosilicate clay on the metabolic profile of aflatoxin $B_1$ in Fischer-344 rats. Toxicol Lett 75: 145-51.

Afriyie-Gyawu, E., Ankrah, N.-A., Huebner, H., Ofosuhene, M., Kumi, J., Johnson, N., Tang, L., Xu, L., Jolly, P., Ellis, W., Ofori-Adjei, D., Williams, J., Wang, J.-S., Phillips, T. 2007. NovaSil clay intervention in Ghanaians at high risk for aflatoxicosis: I. Study design and clinical outcomes. Food Additives and Contaminants 24

Brunner, E., Domhof, S., Langer, F. "Nonparametric analysis of longitudinal data in factorial experiments" John. Wiley, New York, N.Y. (2002).

What is claimed is:

1. An oral composition capable of binding an aflatoxin comprising:
an effective amount of an isolated calcium aluminosilicate clay having an particle size less than 80 microns has a detectable level of OCDD and is free from detectable levels of total tetra-dioxin, total penta-dioxin, and total hexa-dioxin;
wherein the detectable levels of total tetra-dioxin are above 0.024 pg/L;
the detectable levels of total penta-dioxin are above 0.025 pg/L; and the detectable levels of total hexa-dioxin are above 0.039 pg/L;
wherein the detectable level of OCDD is about 0.362 pg/L;
wherein an orally consumed effective amount of the isolated calcium aluminosilicate clay composition is useful for mitigating toxic effects of the aflatoxin in a living system at risk for aflatoxicosis.

2. The composition of claim 1, wherein the isolated calcium aluminosilicate clay has a chemical composition comprising:
CaO above about 3.2%; MgO ranging from about 4.0 to about 5.4%; $Fe_2O_3$ ranging from about 5.4 to about 6.5; $K_2O$ ranging from about 0.50 to about 0.90%; $Na_2O$ ranging from about 0.10 to about 0.30%; MnO ranging from about 0.01 to about 0.03%; $Al_2O_3$ ranging from about 14.8 to about 18.2%;
and $SiO_2$ ranging from about 62.4 to about 73.5%; wherein, the chemical composition is given as weight percent.

3. The composition of claim 1, wherein the aflatoxins are selectively sorbed to the calcium aluminosilicate clay composition.

4. The composition of claim 1, wherein the isolated calcium aluminosilicate clay composition exhibits a pH ranging from about 5 to about 9 in solution.

5. An oral composition for use as a preventive therapy to mitigate effects of environmental toxins in a living system, comprising:
an effective amount of an isolated calcium aluminosilicate clay having an average particle size less than 80 microns has a detectable level of OCDD and is free from detectable levels of total tetra-dioxin, total penta-dioxin, and total hexa-dioxin;
the isolated calcium aluminosilicate clay is capable of binding the environmental toxins;
wherein total tetra-dioxin have detectable levels above 0.024 pg/L; total penta-dioxin have detectable levels above 0.025 pg/L; and total hexa-dioxin have detectable levels above 0.039 pg/L;
wherein the detectable level of OCDD is about 0.362 pg/L;
wherein an orally consumed effective amount of the isolated calcium aluminosilicate clay composition is useful for mitigating effects of the environmental toxins in a living system at risk for environmental toxin exposure.

6. The composition of claim 5, wherein the isolated calcium aluminosilicate clay has a chemical composition comprising:
CaO above about 3.2%; MgO ranging from about 4.0 to about 5.4%; $Fe_2O_3$ ranging from about 5.4 to about 6.5; $K_2O$ ranging from about 0.50 to about 0.90%; $Na_2O$ ranging from about 0.10 to about 0.30%; MnO ranging from about 0.01 to about 0.03%; $Al_2O_3$ ranging from about 14.8 to about 18.2%;
and $SiO_2$ ranging from about 62.4 to about 73.5%; wherein, the chemical composition is given as weight percent.

7. The composition of claim 5, wherein the aflatoxins are selectively sorbed to the calcium aluminosilicate clay composition.

8. The composition of claim 5, wherein the isolated calcium aluminosilicate clay composition exhibits a pH ranging from about 5 to about 9 in solution.

9. A method of mitigating an effect of an environmental toxin in a system, comprising steps:
(a) administering orally an effective amount of an isolated calcium aluminosilicate clay having an average particle size less than 80 microns has a detectable level of OCDD about 0.362 pg/L and is free from detectable levels of total tetra-dioxin having a detectable levels above 0.024 pg/L; total penta-dioxin having detectable levels above 0.025 pg/L; and total hexa-dioxin having detectable levels above 0.039 pg/L;
(b) waiting a period of time; and
(c) repeating step (a)-(b) until the effects of the environmental toxin are mitigated.

10. The method of claim 9, further comprising the step of: selecting the isolated calcium aluminosilicate clay to have a chemical composition comprising: CaO above 3.2%; MgO ranging from about 4.0 to about 5.4%; $Fe_2O_3$ ranging from about 5.4 to about 6.5; $K_2O$ ranging from about 0.50 to about 0.90%; $Na_2O$ ranging from about 0.10 to about 0.30%; MnO ranging from about 0.01 to about 0.03%; $Al_2O_3$ ranging from about 14.8 to about 18.2%; and $SiO_2$ ranging from about 62.4 to about 73.5%; wherein, the chemical composition is given as weight percent.

11. The method of claim 9, further comprising a step of: selecting the system to be one predisposed to cancer.

12. The method of claim 9, further comprising a step of: selecting the period of time to be less than about 24 hours.

13. The method of claim 9, further comprising a step of: selecting the isolated calcium aluminosilicate clay to have a pH ranging from about 5 to about 9.

14. A method of mitigating an exposure risk in a system for liver cancer and aflatoxicosis when the system is exposed to an environmental aflatoxin, the method comprising the steps:
(a) administering orally an effective amount of an isolated calcium clay having an average particle size less than 80 microns has a detectable level of OCDD about 0.362 pg/L and is free from detectable levels of total tetra-dioxin having detectable levels above 0.024 pg/L; total penta-dioxin having detectable levels above 0.025 pg/L; and total hexa-dioxin having detectable levels above 0.039 pg/L;
(b) waiting a period of time; and
(c) repeating step (a)-(b) until the system is free of exposure risk to aflatoxins.

15. The method of claim 14, further comprising selecting the isolated calcium aluminosilicate clay to have a chemical composition comprising: CaO above 3.2%; MgO ranging from about 4.0 to about 5.4%; $Fe_2O_3$ ranging from about 5.4 to about 6.5; $K_2O$ ranging from about 0.50 to about 0.90%; $Na_2O$ ranging from about 0.10 to about 0.30%; MnO ranging from about 0.01 to about 0.03%; $Al_2O_3$ ranging from about 14.8 to about 18.2%; and $SiO_2$ ranging from about 62.4 to about 73.5%; wherein, the chemical composition is given as weight percent.

16. The method of claim 14, further comprising selecting the system to be one predisposed to liver cancer and aflatoxicosis.

17. The method of claim 14, further comprising selecting the period of time to be less than about 24 hours.

18. The method of claim 14, further comprising a step of: selecting the isolated calcium aluminosilicate clay to have a pH ranging from about 5 to about 9.

19. A method of treating a subject exposed to high levels of aflatoxin, or low levels of aflatoxin over an extended period of time, comprising:
(a) administering orally an effective amount of an isolated calcium aluminosilicate clay having an average particle size less than 80 microns has a detectable level of OCDD about 0.362 pg/L and is free from detectable levels of total tetra-dioxin having a detectable levels above 0.024 pg/L; total penta-dioxin having detectable levels above 0.025 pg/L; and total hexa-dioxin having detectable levels above 0.039 pg/L;
(b) waiting a period of time; and
(c) repeating step (a)-(b) until the subject's effects of exposure to aflatoxins are lessened or eliminated.

20. The method of claim 19, further comprising selecting the isolated calcium aluminosilicate clay to have a chemical composition comprising: CaO above 3.2%; MgO ranging from about 4.0 to about 5.4%; $Fe_2O_3$ ranging from about 5.4 to about 6.5; $K_2O$ ranging from about 0.50 to about 0.90%; $Na_2O$ ranging from about 0.10 to about 0.30%; MnO ranging from about 0.01 to about 0.03%; $Al_2O_3$ ranging from about 14.8 to about 18.2%; and $SiO_2$ ranging from about 62.4 to about 73.5%; wherein, the chemical composition is given as weight percent.

21. The method of claim 19, further comprising selecting the system to be one predisposed to liver cancer and aflatoxicosis.

22. The method of claim 19, further comprising selecting the period of time to be less than about 24 hours.

23. The method of claim 19, further comprising a step of: selecting the isolated calcium aluminosilicate clay to have a pH ranging from about 5 to about 9.

* * * * *